United States Patent
Carmena et al.

(10) Patent No.: US 12,274,877 B2
(45) Date of Patent: Apr. 15, 2025

(54) DEVICES AND METHODS FOR MODULATING IMMUNE SYSTEM ACTIVITY IN A CANCER PATIENT AND TREATING CANCER

(71) Applicant: Iota Biosciences, Inc., Alameda, CA (US)

(72) Inventors: Jose M. Carmena, Alameda, CA (US); Michel M. Maharbiz, El Cerrito, CA (US); Ryan Neely, El Cerrito, CA (US); Joshua Kay, Oakland, CA (US); Giana Montero Garnier, Berkeley, CA (US)

(73) Assignee: IOTA BIOSCIENCES, INC., Alameda, CA (US)

( * ) Notice: Subject to any disclaimer, the term of this patent is extended or adjusted under 35 U.S.C. 154(b) by 0 days.

(21) Appl. No.: 17/767,409

(22) PCT Filed: Oct. 16, 2020

(86) PCT No.: PCT/US2020/056159
§ 371 (c)(1),
(2) Date: Apr. 7, 2022

(87) PCT Pub. No.: WO2021/077020
PCT Pub. Date: Apr. 22, 2021

(65) Prior Publication Data
US 2024/0100327 A1  Mar. 28, 2024

Related U.S. Application Data

(60) Provisional application No. 62/916,703, filed on Oct. 17, 2019.

(51) Int. Cl.
*A61N 1/00* (2006.01)
*A61N 1/36* (2006.01)
(Continued)

(52) U.S. Cl.
CPC ....... *A61N 1/36002* (2017.08); *A61N 1/3606* (2013.01); *A61N 1/36139* (2013.01);
(Continued)

(58) Field of Classification Search
None
See application file for complete search history.

(56) References Cited

U.S. PATENT DOCUMENTS 4,183,104 A   1/1980 Frey
4,227,265 A   10/1980 Frey
(Continued)

FOREIGN PATENT DOCUMENTS

CN   101048194 A   10/2007
CN   101939048 A   1/2011
(Continued)

OTHER PUBLICATIONS

Arbabian, A. et al. (Dec. 1, 2016, e-pub. Nov. 11, 2016). "Sound Technologies, Sound Bodies: Medical Implants With Ultrasonic Links," IEEE Microwave Magazine 17(12):39-54.
(Continued)

*Primary Examiner* — Sana Sahand
(74) *Attorney, Agent, or Firm* — MORRISON & FOERSTER LLP

(57) ABSTRACT

Described herein are methods and devices for monitoring or modulating an immune system in a subject with cancer, and methods and devices for treating a cancer in a subject. The implanted device can electrically stimulate the splenic nerve of the subject, which can modulate the inflammatory system (for example, by increasing or decreasing the blood level of one or more pro-inflammatory cytokines and/or anti-inflammatory cytokines to increase or decrease inflammation in the subject) and/or activate or increase circulation of one or more immune cells (such as natural killer cells and/or
(Continued)

cytotoxic T-cells), for the treatment of cancer. The implanted medical device includes two or more electrodes configured to electrically stimulate the splenic nerve, and may further include an ultrasonic transducer configured to receive ultrasonic waves and convert energy from the ultrasonic waves into an electrical energy that powers the device.

17 Claims, 26 Drawing Sheets

(51) Int. Cl.
 *A61N 1/372* (2006.01)
 *A61N 1/378* (2006.01)
 *A61N 1/05* (2006.01)
(52) U.S. Cl.
 CPC ..... *A61N 1/36157* (2013.01); *A61N 1/36171* (2013.01); *A61N 1/36178* (2013.01); *A61N 1/37217* (2013.01); *A61N 1/3787* (2013.01); *A61N 1/0556* (2013.01)

(56) References Cited

U.S. PATENT DOCUMENTS

| | | | |
|---|---|---|---|
| 4,681,585 | A | 7/1987 | Sayano |
| 5,095,905 | A | 3/1992 | Klepinski |
| 5,193,539 | A | 3/1993 | Schulman |
| 5,282,468 | A | 2/1994 | Klepinski |
| 6,170,488 | B1 | 1/2001 | Spillman, Jr. |
| 6,200,265 | B1 | 3/2001 | Walsh |
| 6,802,811 | B1 | 10/2004 | Slepian |
| 6,885,888 | B2 | 4/2005 | Rezai |
| 7,024,248 | B2 | 4/2006 | Penner |
| 7,283,874 | B2 | 10/2007 | Penner |
| 7,418,292 | B2 | 8/2008 | Shafer |
| 7,616,990 | B2 | 11/2009 | Chavan |
| 7,617,001 | B2 | 11/2009 | Penner |
| 7,634,318 | B2 | 12/2009 | Tran |
| 7,756,587 | B2 | 7/2010 | Penner |
| 7,757,565 | B2 | 7/2010 | Chakrabartty |
| 7,769,442 | B2 | 8/2010 | Shafer |
| 7,778,704 | B2 | 8/2010 | Rezai |
| 7,794,499 | B2 | 9/2010 | Navarro |
| 7,894,907 | B2 | 2/2011 | Cowan |
| 7,899,542 | B2 | 3/2011 | Cowan |
| 8,285,389 | B2 | 10/2012 | Libbus et al. |
| 8,340,778 | B2 | 12/2012 | Tran |
| 8,412,338 | B2 | 4/2013 | Faltys |
| 8,478,428 | B2 | 7/2013 | Cowley |
| 8,494,642 | B2 | 7/2013 | Cowan |
| 8,494,643 | B2 | 7/2013 | Cowan |
| 8,515,520 | B2 | 8/2013 | Brunnett et al. |
| 8,515,544 | B2 | 8/2013 | Daly |
| 8,577,460 | B2 | 11/2013 | Penner |
| 8,612,002 | B2 | 12/2013 | Faltys |
| 8,660,648 | B2 | 2/2014 | Chavan |
| 8,774,928 | B2 | 7/2014 | Towe |
| 8,788,034 | B2 | 7/2014 | Levine |
| 8,805,537 | B1 | 8/2014 | Cong et al. |
| 8,849,412 | B2 | 9/2014 | Perryman |
| 8,855,767 | B2 | 10/2014 | Faltys |
| 8,874,233 | B2 | 10/2014 | Mclaughlin |
| 8,886,339 | B2 | 11/2014 | Faltys |
| 8,903,501 | B2 | 12/2014 | Perryman |
| 8,934,972 | B2 | 1/2015 | Penner |
| 8,938,300 | B2 * | 1/2015 | Rosero ............... A61N 1/372 607/45 |
| 8,996,116 | B2 | 3/2015 | Faltys |
| 9,162,064 | B2 | 10/2015 | Faltys |
| 9,174,041 | B2 | 11/2015 | Faltys |
| 9,174,044 | B2 | 11/2015 | Mclaughlin |
| 9,199,089 | B2 | 12/2015 | Perryman |
| 9,211,409 | B2 | 12/2015 | Tracey |
| 9,211,410 | B2 | 12/2015 | Levine |
| 9,220,897 | B2 | 12/2015 | Perryman |
| 9,242,103 | B2 | 1/2016 | Perryman |
| 9,409,030 | B2 | 8/2016 | Perryman |
| 9,544,068 | B2 | 1/2017 | Arbabian |
| 9,566,449 | B2 | 2/2017 | Perryman |
| 9,597,508 | B2 | 3/2017 | Mclaughlin |
| 9,610,442 | B2 | 4/2017 | Yoo et al. |
| 9,623,253 | B2 | 4/2017 | Perryman |
| 9,662,490 | B2 | 5/2017 | Tracey |
| 9,700,716 | B2 | 7/2017 | Faltys |
| 9,717,921 | B2 | 8/2017 | Perryman |
| 9,731,141 | B2 | 8/2017 | Tran |
| 9,757,571 | B2 | 9/2017 | Perryman |
| 9,789,314 | B2 | 10/2017 | Perryman |
| 9,802,055 | B2 | 10/2017 | Reinke |
| 9,833,621 | B2 | 12/2017 | Levine |
| 9,849,286 | B2 | 12/2017 | Levine |
| 9,925,384 | B2 | 3/2018 | Perryman |
| 9,974,593 | B2 | 5/2018 | Barman |
| 9,974,965 | B2 | 5/2018 | Perryman |
| 9,993,651 | B2 | 6/2018 | Faltys |
| 10,014,570 | B2 | 7/2018 | Arbabian |
| 10,118,054 | B2 | 11/2018 | Maharbiz |
| 10,177,606 | B2 | 1/2019 | Charthad |
| 10,201,706 | B2 | 2/2019 | Schwab |
| 10,220,203 | B2 | 3/2019 | Faltys |
| 10,286,206 | B2 | 5/2019 | Johnson et al. |
| 10,300,309 | B2 | 5/2019 | Maharbiz |
| 10,300,310 | B2 | 5/2019 | Maharbiz |
| 10,576,305 | B2 | 3/2020 | Maharbiz |
| 10,682,530 | B2 | 6/2020 | Maharbiz |
| 10,744,347 | B2 | 8/2020 | Maharbiz |
| 10,765,865 | B2 | 9/2020 | Maharbiz |
| 10,898,736 | B2 | 1/2021 | Maharbiz et al. |
| 11,033,746 | B2 | 6/2021 | Maharbiz et al. |
| 11,717,689 | B2 | 8/2023 | Maharbiz et al. |
| 11,786,124 | B2 | 10/2023 | Maharbiz et al. |
| 11,890,474 | B2 | 2/2024 | Carmena |
| 11,969,596 | B2 | 4/2024 | Carmena |
| 12,004,840 | B2 | 6/2024 | Maharbiz |
| 2003/0236557 | A1 | 12/2003 | Whitehurst et al. |
| 2005/0010265 | A1 | 1/2005 | Baru et al. |
| 2005/0075701 | A1* | 4/2005 | Shafer ............... A61B 5/416 607/72 |
| 2005/0075702 | A1 | 4/2005 | Shafer |
| 2006/0136004 | A1* | 6/2006 | Cowan ............... A61N 1/3621 607/33 |
| 2006/0178703 | A1 | 8/2006 | Huston |
| 2006/0287678 | A1 | 12/2006 | Shafer |
| 2007/0027486 | A1* | 2/2007 | Armstrong ......... A61N 1/36071 607/45 |
| 2007/0093875 | A1 | 4/2007 | Chavan |
| 2007/0255333 | A1 | 11/2007 | Giftakis et al. |
| 2007/0293895 | A1 | 12/2007 | Cowan |
| 2008/0108915 | A1 | 5/2008 | Penner |
| 2009/0018403 | A1 | 1/2009 | Black |
| 2009/0210042 | A1 | 8/2009 | Kowalczewski |
| 2009/0248097 | A1 | 10/2009 | Tracey |
| 2009/0275997 | A1 | 11/2009 | Faltys |
| 2009/0326602 | A1 | 12/2009 | Glukhovsky |
| 2010/0145221 | A1 | 6/2010 | Brunnett et al. |
| 2010/0268078 | A1 | 10/2010 | Scarantino |
| 2010/0331933 | A1 | 12/2010 | Carbunaru et al. |
| 2010/0331993 | A1 | 12/2010 | Gradl |
| 2011/0054569 | A1 | 3/2011 | Zitnik |
| 2011/0184486 | A1* | 7/2011 | De Ridder ......... A61N 1/37264 607/45 |
| 2012/0185007 | A1 | 7/2012 | Ziegler et al. |
| 2013/0062527 | A1 | 3/2013 | Hyde |
| 2013/0073000 | A1 | 3/2013 | Chavan et al. |
| 2013/0165998 | A1 | 6/2013 | Libbus et al. |
| 2013/0238044 | A1 | 9/2013 | Penner |
| 2013/0282070 | A1 | 10/2013 | Cowan |
| 2013/0310909 | A1 | 11/2013 | Simon |
| 2013/0324891 | A1 | 12/2013 | Towe |
| 2014/0094887 | A1 | 4/2014 | True et al. |
| 2014/0228905 | A1 | 8/2014 | Bolea |
| 2014/0253435 | A1 | 9/2014 | Boser |

(56) References Cited

U.S. PATENT DOCUMENTS

| | | |
|---|---|---|
| 2014/0336474 A1 | 11/2014 | Arbabian |
| 2014/0336727 A1 | 11/2014 | Perryman |
| 2015/0032178 A1 | 1/2015 | Simon et al. |
| 2015/0073510 A1 | 3/2015 | Perryman |
| 2015/0105686 A1 | 4/2015 | Vasan |
| 2015/0112233 A1 | 4/2015 | Towe |
| 2015/0241447 A1 | 8/2015 | Zitnik |
| 2015/0273210 A1 | 10/2015 | Johnson |
| 2015/0297900 A1 | 10/2015 | Perryman |
| 2016/0007836 A1 | 1/2016 | Kikuchi |
| 2016/0007893 A1 | 1/2016 | Roberts |
| 2016/0015988 A1 | 1/2016 | Perryman et al. |
| 2016/0023003 A1 | 1/2016 | Perryman |
| 2016/0023005 A1 | 1/2016 | Perryman |
| 2016/0038741 A1 | 2/2016 | Perryman |
| 2016/0038769 A1 | 2/2016 | Sullivan |
| 2016/0045743 A1 | 2/2016 | Liu |
| 2016/0067497 A1 | 3/2016 | Levine |
| 2016/0096016 A1 | 4/2016 | Tracey et al. |
| 2016/0114165 A1 | 4/2016 | Levine |
| 2016/0235329 A1 | 8/2016 | Bernstein |
| 2016/0331952 A1 | 11/2016 | Faltys |
| 2016/0331962 A1 | 11/2016 | Schwab |
| 2016/0339238 A1 | 11/2016 | Ahmed |
| 2016/0361535 A1 | 12/2016 | Perryman et al. |
| 2016/0367823 A1 | 12/2016 | Cowan et al. |
| 2017/0001003 A1 | 1/2017 | Pivonka |
| 2017/0007836 A1 | 1/2017 | Nassif |
| 2017/0007853 A1 | 1/2017 | Alford |
| 2017/0043156 A1 | 2/2017 | Possover |
| 2017/0095198 A1 | 4/2017 | Towe |
| 2017/0095667 A1 | 4/2017 | Yakovlev |
| 2017/0100588 A1 | 4/2017 | Schwab |
| 2017/0100589 A1 | 4/2017 | Schwab |
| 2017/0100604 A1 | 4/2017 | Schwab |
| 2017/0100605 A1 | 4/2017 | Schwab |
| 2017/0117753 A1 | 4/2017 | Charthad |
| 2017/0125892 A1 | 5/2017 | Arbabian |
| 2017/0136244 A1 | 5/2017 | Bonde |
| 2017/0173328 A1 | 6/2017 | Ostroff |
| 2017/0197082 A1 | 7/2017 | Pang |
| 2017/0202467 A1 | 7/2017 | Zitnik et al. |
| 2017/0203098 A1 | 7/2017 | Jiang |
| 2017/0266454 A1 | 9/2017 | Amir et al. |
| 2017/0281954 A1 | 10/2017 | Reinke et al. |
| 2017/0304630 A1 | 10/2017 | Plachta |
| 2017/0319858 A1 | 11/2017 | Radziemski et al. |
| 2017/0367591 A1 | 12/2017 | Jorgenson |
| 2018/0008828 A1 | 1/2018 | Perryman |
| 2018/0021214 A1 | 1/2018 | Tracey |
| 2018/0021580 A1 | 1/2018 | Tracey |
| 2018/0027077 A1 | 1/2018 | Melodia |
| 2018/0043157 A1 | 2/2018 | Sharma |
| 2018/0055393 A1 | 3/2018 | Cantwell |
| 2018/0085593 A1 | 3/2018 | Fayram et al. |
| 2018/0085605 A1 | 3/2018 | Maharbiz |
| 2018/0093099 A1 | 4/2018 | Cogan |
| 2018/0117319 A1 | 5/2018 | Chew |
| 2018/0117320 A1 | 5/2018 | Levine |
| 2018/0133474 A1 | 5/2018 | Meadows et al. |
| 2018/0154142 A1 | 6/2018 | Guo et al. |
| 2018/0154156 A1 | 6/2018 | Clark et al. |
| 2018/0161002 A1 | 6/2018 | Alford et al. |
| 2018/0169423 A1 | 6/2018 | Perryman |
| 2018/0236248 A1 | 8/2018 | Perryman |
| 2018/0264277 A1 | 9/2018 | Perryman |
| 2018/0289970 A1 | 10/2018 | Faltys |
| 2018/0289971 A1 | 10/2018 | Yeh et al. |
| 2019/0015675 A1 | 1/2019 | Giarola |
| 2019/0022384 A1* | 1/2019 | Kai .................. A61N 1/3606 |
| 2019/0022427 A1 | 1/2019 | Maharbiz |
| 2019/0022428 A1 | 1/2019 | Maharbiz |
| 2019/0150881 A1 | 5/2019 | Maharbiz |
| 2019/0150882 A1 | 5/2019 | Maharbiz |
| 2019/0150883 A1 | 5/2019 | Maharbiz |
| 2019/0150884 A1 | 5/2019 | Maharbiz |
| 2019/0290913 A1* | 9/2019 | Blancou .............. A61N 1/36171 |
| 2019/0321640 A1 | 10/2019 | Carmena |
| 2019/0321644 A1 | 10/2019 | Maharbiz |
| 2020/0023208 A1 | 1/2020 | Maharbiz |
| 2020/0023209 A1 | 1/2020 | Maharbiz |
| 2020/0114175 A1 | 4/2020 | Maharbiz |
| 2020/0230441 A1 | 7/2020 | Maharbiz |
| 2020/0257136 A1 | 8/2020 | Arbabian et al. |
| 2020/0289857 A1 | 9/2020 | Maharbiz |
| 2020/0324148 A1 | 10/2020 | Maharbiz |
| 2020/0391035 A1 | 12/2020 | Donega et al. |
| 2021/0268294 A1 | 9/2021 | Maharbiz et al. |
| 2021/0308462 A1 | 10/2021 | Carmena et al. |
| 2022/0047869 A1 | 2/2022 | Carmena et al. |
| 2022/0062650 A1 | 3/2022 | Maharbiz et al. |
| 2022/0143414 A1 | 5/2022 | Maharbiz et al. |
| 2022/0296886 A1 | 9/2022 | Bashirullah et al. |
| 2023/0089015 A1 | 3/2023 | Maharbiz et al. |
| 2023/0095948 A1 | 3/2023 | Maharbiz et al. |
| 2023/0233851 A1 | 7/2023 | Neely et al. |
| 2023/0301514 A1 | 9/2023 | Lepe et al. |
| 2023/0414950 A1 | 12/2023 | Maharbiz |
| 2024/0017071 A1 | 1/2024 | Carmena |
| 2024/0024032 A1 | 1/2024 | Kay |
| 2024/0099584 A1 | 3/2024 | Maharbiz |
| 2024/0108882 A1 | 4/2024 | Maharbiz |
| 2024/0148250 A1 | 5/2024 | Maharbiz |
| 2024/0226567 A1 | 7/2024 | Carmena |

FOREIGN PATENT DOCUMENTS

| | | |
|---|---|---|
| CN | 102821814 A | 12/2012 |
| CN | 104254291 A | 12/2014 |
| CN | 104623808 A | 5/2015 |
| CN | 104736197 A | 6/2015 |
| CN | 105228513 A | 1/2016 |
| CN | 105848710 A | 8/2016 |
| CN | 107073257 A | 8/2017 |
| CN | 107106840 A | 8/2017 |
| CN | 107614057 A | 1/2018 |
| CN | 107789730 A | 3/2018 |
| CN | 107864633 A | 3/2018 |
| EP | 1745818 A1 | 1/2007 |
| EP | 2515996 A2 | 10/2012 |
| EP | 2355893 B1 | 12/2013 |
| EP | 2667942 A2 | 12/2013 |
| EP | 2694154 A1 | 2/2014 |
| EP | 2741810 A1 | 6/2014 |
| EP | 2162185 B1 | 7/2015 |
| EP | 1648559 B1 | 9/2015 |
| EP | 2928557 A2 | 10/2015 |
| EP | 2959937 A1 | 12/2015 |
| EP | 2707094 B1 | 2/2016 |
| EP | 2337609 B1 | 8/2016 |
| EP | 2755718 B1 | 12/2017 |
| EP | 3259015 A1 | 12/2017 |
| EP | 3259017 A1 | 12/2017 |
| EP | 2736592 B1 | 1/2018 |
| EP | 3285856 A1 | 2/2018 |
| EP | 2651431 B1 | 3/2018 |
| EP | 3294376 A1 | 3/2018 |
| EP | 3338855 A1 | 6/2018 |
| EP | 2440284 B1 | 9/2018 |
| EP | 3403690 A1 | 11/2018 |
| EP | 3057652 B1 | 7/2023 |
| JP | H04503312 A | 6/1992 |
| JP | 2001170190 A | 6/2001 |
| JP | 2007021225 A | 2/2007 |
| JP | 2011513038 A | 4/2011 |
| JP | 2014525288 A | 9/2014 |
| JP | 2015528385 A | 9/2015 |
| JP | 2019503722 A | 2/2019 |
| RU | 2675350 C1 | 12/2018 |
| WO | 2005032653 A1 | 4/2005 |
| WO | 2006029257 A2 | 3/2006 |
| WO | 2006138068 A2 | 12/2006 |
| WO | 2007050657 A1 | 5/2007 |
| WO | 2007090159 A1 | 8/2007 |

(56) References Cited

FOREIGN PATENT DOCUMENTS

| | | |
|---|---|---|
| WO | 2009114689 A1 | 9/2009 |
| WO | 2009146030 A1 | 12/2009 |
| WO | 2010059617 A2 | 5/2010 |
| WO | 2010059617 A3 | 9/2010 |
| WO | 2010144578 A2 | 12/2010 |
| WO | 2010144578 A3 | 3/2011 |
| WO | 2011028763 A2 | 3/2011 |
| WO | 2011079309 A2 | 6/2011 |
| WO | 2011028763 A3 | 7/2011 |
| WO | 2011079309 A3 | 11/2011 |
| WO | 2012057868 A1 | 5/2012 |
| WO | 2012083259 A2 | 6/2012 |
| WO | 2012103519 A2 | 8/2012 |
| WO | 2012138782 A1 | 10/2012 |
| WO | 2012154865 A2 | 11/2012 |
| WO | 2012154865 A3 | 1/2013 |
| WO | 2013019757 A2 | 2/2013 |
| WO | 2013025632 A1 | 2/2013 |
| WO | 2013028428 A1 | 2/2013 |
| WO | 2013040549 A1 | 3/2013 |
| WO | 2013044207 A1 | 3/2013 |
| WO | 2012083259 A3 | 9/2013 |
| WO | 2013134479 A1 | 9/2013 |
| WO | 2012103519 A3 | 3/2014 |
| WO | 2014055408 A1 | 4/2014 |
| WO | 2013019757 A3 | 5/2014 |
| WO | 2014089299 A2 | 6/2014 |
| WO | 2014153218 A1 | 9/2014 |
| WO | 2014153219 A1 | 9/2014 |
| WO | 2014153223 A1 | 9/2014 |
| WO | 2014153228 A1 | 9/2014 |
| WO | 2014089299 A3 | 10/2014 |
| WO | 2014169145 A1 | 10/2014 |
| WO | 2015127476 A1 | 8/2015 |
| WO | 2015142842 A2 | 9/2015 |
| WO | 2015142842 A3 | 11/2015 |
| WO | 2016028608 A1 | 2/2016 |
| WO | 2016112398 A1 | 7/2016 |
| WO | 2016134197 A1 | 8/2016 |
| WO | 2016134199 A1 | 8/2016 |
| WO | 2016168798 A1 | 10/2016 |
| WO | 2016170510 A1 | 10/2016 |
| WO | 2016183353 A1 | 11/2016 |
| WO | 2016187114 A1 | 11/2016 |
| WO | 2017087681 A1 | 5/2017 |
| WO | 2017143185 A1 | 8/2017 |
| WO | 2017143191 A1 | 8/2017 |
| WO | 2017149438 A1 | 9/2017 |
| WO | 2018005848 A1 | 1/2018 |
| WO | 2018009905 A2 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018017591 A1 | 1/2018 |
| WO | 2018009905 A3 | 2/2018 |
| WO | 2018067630 A1 | 4/2018 |
| WO | 2018081763 A1 | 5/2018 |
| WO | 2018081826 A1 | 5/2018 |
| WO | 2018087193 A1 | 5/2018 |
| WO | 2018089895 A2 | 5/2018 |
| WO | 2018089895 A3 | 6/2018 |
| WO | 2018118857 A1 | 6/2018 |
| WO | 2018118860 A1 | 6/2018 |
| WO | 2018118861 A1 | 6/2018 |
| WO | 2018118864 A1 | 6/2018 |
| WO | 2018118866 A1 | 6/2018 |
| WO | 2019075203 A1 | 4/2019 |
| WO | 2019122903 A2 | 6/2019 |
| WO | 2019122908 A1 | 6/2019 |
| WO | 2019126616 A1 | 6/2019 |
| WO | 2019122903 A3 | 8/2019 |
| WO | 2019204769 A1 | 10/2019 |
| WO | 2019204773 A1 | 10/2019 |
| WO | 2020047152 A1 | 3/2020 |
| WO | 2020117967 A1 | 6/2020 |
| WO | 2020142732 A1 | 7/2020 |
| WO | 2020142733 A1 | 7/2020 |
| WO | 2020254798 A1 | 12/2020 |
| WO | 2021077022 A1 | 4/2021 |
| WO | 2021105699 A1 | 6/2021 |
| WO | 2021105708 A1 | 6/2021 |
| WO | 2021108810 A1 | 6/2021 |
| WO | 2021168163 A1 | 8/2021 |
| WO | 2021168229 A1 | 8/2021 |
| WO | 2021248013 A1 | 12/2021 |
| WO | 2022035889 A1 | 2/2022 |
| WO | 2022046770 A1 | 3/2022 |
| WO | 2023183891 A2 | 9/2023 |
| WO | 2024011141 A2 | 1/2024 |
| WO | 2024086662 A1 | 4/2024 |
| WO | 2024167868 A2 | 8/2024 |
| WO | 2024182632 A2 | 9/2024 |

OTHER PUBLICATIONS

Bertrand, A. et al. (Aug. 2014). "Beamforming Approaches for Untethered, Ultrasonic Neural Dust Motes for Cortical Recording: a Simulation Study," IEEE Embc, 2625-2628.

Beyer, G.P. et al. (Jan. 1, 2008). "An Implantable MOSFET Dosimeter for the Measurement of Radiation Dose in Tissue During Cancer Therapy," IEEE Sensors Journal 8(1):38-51.

Brown, G.L. et al. (1957). "The Output of Sympathetic Transmitter From the Spleen of the Cat," J. Physiol. 138:81-102.

Carnevale, D. et al. (Sep. 27, 2016). "A Cholinergic-Sympathetic Pathway Primes Immunity In Hypertension and Mediates Brain-To-Spleen Communication," Nature Communications, 7:13035, 13 pages.

Celinskis, D. et al. (Aug. 26, 2014). "Wireless Impedance Measurements for Monitoring Peripheral Vascular Disease," 36th Annual International Conference of the IEEE Engineering in Medicine and Biology Society pp. 6937-6940.

Coldewey, D. (Dec. 27, 2018). "Iota Biosciences Raises $15M to Produce In-Body Sensors Smaller Than a Grain of Rice," TechCrunch, 4 pages.

Eckberg, D.L. et al. (1988). "Baroreflex Modulation of Sympathetic Activity and Sympathetic Neurotransmitters in Humans," Acta Physiol. Scand. 133:221-231.

Grossman, N. et al. (Jun. 1, 2017). "Noninvasive Deep Brain Stimulation via Temporally Interfering Electric Fields," Cell 169:1029-1041.

Guyot, M. et al. (2019, e-pub. Mar. 15, 2019). "Apical Splenic Nerve Electrical Stimulation Discloses an Anti-Inflammatory Pathway Relying on Adrenergic and Nicotinic Receptors in Myeloid Cells," Brain, Behavior, and Immunity 80:238-246.

Hellyer, J. et al. (Feb. 2014). "Autonomic Nerve Activity and Blood Pressure in Ambulatory Dogs," Heart Rhythm, 11(2):307-313, 14 pages.

International Preliminary Report on Patentability, issued Apr. 19, 2022, for PCT Application No. PCT/US2020/056159, filed Oct. 16, 2020, 10 pages.

International Search Report and Written Opinion, mailed Jan. 21, 2021 for PCT Application No. PCT/US2020/056159, filed Oct. 16, 2020, 13 pages.

Katafuchi, T. et al. (1993). "Roles of Sympathetic Nervous System in the Suppression of Cytotoxicity of Splenic Natural Killer Cells in the Rat," J. of Physiology 465:343-357.

Kay, J. (May 4, 2017). "Rodent Wearable Ultrasound Interrogation System for Wireless Neural Recording", Berkeley EECS, Technical Report No. UCS/EECS-2017-27, 50 pages.

Kees, M.G. et al. (2003). "Via β-Adrenoceptors, Stimulation of Extrasplenic Sympathetic Nerve Fibers Inhibits Lipopolysaccharide-Induced TNF Secretion in Perfused Rat Spleen," J. of Neuroimmunology 145:77-85.

Kirpekar, S.M. et al. (1967). "Release of Noradrenaline by Splenic Nerve Stimulation and Its Dependence of Calcium," J. Physiol. 188:219-234.

(56) References Cited

OTHER PUBLICATIONS

Mazzilli, F. et al. (Aug. 31-Sep. 4, 2010). "In-Vitro Platform to Study Ultrasound as Source for Wireless Energy Transfer and Communication for Implanted Medical Devices," 32nd Annual International Conference of the IEEE EMBS, pp. 3751-3754.

Mazzilli, F. et al. (Oct. 2014). "A 10.5 cm Ultrasound Link for Deep Implanted Medical Devices," IEEE Transactions on Biomedical Circuits and Systems 8(5):738-750.

Niijima, A. et al. (1991). "The Effects of Interleukin-1β on the Activity of Adrenal, Splenic and Renal Sympathetic Nerves in the Rat," J. of the Autonomic Nervous System 36:183-192.

Ninomiya, I. et al. (Nov. 1971). "Sympathetic Nerve Activity to the Spleen, Kidney, and Heart in Response to Baroceptor Input," American J. of Physiology 221(5):1346-1351.

Peisino, M. (May 17, 2013). "Deeply Implanted Medical Device Based on a Novel Ultrasonic Telemetry Technology," École Polytechnique Fédérale De Lausanne pp. 148.

Perrotta, M. et al. (2018, e-pub. Feb. 24, 2018). "The Interactions of the Immune System and the Brain in Hypertension," Current Hypertension Reports 20:7, 6 pages.

Piech, D.K. et al. (2017). "Rodent Wearable Ultrasound System for Wireless Neural Recording," 39th Annual International Conference of the IEEE Engineering in Medicine and Biology Society, EMBC, 5 pages.

Rayburn, E.R. et al. (2009). "Anti-Inflammatory Agents for Cancer Therapy," Mol. Cell. Pharmacol. 1(1):29-43, 20 pages.

Robertson, M.J. (Feb. 1, 2002). "Role of Chemokines in the Biology of Natural Killer Cells," J. Leukoc. Biol. 71:173-183.

Rosenberg, J. et al. (Mar. 2018, e-pub. Dec. 14. 2017). "CD+ T Cells and NK Cells: Parallel and Complementary Soldiers of Immunotherapy," Curr. Opin. Chem. Eng. 19:1-22.

Seo, D. (May 1, 2016). "Design of Ultrasonic Power Link for Neural Dust", Technical Report No. UCB/EECS-2016-21, Electrical Engineering and Computer Sciences University of California at Berkeley, 71 pages.

Seo, D. et al. (2015). "Ultrasonic Beamforming System for Interrogating Multiple Implantable Sensors," IEEE, pp. 2673-2676.

Seo, D. et al. (Apr. 1, 2015, e-pub. Aug. 7, 2014). "Model Validation of Untethered, Ultrasonic Neural Dust Motes for Cortical Recording," J. of Neuroscience Methods 244:114-122.

Seo, D. et al. (Aug. 3, 2016). "Wireless Recording in the Peripheral Nervous System with Ultrasonic Neural Dust," Neuron 91:529-539.

Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp. 1-11.

Simon, T. et al. (Nov. 11, 2019). "Stimulation of Splenic Neurovascular Bundle Protect Mice from Developing Collagen-Induced Arthritis," Abstract No. 998, 2 pages.

Straub, R. H. et al. (Jul. 2000). "A Bacteria-Induced Switch of Sympathetic Effector Mechanisms Augments Local Inhibition of TNF-α and IL-6 Secretion in the Spleen," The FASEB Journal 14:1380-1388.

Straub, R.H. et al. (2002). "Immunoregulation of IL-6 Secretion by Endogenous and Exogenous Adenosine and by Exogenous Purinergic Agonists in Splenic Tissue Slices," J. of Neuroimmunology 125:73-81.

Tang, H.-Y. et al. (Dec. 2015). "Miniaturizing Ultrasonic System for Portable Health Care and Fitness," IEEE Transactions on Biomedical Circuits and Systems 9(6):767-776.

Taylor, J. et al. (2004). "Multiple-Electrode Nerve Cuffs for Low-Velocity and Velocity-Selective Neural Recording," Medical & Biological Engineering & Computing 42:634-643.

Tsai, J.-Y. et al. (2011). "Ultrasonic Wireless Power and Data Communication for Neural Stimulation," 2011 IEEEE International Ultrasonics Symposium pp. 1052-1055.

U.S. Appl. No. 17/767,419, Maharbiz et al., filed Oct. 16, 2020.

U.S. Appl. No. 18/244,174, Maharbiz et al., filed Sep. 8, 2023.

U.S. Appl. No. 18/414,173, Carmena et al., filed Jan. 16, 2024.

Weissleder, R. et al. (May 1, 2001). "Molecular Imaging," Radiology, Radiological Society of North America, Inc. 219(2):316-333.

Williams, J.M. et al. (1981). "Sympathetic Innervation of Murine Thymus and Spleen: Evidence for a Functional Link Between the Nervous and Immune Systems," Brain Research Bulletin 6:83-94.

Wodlinger, B. et al. (Oct. 2009). "Localization and Recovery of Peripheral Neural Sources With Beamforming Algorithms," IEEE Transactions on Neural Systems and Rehabilitation Engineering 17(5):461-468, 18 pages.

Du, N. et al. (Aug. 17, 2021). "NK Cell Therapy: a Rising Star in Cancer Treatment," Cancers 13(16):4129, 17 pages.

Kalakutsky, L.I. et al. (2012). "Systems of Electrical Stimulation of Organs and Tissues," Ministry of Education and Science of the Russian Federation, Samara State Aerospace University, Electronic Textbook, pp. 13-23, 24, 29-31, 32, 37. [English Translation], 108 pages total.

Kuznetsov, S.A. (2000). "About," Large Explanatory Dictionary of the Russian Language, St. Petersburg, Russia, p. 708, 7 pages. [English Translation].

Martelli, D. et al. (Apr./May/Jun. 2014, e-pub. May 7, 2014). "Neural Control of Inflammation by the Greater Splanchnic Nerves," Temperature 1(1):14-15, 3 pages.

Slavin, K.V. et al. (2016, e-pub. Dec. 1, 2016). "Tonic And Burst Spinal Cord Stimulation Waveforms For the Treatment of Chronic, Intractable Pain: Study Protocol For a Randomized Controlled Trial," Trials 17(569):1-11.

\* cited by examiner

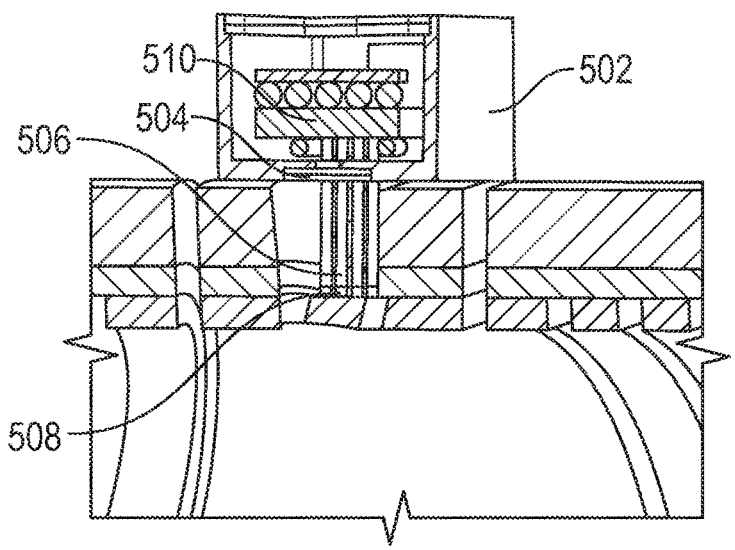
FIG. 5C
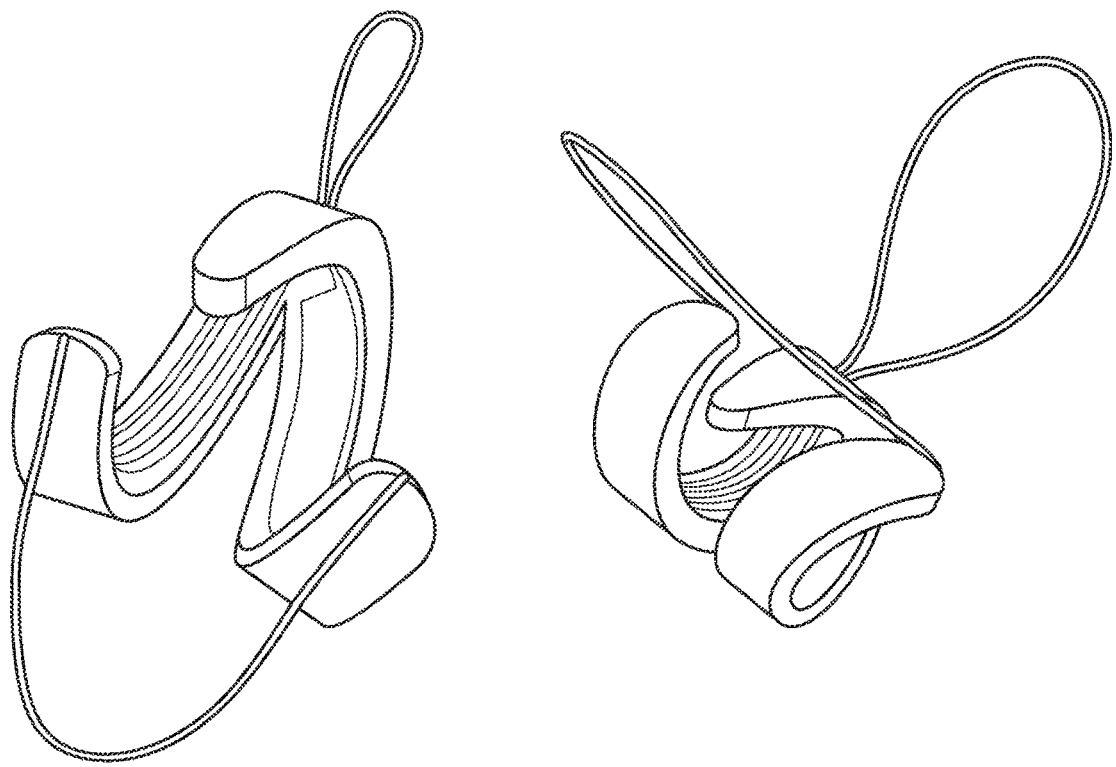
FIG. 6A
FIG. 6B

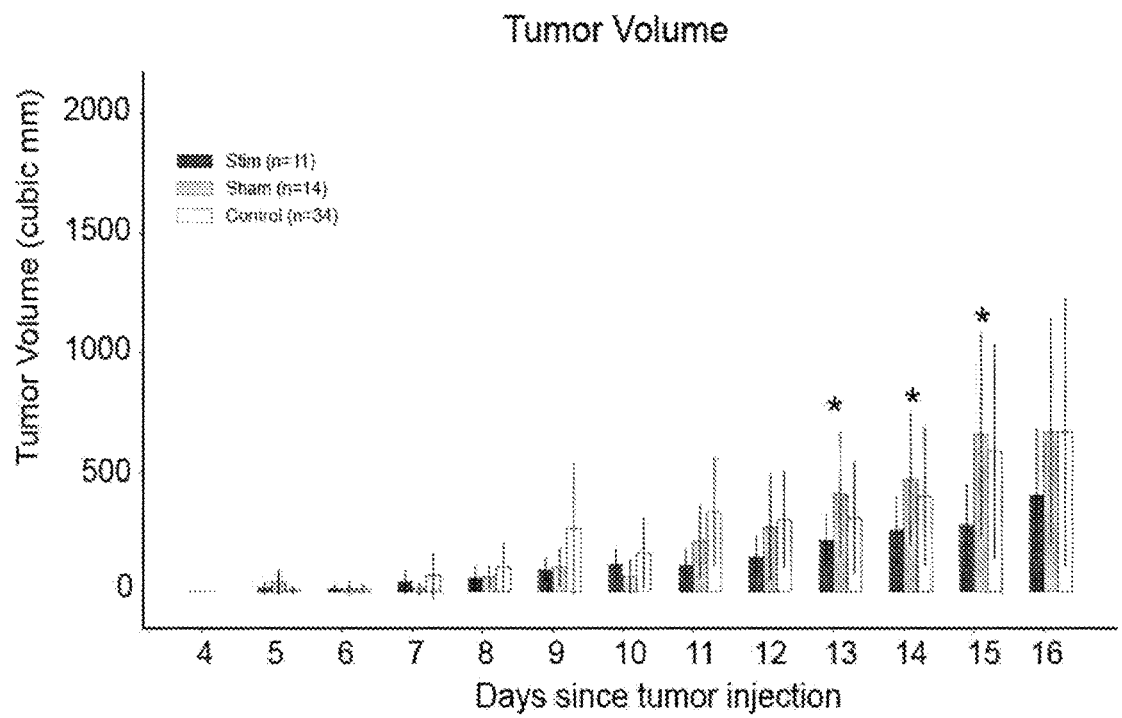
FIG. 22A
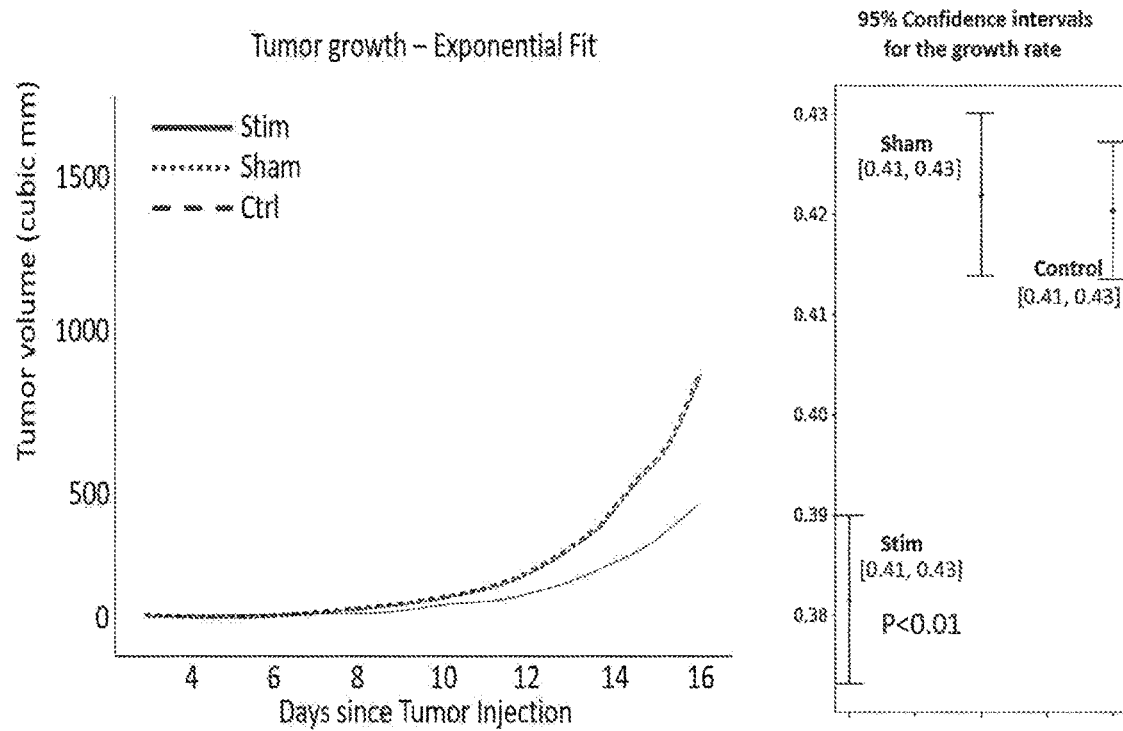
FIG. 22B
FIG. 22C

DEVICES AND METHODS FOR MODULATING IMMUNE SYSTEM ACTIVITY IN A CANCER PATIENT AND TREATING CANCER

CROSS-REFERENCE TO RELATED APPLICATION

This application is a U.S. national phase application under 35 U.S.C. § 371 of International Application No. PCT/US2020/056159, filed on Oct. 16, 2020, which claims the priority benefit to U.S. Provisional Application No. 62/916,703, filed on Oct. 17, 2019, the entire disclosure of each of which is incorporated herein by reference for all purposes.

TECHNICAL FIELD

Described herein are methods of modulating the immune system of a subject with cancer, and methods of treating cancer, using an implanted device configured to electrically stimulate the splenic nerve. Further described are implantable devices and systems for performing such methods.

BACKGROUND

The inflammatory state of a patient with cancer can significantly impact disease prognosis. The innate immune system, including natural killer (NK) cells, generally activates in response to the cancer cells, which is part of the body's natural inflammatory defense system. At the same time, anti-inflammatory agents administered to a patient with cancer have been found to be effective in combination with other cancer treatments for treating the cancer (see Rayburn et al., *Anti-inflammatory Agents for Cancer Therapy*, Mol. Cell. Pharmacol., vol. 1, no. 1, pp. 29-43 (2009)). Thus, careful control of the inflammatory state of a cancer patient can help disease treatment.

While administration of an anti-inflammatory drug to a subject with cancer has been found aid cancer treatment, some amount of inflammation is desirable so that the body's innate immune system can function to target and kill cancer cells. Anti-inflammatory drug dosing is an imprecise mechanism for controlling the inflammatory state of the subject due to inconsistent pharmacokinetics between patients or even the same patient over time. Additionally, most drugs function with peak and trough bioavailabilities following administration, which prevents consistent inflammatory state control.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE INVENTION

Described herein are methods of modulating the immune system (such as by increasing or decreasing inflammation) of a subject with cancer and methods of treating cancer in a subject. Also described are implantable devices configured to modulate the immune system of a subject, implantable devices configured to treat cancer in a subject, and implantable devices configured to reduce inflammation in a subject with cancer, as well as systems that include an interrogator configured to communicate with and/or power such devices.

A method of modulating the immune system of a subject with a cancer may comprise electrically stimulating the splenic nerve of the subject using a fully implanted device comprising one or more electrodes in electrical communication with the splenic nerve sufficient to modulate the immune system of the subject. The method can further comprises identifying a subject with cancer.

A method of treating a cancer in a subject may comprises electrically stimulating the splenic nerve of the subject using a fully implanted device comprising one or more electrodes in electrical communication with the splenic nerve sufficient to modulate the immune system of the subject and treat the cancer in the subject. The method can further comprises identifying a subject with cancer.

In the above methods, modulating the immune system can comprise increasing activation of one or more immune cells in the subject. For example, modulating the immune system can comprise increasing activation of natural killer (NK) cells or cytotoxic T-cells in the subject. Modulating the immune system can comprise increasing circulation and/or activation of NK cells in the subject. Modulating the immune system can comprise decreasing circulation of cytotoxic T cells in the subject. Modulating the immune system can comprise increasing circulation and/or activation of NK cells and decreasing circulation of cytotoxic T cells in the subject.

The method can comprise increasing a blood concentration of an inflammatory cytokine in the subject. Alternatively, the method can comprise decreasing a blood concentration of an inflammatory cytokine. In inflammatory cytokine (either increased or decreased) may be a pro-inflammatory cytokine or an anti-inflammatory cytokine. The inflammatory cytokine may be, for example, tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), or RANTES. The pro-inflammatory cytokine can be tumor necrosis factor alpha (TNF-α), interleukin-6 (IL-6), or interleukin-1β (IL-1β). The anti-inflammatory cytokine can be interleukin-10 (IL-10).

Modulating the immune system can comprise increasing inflammation in the subject. Inflammation in the subject may be increased by increasing a blood concentration of a pro-inflammatory cytokine in the subject, such as tumor necrosis factor alpha (TNF-α), interleukin-6 (IL-6), or interleukin-1β (IL-1β). Inflammation in the subject may be increased by decreasing a blood concentration of an anti-inflammatory cytokine in the subject, such as interleukin-10 (IL-10). Inflammation in the subject may be increased by increasing a blood concentration of a pro-inflammatory cytokine in the subject, such as tumor necrosis factor alpha (TNF-α), and decreasing a blood concentration of an anti-inflammatory cytokine in the subject, such as interleukin-10 (IL-10). Modulating the immune system to increase inflammation can include, electrically stimulating the splenic nerve with plurality of electrical pulses emitted at a frequency of about 25 Hz or higher, such as about 30 Hz to about 100 Hz. Modulating the immune system to increase inflammation can include, electrically stimulating the splenic nerve with plurality of biphasic electrical pulses comprising an anodal phase followed by a cathodal phase.

Alternatively, modulating the immune system can comprise decreasing inflammation in the subject. Inflammation in the subject may be reduced by decreasing a blood concentration of a pro-inflammatory cytokine in the subject, such as tumor necrosis factor alpha (TNF-α), interleukin-6 (IL-6), or interleukin-1β (IL-1β). Inflammation in the subject may be reduced by increasing a blood concentration of an anti-inflammatory cytokine in the subject, such as interleukin-10 (IL-10). Inflammation in the subject may be reduced by reducing a blood concentration of a pro-inflammatory cytokine in the subject, such as tumor necrosis factor alpha (TNF-α), and increasing a blood concentration of an anti-inflammatory cytokine in the subject, such as interleukin-10 (IL-10). Modulating the immune system to reduce inflammation can include, electrically stimulating the splenic nerve with plurality of electrical pulses emitted at a frequency of less than 25 Hz, such as about 3 Hz to about 20 Hz. Modulating the immune system to increase inflammation can include, electrically stimulating the splenic nerve with plurality of biphasic electrical pulses comprising a cathodal phase followed by an anodal phase.

A method of reducing inflammation in a subject with cancer may comprise electrically stimulating the splenic nerve of the subject using a fully implanted device comprising one or more electrodes in electrical communication with the splenic nerve sufficient to modulate the immune system to reduce inflammation in the subject. The method can further comprises identifying the subject with cancer. The inflammation may be associated with pain, fever, non-cancerous tissue necrosis, or shock.

Modulating the immune system can comprise reducing a blood concentration of an inflammatory cytokine in the subject. The inflammatory cytokine can be tumor necrosis factor alpha (TNF-α), interleukin-6 (IL-6), or interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), or RANTES.

Modulating the immune system can comprises decreasing activation of one or more immune cells in the subject. Modulating the immune system can comprise decreasing activation of natural killer (NK) cells or cytotoxic T-cells in the subject. Modulating the immune system can comprise increasing activation and/or circulation of NK cells. Modulating the immune system can comprise increasing activation and/or circulation of NK cells and decreasing circulation of cytotoxic T cells.

The methods can further comprise receiving, at the device, ultrasonic waves from an external ultrasonic transducer; and converting energy from the ultrasonic waves into electrical energy that powers the device. The ultrasonic waves that power the implanted device can be transmitted using an external device.

In the above methods, the splenic nerve can be electrically stimulated using one or more electrical pulses about 1 ms in length or less.

In the above methods, the splenic nerve can electrically stimulated using one or more electrical pulses having an amplitude of about 250 µA to about 10 mA.

In the above methods, the splenic nerve can be electrically stimulated using one or more electrical pulses at a frequency of about 100 Hz or less.

In the above methods, the splenic nerve is electrically stimulated using a pulse train comprising a plurality of biphasic electrical pulses. The biphasic electrical pulses can comprise an anodal phase followed by a cathodal phase. Alternatively, the biphasic electrical pulses can comprise a cathodal phase followed by an anodal phase.

In the above methods, the splenic nerve can be electrically stimulated using one or more biphasic electrical pulses. In the above methods, the splenic nerve can be electrically stimulated using a pulse train comprising a plurality of biphasic electrical pulses. It has been found that the biphasic electrical pulses comprising an anodal phase followed by a cathodal phase are beneficial for increasing inflammation in the subject, such as for increasing a blood concentration of an inflammatory cytokine in the subject. It has been found that the biphasic electrical pulses comprising a cathodal phase followed by an anodal phase are beneficial for reducing inflammation in the subject. The biphasic electrical pulse preferably has a duration of 400 µs or less, such as 300 µs or less, preferably about 200 µs. The duration of the biphasic electrical pulse can be split evenly between the cathodal and anodal phases. The biphasic electrical pulse preferably comprises an inter-phase interval between the anodal phase and cathodal phase. The inter-phase interval preferably has a duration of 10 to 100 µs, such as 30-70 µs, such as 50-60 µs. Such biphasic electrical pulses, or pulse trains comprising such biphasic electrical pulses, are particularly useful in treating cancer. The biphasic electrical pulses can e.g. be delivered at a rate of less than 100 Hz, such as 5-50 Hz. The amplitude of the biphasic electrical pulses can e.g. be 100 µA-2.6 mA, such as about 250 µA to about 1.8 mA. The biphasic pulses can be biphasic square-wave pulses.

In the above methods, the splenic nerve can be electrically stimulated using a plurality of pulse trains comprising two or more electrical pulses, the pulse trains separated by a dwell time of about 50 ms or more, such as about 500 ms or more, or about 50 ms to about 2 minutes. Optionally, the implanted device is wirelessly powered during the dwell time.

In the above methods, the splenic nerve can be electrically stimulated using tonic electrical pulses.

In s the above methods, the splenic nerve may be electrically stimulated in response to a trigger signal. The trigger signal can be encoded in the ultrasonic waves received by the device. The trigger signal can be based on splenic nerve activity. The trigger signal can be based on a deviation from a baseline splenic nerve activity. The trigger signal can be based on a measured physiological condition. The physiological condition can be, for example, a temperature, a pulse rate, or a blood pressure. The physiological condition can be measured by the implanted device. The method can comprise emitting an ultrasonic backscatter encoding information related to the splenic nerve activity or the physiological condition. The ultrasonic backscatter encoding the information related to the splenic nerve activity or the physiological condition can be received by an external device. The ultrasonic backscatter can further encode information related to the status of the device or one or more electrical pulses emitted by the device. The method can comprises transmitting, at the external device, ultrasonic waves that encode the trigger signal. In the above methods, the splenic nerve activity can be monitored by the implanted device.

In the above methods, the implanted device can be fully implanted with in the perivascular fascia surrounding the splenic nerve and splenic artery.

In the above methods, the method can further comprise administering to the subject an anti-cancer drug.

In the above methods, the subject can be a human.

Further described herein is an implantable device configured for use in any one of the above methods.

The implantable device includes two or more electrodes configured to be in electrical communication with a splenic nerve of a subject, e.g., with cancer. The device can be configured to electrically stimulate the splenic nerve. The device can be configured to electrically stimulate the splenic nerve sufficient to modulate the immune system of the subject. The device can be configured to electrically stimulate the splenic nerve sufficient to treat the cancer.

The device can further include a nerve cuff configured to position at least one of the two or more electrodes in electrical communication with the splenic nerve. The nerve cuff can be a helical nerve cuff configured to at least partially wrap around the splenic neurovascular bundle. The device can further include a body comprising a wireless communication system attached to the nerve cuff. The body can be positioned on an outer surface of the helical nerve cuff.

The device can be configured to activate one or more immune cells in the subject upon electrically stimulating the splenic nerve. The device can be configured to activate natural killer (NK) cells or cytotoxic T-cells in the subject upon electrically stimulating the splenic nerve. The device can be configured to activate and/or increase circulation of natural killer (NK) cells in the subject upon electrically stimulating the splenic nerve. The device can be configured to activate and/or increase circulation of natural killer (NK) cells and decrease circulation of cytotoxic T cells in the subject upon electrically stimulating the splenic nerve.

The device can be configured to increase a blood concentration of an inflammatory cytokine in the subject upon electrically stimulating the splenic nerve. Alternatively, the device can be configured to decrease a blood concentration of an inflammatory cytokine in the subject upon electrically stimulating the splenic nerve, the inflammatory cytokine can be tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), or RANTES. The inflammatory cytokine can be a pro-inflammatory cytokine, such as tumor necrosis factor alpha (TNF-α), interleukin-6 (IL-6), or interleukin-1β (IL-1β). The inflammatory cytokine can be an anti-inflammatory cytokine, such as interleukin-10 (IL-10).

The device can be configured to increase inflammation in the subject upon electrically stimulating the splenic nerve. The device can be configured to increase a blood concentration of a pro-inflammatory cytokine in the subject upon electrically stimulating the splenic nerve. The pro-inflammatory cytokine can be, for example, tumor necrosis factor alpha (TNF-α), interleukin-6 (IL-6), or interleukin-1β (IL-1β). The device can be configured to decrease a blood concentration of an anti-inflammatory cytokine in the subject upon electrically stimulating the splenic nerve. The anti-inflammatory cytokine can be, for example, interleukin-10 (IL-10). The device can be configured to increase a blood concentration of tumor necrosis factor alpha (TNF-α) and reduce a blood concentration of interleukin-10 (IL-10) in the subject upon electrically stimulating the splenic nerve. To increase inflammation in the subject, the device can be configured to electrically stimulate the splenic nerve with a plurality of electrical pulses emitted at a frequency of about 25 Hz or higher, such as about 30 Hz to about 100 Hz. The device can be configured to electrically stimulate the splenic nerve using a plurality of biphasic electrical pulses comprising an anodal phase followed by a cathodal phase.

Alternatively, the device can be configured to reduce inflammation in the subject upon electrically stimulating the splenic nerve. The inflammation can be associated with pain, fever, non-cancerous tissue necrosis, or shock. The device can be configured to reduce a blood concentration of a pro-inflammatory cytokine in the subject upon electrically stimulating the splenic nerve. The pro-inflammatory cytokine can be, for example, tumor necrosis factor alpha (TNF-α), interleukin-6 (IL-6), or interleukin-1β (IL-1β). The device can be configured to increase a blood concentration of an anti-inflammatory cytokine in the subject upon electrically stimulating the splenic nerve. The anti-inflammatory cytokine can be, for example, interleukin-10 (IL-10). The device can be configured to decrease a blood concentration of tumor necrosis factor alpha (TNF-α) and increase a blood concentration of interleukin-10 (IL-10) in the subject upon electrically stimulating the splenic nerve. To reduce inflammation in the subject, the device can be configured to electrically stimulate the splenic nerve with a plurality of electrical pulses emitted at a frequency of less than 25 Hz, such as about 3 Hz to about 20 Hz. The device can be configured to electrically stimulate the splenic nerve using a plurality of biphasic electrical pulses comprising an cathodal phase followed by an anodal phase.

The device can be configured to electrically stimulate the splenic nerve using one or more biphasic electrical pulses. The device can be configured to electrically stimulate the splenic nerve using a pulse train comprising a plurality of biphasic electrical pulses. The device can be configured to electrically stimulate the splenic nerve using biphasic electrical pulses comprising an anodal phase followed by a cathodal phase for increasing inflammation in the subject, such as for increasing a blood concentration of an inflammatory cytokine in the subject, e.g. for treating cancer. The device can be configured to electrically stimulate the splenic nerve using biphasic electrical pulses comprising a cathodal phase followed by an anodal phase for reducing inflammation in the subject, e.g. for treating cancer. Preferably, the device is configured to electrically stimulate the splenic nerve using the biphasic electrical pulses having a duration of 400 µs or less, such as 300 µs or less, preferably about 200 µs. The device can be configured such that a duration of the biphasic electrical pulse is split evenly between the cathodal and anodal phases. The device can be configured such that the biphasic electrical pulse comprises an inter-phase interval between the anodal phase and cathodal phase. The inter-phase interval preferably has a duration of 10 to 100 µs, such as 30-70 µs, such as 50-60 µs. The biphasic pulses can be biphasic square-wave pulses.

The implantable device can comprise two or more electrodes configured to be in electrical communication with a splenic nerve of a subject; a nerve cuff configured to at least partially wrap around the splenic nerve or a splenic neurovascular bundle; and an integrated circuit configured to operate the two or more electrodes to emit a plurality of electrical pulses in a predetermined pattern associated with treating cancer in a subject when the plurality of electrical pulses in said predetermined pattern are used to stimulate the splenic nerve of the subject. The predetermined pattern can be associated with causing an increase in the circulation or activation of NK cells or cytotoxic T cells in a subject when the plurality of electrical pulses in said predetermined pattern are used to stimulate the splenic nerve of the subject. The predetermined pattern can be associated with causing an increase in the circulation or activation of NK cells in a subject when the plurality of electrical pulses in said predetermined pattern are used to stimulate the splenic nerve of the subject. The predetermined pattern can be associated with causing a decrease in the circulation of cytotoxic T cells in a subject when the plurality of electrical pulses in said predetermined pattern are used to stimulate the splenic nerve of the subject. The predetermined pattern can be associated with causing an increase in the circulation or activation of NK cells and decrease in the circulation of cytotoxic T cells in a subject when the plurality of electrical pulses in said predetermined pattern are used to stimulate the splenic nerve of the subject.

The predetermined pattern can be associated with causing an increase in a blood concentration of an inflammatory cytokine (e.g., a pro-inflammatory cytokine or an anti-inflammatory cytokine) in a subject when the plurality of electrical pulses in said predetermined pattern are used to stimulate the splenic nerve of the subject.

The predetermined pattern is associated with causing a decrease in a blood concentration of an inflammatory cytokine (e.g., a pro-inflammatory cytokine or an anti-inflammatory cytokine) in a subject when the plurality of electrical pulses in said predetermined pattern are used to stimulate the splenic nerve of the subject.

The predetermined pattern can be associated with causing increased inflammation in a subject when the plurality of electrical pulses in said predetermined pattern are used to stimulate the splenic nerve of the subject. The predetermined pattern can be associated with causing an increase in a blood concentration of a pro-inflammatory cytokine and/or a decrease in a blood concentration of an anti-inflammatory cytokine in a subject when the plurality of electrical pulses in said predetermined pattern are used to stimulate the splenic nerve of the subject.

The predetermined pattern can be associated with causing decreased inflammation in a subject when the plurality of electrical pulses in said predetermined pattern are used to stimulate the splenic nerve of the subject. The predetermined pattern can be associated with causing an increase in a blood concentration of an anti-inflammatory cytokine and/or a decrease in a blood concentration of a pro-inflammatory cytokine in a subject when the plurality of electrical pulses in said predetermined pattern are used to stimulate the splenic nerve of the subject.

The controller if the above implantable device can be configured to select a mode of operation from a plurality of operation modes comprising: a first mode of operation that provides a plurality of electrical pulses in a predetermined inflammatory pattern associated with causing increased inflammation in a subject when the plurality of electrical pulses in said predetermined inflammatory pattern are used to stimulate the splenic nerve of the subject; and a second mode of operation that provides a plurality of electrical pulses in a predetermined anti-inflammatory pattern associated with causing decreased inflammation in a subject when the plurality of electrical pulses in said predetermined inflammatory pattern are used to stimulate the splenic nerve of the subject. The mode of operation may be selected based on a trigger signal. The trigger signal may be based on splenic nerve activity. The implantable device can include a wireless communication system, and be configured to wirelessly receive the trigger signal.

The device can comprise an ultrasonic transducer configured to receive ultrasonic waves; and convert energy from the ultrasonic waves into electrical energy that powers the device.

The device can be configured to electrically stimulate the splenic nerve using one or more electrical pulses about 1 ms in length or less.

The device can be configured to electrically stimulate the splenic nerve using one or more electrical pulses having an amplitude of about 250 µA to about 10 mA.

The device can be configured to electrically stimulate the splenic nerve using one or more electrical pulses at a frequency of about 100 Hz or less.

The device can be configured to electrically stimulate the splenic nerve using a pulse train comprising a plurality of biphasic electrical pulses. The plurality of biphasic electrical pulses can comprise an anodal phase followed by a cathodal phase. The plurality of biphasic electrical pulses can comprise a cathodal phase followed by an anodal phase.

The device can be configured to electrically stimulate the splenic nerve using a plurality of pulse trains comprising two or more electrical pulses, the pulse trains separated by a dwell time of about 50 ms or more, such as about 50 ms to about 2 minutes, or about 500 ms or more. The device can be configured to wirelessly receive power, such as though ultrasonic waves, during the dwell time.

The device can be configured to provide a plurality of pulse trains comprising at least a first pulse train followed by a second pulse train, wherein electrical pulses in the first pulse train have an amplitude lower than an amplitude of electrical pulses in the second pulse train.

In any one of the above devices, the splenic nerve can be electrically stimulated using tonic electrical pulses.

In any of the above devices, the device can further comprise a nerve cuff configured to position at least one of the two or more electrodes in electrical communication with the splenic nerve. The nerve cuff can be a helical nerve cuff configured to at least partially wrap around the splenic neurovascular bundle.

In any of the above devices, the device can further comprise a wireless communication system. The device can include, for example as part of the wireless communication system, an ultrasonic transducer configured to receive ultrasonic waves; and convert energy from the ultrasonic waves into electrical energy that powers the device.

In any one of the above devices, the device can be configured to electrically stimulate the splenic nerve in response to a trigger signal. The trigger signal can be encoded in ultrasonic waves received by the device. The trigger signal can be based on splenic nerve activity. The trigger signal can be based on a deviation from a baseline splenic nerve activity. The trigger signal can be based on a measured physiological condition. The device can further comprises a sensor configured to measure a physiological condition. The physiological condition can be a temperature, a pulse rate, or a blood pressure.

In any one of the above devices, the device can be configured to monitor splenic nerve activity.

In s any one of the above devices, the device can be configured to emit backscatter waves (e.g., ultrasonic backscatter waves) encoding information related to the splenic nerve activity or the physiological condition. The backscatter waves encoding the information related to the splenic nerve activity or the physiological condition can be configured to be received by an external device. The backscatter waves can further encode information related to the status of the device or one or more electrical pulses emitted by the device.

In any one of the above devices, the implanted device can have a volume of about 5 mm$^3$ or smaller.

Further provided is a system, comprising the any one of the above devices and an interrogator comprising a wireless communication system configured to wirelessly communication or power the device.

BRIEF DESCRIPTION OF THE DRAWINGS

FIG. 5C shows a cross-sectional view of a device with a housing attached to a nerve cuff. Feedthroughs attached to the housing electrically connect electrodes on the nerve cuff to the board assembly contained within the housing.

FIG. 6A shows an exemplary helical nerve cuff in a flexed configuration, wherein the helical portions are partially unwound. FIG. 6B shows the helical nerve cuff in FIG. 6B in a relaxed configuration, with the helical portions wound after recoiling from the flexed configuration.

FIGS. 22A-22C show results of a mouse tumor growth study in which animals received an active chronic splenic nerve implant (Stim, n=11), an inactive chronic splenic nerve implant (Sham, n=14), or no implant (Control, n=34). All animals were implanted with CT26 colon tumors in their right flank which was measured every day. The splenic nerves of Stim animals were stimulated daily with a train of cathodal-first, biphasic, square wave pulses (duration of 300 µs split evenly between cathodal and anodal phases, with a 60 µs inter-phase interval) at a frequency of 5 pulses per second (5 Hz) and at an amplitude of 1.8 mA. Sham animals were handled similarly to Stim animals but were not stimulated electrically. Control animals were not handled. FIG. 22A shows average tumor volumes in each group for each day individually. Asterisks indicate days in which Stim animals had significantly lower tumor volumes than Sham animals. FIG. 22B shows the exponential curve fit for each group using tumor volumes for all days. FIG. 22C shows the 95% confidence intervals for the exponential curve fits.

FIG. 25A shows circulating NK cell levels (as a percentage of total lymphocytes) for each patient normalized to the concentration measured at the pre-stimulation time point. FIG. 25B-25E show the total counts of IFN-γ positive (FIG. 25B), TNF-α positive (FIG. 25C), MIP-1b positive (FIG. 25D), and CD107a positive (FIG. 25E) NK cells, respectively, following splenic nerve stimulation. These markers are expressed by NK cells in the active state. These levels were determined by multiplying the proportion of NK cells in each sample by the proportion of NK cells expressing the given marker. Values for each subject were normalized to the values at the pre-stimulation time point. Asterisks signify P<0.05 compared to the pre-stimulation time point for the group data. Splenic nerve stimulation was effective at increasing the fraction of NK cells in blood as well as the total number of NK cells expressing activation markers.

DETAILED DESCRIPTION

Figure 1:
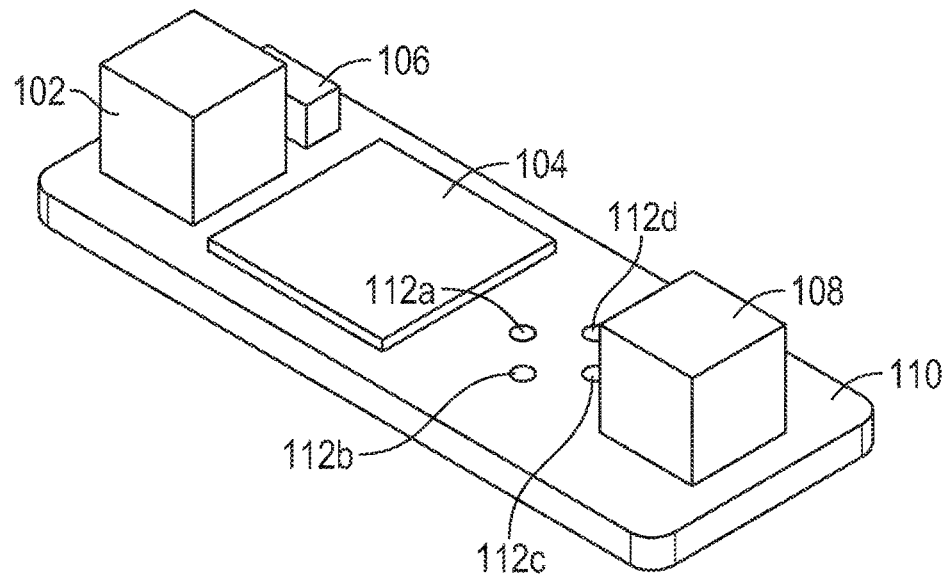
FIG. 1 shows an exemplary board assembly for an implantable device body, which may be enclosed in a housing and attached to a nerve cuff.

Described herein are methods of modulating the immune system of a subject with cancer, and methods of treating cancer, using an implanted device configured to electrically stimulate the splenic nerve. Further described are implantable devices for use in such methods, and systems that include one or more implantable devices and an interrogator configured to wirelessly communicate with the one or more implantable devices.

An implantable device configured to modulate the body's immune system while limiting off target effects can be used to control the inflammatory state of a cancer patient for effective cancer treatment. The splenic nerve leads to the spleen of the patient, and selective splenic nerve modulation by electrically stimulating the splenic nerve can increase or decrease activation of immune cells (such as natural killer (NK) cells and/or cytotoxic T-cells) in the spleen, or increase or decrease the blood concentration of one or more pro- or anti-inflammatory cytokines or chemokines, and thus the inflammatory state of the subject. For example, a method of modulating the immune system of a subject with a cancer can include electrically stimulating the splenic nerve of the subject using a fully implanted device comprising one or more electrodes in electrical communication with the splenic nerve, thereby modulating the immune system of the subject. A method of treating a cancer in a subject can include electrically stimulating the splenic nerve of the subject using a fully implanted device comprising one or more electrodes in electrical communication with the splenic nerve, thereby modulating the immune system of the subject and treating the cancer in the subject.

Electrically stimulating the splenic nerve can result in the activation or deactivation of immune cells, such as natural killer (NK) cells or cytotoxic T-cells. For example, the splenic nerve can be electrically stimulated to increase circulation of NK cells, decrease circulation of cytotoxic T cells, or both simultaneously. The blood concentration of pro-inflammatory or anti-inflammatory cytokines may also be controlled by electrically stimulating the splenic nerve. Activated NK cells and cytotoxic T-cells, and certain cytokines, play significant roles in killing cancer cells throughout the body. Certain cancer types are more responsive to an increased inflammatory environment, while other cancer types are more responsive to a lower inflammatory environment. Further, a decreased inflammatory environment may be useful, for example, to control pain, fever, non-cancerous tissue necrosis, shock or other conditions in the subject with cancer.

Selective electrical stimulation of the splenic nerve can modulate the immune system in a manner dependent on how the splenic nerve is stimulated. For example, as further described herein, stimulating the splenic nerve using certain electric pulse parameters can result in increased inflammation (for example, an increase in the blood concentration of pro-inflammatory cytokines (such a TNF-α, IL-6, and/or IL-1β) and/or a decrease in the blood concentration of anti-inflammatory cytokines (such as IL-10)). Inflammation may be increased, for example, using higher frequency electrical pulse (such as at a frequency of about 25 Hz or more, such as about 30 Hz or more, or about 30 Hz to about 100 Hz) and/or stimulating the splenic nerve using a plurality of anodal-first, biphasic electrical pulses. Stimulating the splenic nerve using certain other electric pulse parameters can result in decreased inflammation (for example, a decrease in the blood concentration of pro-inflammatory cytokines (such a TNF-α, IL-6, and/or IL-1β) and/or an increase in the blood concentration of anti-inflammatory cytokines (such as IL-10)). Inflammation may be decreased, for example, using lower frequency electrical pulse (such as at a frequency of less than 25 Hz, such as about 1 Hz to about 20 Hz, or about 3 Hz to about 20 Hz) and/or stimulating the splenic nerve using a plurality of cathodal-first, biphasic electrical pulses. Increased circulation and/or activation of immune cells (such as NK cells) can also results from electrically stimulating the splenic nerve, either with increased or with decreased inflammation in the subject.

The implantable device includes two or more electrodes configured to be in electrical communication with the splenic nerve. The implantable device, in ues, may be fully implanted in the subject such that two or more electrodes are in electrical communication with the splenic nerve. The device can be configured to provide a plurality of electrical pulses to the splenic nerve to electrically stimulate the splenic nerve. For example, the device can be configured to provide a plurality of electrical pulses using at least one of the two or more electrodes, according to a predetermined pattern associated with treating cancer in a subject, increasing inflammation in a subject, or decreasing inflammation in a subject (or both treating cancer and increasing inflammation, or treating cancer and decreasing inflammation). In certain exemplary configurations, the device can include a controller that can select a mode of operation of the device (for example, between a first mode the causes increased inflammation and a second mode that causes decreased inflammation).

Because the abdominal cavity has limited space for an implantable device, the device can be designed for reduced size. An effective method for providing power to the implantable device includes the transmission of ultrasonic waves. For example, the device can be arranged to receive ultrasonic waves from an external ultrasonic transducer; and to convert energy from the ultrasonic waves into electrical energy that powers the device. Ultrasonic waves may also be used to transmit information to or from the implantable device. For example, the ultrasonic waves received by the implantable device may encode a trigger signal that provides information related to when and/or how to stimulate the splenic nerve. The implantable device can be arranged to detect an electrical signal transmitted by the splenic nerve. The implantable device may then emit an ultrasonic backscatter that encodes information related to the detected electrical signal, or the implantable device may generate the trigger signal itself based on the detected electrical signal.

The device can include a body having a wireless communication system (such as one or more ultrasonic transducers or one or more radiofrequency antennas), and two or more electrodes in electrical communication with the ultrasonic transducer, and configured to electrically stimulate the splenic nerve and/or detect an electrical signal transmitted by the splenic nerve. The implantable device optionally includes a nerve cuff attached to the body. The splenic nerve cuff is sized and configured to attach the device to the splenic nerve or splenic neurovascular bundle, and position the electrodes in electrical communication with the splenic nerve.

For wireless implanted neurostimulation devices, energy efficiency is given some consideration. Wireless power delivery is limited by safety concerns for tissue heating that can cause irreversible damage to a subject. Furthermore, high levels of charge injection through stimulation electrodes can result in water electrolysis and damage to the electrode materials. Thus, stimulation pulse parameters configured to achieve the greatest activation of neural tissue using the smallest amount of charge is generally preferred. For example, in some embodiments, the stimulatory electrical pulse is less than 1 ms in length (for example, about 100 μs to about 400 μs in length). Pulses of this length can effectively modulate (i.e., increase or decrease) cytokine levels or immune cell activation in the subject. The implantable device may stimulate the splenic nerve to effectively modulate levels in the subject, while efficiently releasing charge to stimulate the tissue. Modulation of the cytokine level or immune cell activation allows for inflammatory state control in the patient, with is useful for cancer treatment.

For some implantable devices, scenarios may exist where the energy demands of stimulation deplete the energy storage device before it can be sufficiently recharged in order to deliver the next stimulation pulse. For these situations, it may not be desirable to continuously apply electrical pulses to the tissue. It has been found that effective modulation of cytokine levels in the subject can be achieved by applying a pulse train comprising two or more electrical pulses, wherein pulse trains are separated by a dwell time. The dwell time allows the device time to recharge, but still effectively modulate the immune system.

The implantable device is configured to be implanted in a subject, which may be a mammal. In some embodiments, the subject is a human, dog, cat, horse, cow, pig, sheep, goat, monkey, or a rodent (such as a rat or mouse).

Although the methods provided herein are described using an implanted medical device with a wireless communication system, it is contemplated that the immune system modulation methods may be performed using other suitable devices, which may or may not be fully implanted. Nevertheless, the described implantable device is particularly well-suited for implementing the described immune system modulation methods.

Definitions

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The term "physiological condition" refers to a physiological state or parameters or values estimated or measured within a physiological environment. Accordingly, a "physiological condition" can include a temperature. pH, $pO_2$, heart rate, respiratory rate, presence or absence of an analyte, an amount of an analyte, a strain, or any other value measured within a physiological environment.

The term "subject" and "patient" are used interchangeably herein to refer to a vertebrate animal.

The terms "treat," "treating," "treatment," and "therapy" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

Immune System Modulation and Cancer Treatment

The immune system of a subject a subject with cancer can be modulated, for example by activating immune cells (for example, natural killer (NK) cells and/or cytotoxic T-cells) within the subject, or by modulating (e.g., increasing or decreasing) the blood concentration of certain pro-inflammatory or anti-inflammatory cytokines, such as one or more of tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), and/or RANTES, among others. The immune system may be modulated, for example, to treat the cancer in the subject (such as by increasing or decreasing the blood concentration of one or more pro-inflammatory cytokines, or by activating and/or increasing circulation of certain immune cells, such as NK cells and/or cytotoxic T-cells, that can kill the cancer cells). In some examples, the immune system can be modulated to treat the cancer in the subject by activating and/or increasing circulation of NK cells and decreasing circulation of cytotoxic T cells. The immune system can be modulated to reduce one or more adverse symptoms associated with the cancer, cancer treatment and/or inflammation (for example, by decreasing the blood concentration of one or more pro-inflammatory cytokines).

The cancer of the patient may be any of any type, for example (but not limited to), a head and neck cancer, a pancreatic cancer, a breast cancer, a glial cancer, an ovarian cancer, a cervical cancer, a gastric cancer, a skin cancer, a colon cancer, a rectal cancer, a lung cancer, a kidney cancer, or a thyroid cancer. Because the implantable device modulates the systemic immune response, the implantable device can stimulate the splenic nerve to treat the cancer without being in close proximity to the cancer. The cancer can be an unresectable cancer or a borderline unresectable cancer. For example, the cancer may not be removable by surgery because of the tumor's location within the body, or may not be treatable by targeted radiation because of surrounding critical tissue. By systemically modulating the immune system, the cancer may be treated using native anti-cancer systems.

Exemplary cytokines or chemokines that may be modulated (i.e., increased or decreased blood concentration) using the methods described herein include one or more of IL-1α, IL-1β, IL-2, IL-4, IL-5, IL-6, IL-7, IL-10, IL-12, IL-13, IL-17A, IL-18, M-CSF, MCP-1, MIP-1α, MIP-3α, RANTES, TNF-α, VEGF, G-CSF, GM-CSF, GRO/KC, and IFN-γ.

The splenic nerve of the subject can be electrically stimulated to modulate the immune system, for example through the use of an implantable medical device described herein. The implantable medical device described includes two or more electrodes that are in electrical communication with the splenic nerve of the subject, and can optionally include a wireless communication system (e.g., an ultrasonic transducer) that is configured to receive energy waves (such as ultrasonic waves) that power and operate the implantable device. The implantable device may receive ultrasonic waves, for example from an external ultrasonic transducer (e.g., an interrogator), and convert energy from the ultrasonic waves into an electrical energy that powers the implanted medical device.

The implantable medical device may be fully implanted in the subject in a position to electrically stimulate the splenic nerve (i.e., such that electrodes of the device are in electrical communication with the splenic nerve). The device can, for example, fully implanted in the perivascular fascia surrounding the splenic nerve and splenic artery. The splenic nerve need not be separated from the splenic artery. As further described herein, the implantable device may include a nerve cuff that is sized and configured to attach the device to the splenic nerve or a splenic neurovascular bundle (which includes both the splenic nerve and the splenic artery) and position the one or more electrodes of the device in electrical communication with the splenic nerve.

Electrical stimulation of the splenic nerve can modulate the immune system by modulating (such as reducing or increasing) activity of immune cells (such as natural killer (NK) cells or cytotoxic T-cells) residing in or passing through the spleen, and/or the release of certain cytokines, which may be pro-inflammatory or anti-inflammatory, such as tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), and/or RANTES. The electrical signal may, for example, induce a neurological signal or block a neurological signal transmitted by the splenic nerve, which alters splenic function.

The methods and devices described herein may be used to treat a cancer in a patient. Electrical stimulation of the splenic nerve can result in the activation of certain immune cells, such as NK cells and/or cytotoxic T cells, and/or an increase in the blood concentration of one or more pro-inflammatory cytokines (such as TNF-α, IL-6, or IL-1β) useful in the treatment of cancer. Electrical stimulation of the splenic nerve can result in the activation and/or increased circulation of NK cells and/or decreased circulation of cytotoxic T cells, and/or an increase and/or decrease in the blood concentration of one or more pro-inflammatory cytokines (such as TNF-α, IL-6, or IL-1β) and/or an anti-inflammatory cytokine (such as IL-10) useful in the treatment of cancer.

In an example, the cancer is treated by electrically stimulating the splenic nerve in combination with one or more additional cancer therapies, such as the administration of one or more anti-cancer drugs. The anti-cancer drug may be, for example, a small molecule drug or a biologic drug (such as an antibody or antibody fragment). Exemplary anti-cancer drugs that may be administered in combination with electrically stimulating the splenic nerve include, but are not limited to, abiraterone, bevacizumab, bortezomib, carboplatin, cisplatin, cyclophosphamide, denosumab, docetaxel, doxorubicin, enzalutamide, erlotinib, etoposide, everoliums, fluorouracil (5-FU), gemcitabine, ibrutinib, imatinib, methotrexate, nivolumab, nilotinib, paclitaxel, palbociclib, pebrolizumab, pemtetrexed, pertuzumab, rituximab, ruxolitinib, and trastuzumab, among others.

The direction of immune system modulation (i.e., increase or decrease of cytokine release and/or immune cell (e.g., NK cell and/or cytotoxic T-cell) activation) can depend on the amount of charge delivered to the splenic nerve (for example, as controlled by pulse length, pulse frequency, and/or current amplitude) and/or polarity of the pulse (or polarity sequence, for a biphasic pulse). For example, a small amount of charge delivered to the splenic nerve can decrease cytokine (e.g., TNF-α) blood levels and/or NK cell activation, whereas a larger amount of charge delivered to the splenic nerve may increase cytokine (e.g., TNF-α) blood levels and/or NK cell activation in the subject. The polarity, such as cathodal or anodal, of the pulse (or sequence of polarity of the pulse in a biphasic pulse, such as cathodal-first or anodal-first), can also impact the evoked response of the splenic nerve thereby altering the efficiency (and impact) of the delivered charge. For example, a cathodal-first, biphasic pulse administered to the splenic nerve requires increased pulse amplitude to obtain the same evoked response as an anodal-first biphasic pulse administered to the splenic nerve.

One or more adverse symptoms associated with cancer, cancer treatment, or inflammation may be reduced by decreasing the blood concentration of certain inflammatory cytokines (such as TNF-α, IL-6, and/or IL-β). Exemplary adverse symptoms can include pain, fever, non-cancerous tissue necrosis, and shock. For example, the electrical signal to the splenic nerve can cause increased noradrenaline release, which stimulates T-cells within the spleen to increase acetylcholine release. The acetylcholine signals downregulation of TNF-α and IL-6 release by splenic macrophages, thereby reducing inflammation in the subject. Modulation of the immune system can allow for reducing inflammation in the subject, reducing the release of an inflammatory cytokine in the subject, or reducing the concentration of an inflammatory cytokine in the subject.

Increase or reduction of inflammation can be determined using known methods, such as a reduction of swelling in a joint, decreased pain or discomfort reported by the subject, a change in a radiology-based score of inflammation, a reversal of bone or tissue damage caused by inflammation, or by measuring one or more blood markers, such as a cytokine concentration. Cytokines in the blood can be measured by known methods, such as an enzyme-linked immunosorbent assay (ELISA), mass spectrometry, or any other suitable method.

Immune cell activation (e.g., NK cell activation or cytotoxic T-cell activation) and/or circulation can be measured using known methods, such as by detecting one or more activation markers (for example, by using flow cytometry (such as fluorescence-activated cell sorting (FACS)), immunoblotting, ELISA, or other known methods) or a cell-mediated cytotoxicity assay.

To electrically stimulate the splenic nerve, an implanted device emits one or more electrical pulses. The one or more electrical pulses emitted by the device can include one or more direct current pulses or one or more alternating current pulses. The one or more electrical pulses emitted by the device can include one or more constant voltage pulses. The two or more electrical pulses can be separated by a dwell time. The device can be configured to emit a plurality of electrical pulses in a pulse train, and pulse trains can be separated by a dwell time.

The electrical stimulation of the splenic nerve can be configured to increase or decrease the immune response. For example, the electrical stimulation can be configured to increase a level of activated immune cells (such as active NK cells and/or cytotoxic T-cells) in the subject. The electrical stimulation can be configured to decrease a level of activated immune cells (such as active NK cells and/or cytotoxic T-cells) in the subject. The electrical stimulation can be configured to increase the blood concentration of one or more pro-inflammatory cytokines. The electrical stimulation can be configured to increase the blood concentration of one or more of IL-12, IL-13, IL-17A, IL-18, M-CSF, MCP-1, MIP-1α, MIP-3α, RANTES, TNF-α, VEGF, G-CSF, GM-CSF, GRO/KC, IFN-γ, IL-1α, IL-1β, IL-2, IL-4, IL-5, IL-6, IL-7, and IL-10. The electrical stimulation can be configured to decrease the blood concentration of one or more pro-inflammatory cytokines. The electrical stimulation can be configured to decrease the blood concentration of one or more of IL-12, IL-13, IL-17A, IL-18, M-CSF, MCP-1, MIP-1a, MIP-3α, RANTES, TNF-α, VEGF, G-CSF, GM-CSF, GRO/KC, IFN-γ, IL-1α, IL-1β, IL-2, IL-4, IL-5, IL-6, IL-7, and IL-10.

By way of example, the electrical stimulation may be configured to decrease the activation of NK cells and/or cytotoxic T cells, or decrease the level of one or more pro-inflammatory cytokines, or increase the level of one or more anti-inflammatory cytokines using a lower frequency electrical pulse (such as a frequency lower than about 25 Hz, or lower than about 20 Hz, such as about 0.1 Hz to about 20 Hz, about 0.1 Hz to about 15 Hz, or about 3 Hz to about 20 Hz). Stimulation may be tonic, or may include a plurality of pulse trains. By way of example, tonic stimulation may last for about 30 seconds to about 30 minutes (such as about 30 seconds to about 1 minutes, about 1 minute to about 2 minutes, about 2 minutes to about 5 minutes, about 5 minutes to about 10 minutes, about 10 minutes to about 20 minutes, or about 20 minutes to about 30 minutes). A pulse train may include, for example, about 5 or more pulses, or about 5 to about 50 pulse trains (such as about 5 to about 10, about 10 to about 15, about 15 to about 20, about 20 to about 30, about 30 to about 40, or about 40 to about 50 pulses), and the pulse trains may be separated by a dwell time. The dwell time separating pulse trains may be the same between pulse trains, or may be different between pulse trains. The pulse trains may have the same pulse parameters or different pulse parameters. For example, the amplitude of the pulses between the pulse trains may be different (i.e., pulses in a first pulse train have a first amplitude, and pulses in a second pulse train have a second amplitude). The amplitude of the pulses in a pulse train can be higher than the amplitude of the pulse in a prior pulse train (e.g. the immediately prior pulse train) during the duration of stimulation. The amplitude of pulses in a pulse train may increase by a predetermined amount compared to the amplitude of pulses in an immediately prior pulse train. The duration of pulse trains may last for about 30 seconds to about 30 minutes (such as about 30 seconds to about 1 minutes, about 1 minute to about 2 minutes, about 2 minutes to about 5 minutes, about 5 minutes to about 10 minutes, about 10 minutes to about 20 minutes, or about 20 minutes to about 30 minutes). The electrical pulses used to increase inflammation may include a plurality of anodal-first, biphasic electrical pulses.

In another example, the electrical stimulation may be configured to increase the activation of NK cells and/or cytotoxic T cells, or increase the level of one or more pro-inflammatory cytokines, and/or decrease the level of one or more anti-inflammatory cytokines using a higher frequency electrical pulse (such as a frequency higher than about 20 Hz, such as between about 20 Hz and about 1 kHz, or higher than about 25 Hz, such as between about 30 Hz and about 1 kHz, or about 30 Hz to about 100 Hz). Electrical stimulation may be tonic, and may last, for example, between about 30 seconds to about 30 minutes (such as about 30 seconds to about 1 minutes, about 1 minute to about 2 minutes, about 2 minutes to about 5 minutes, about 5 minutes to about 10 minutes, about 10 minutes to about 20 minutes, or about 20 minutes to about 30 minutes). The electrical pulses used to increase inflammation may include a plurality of cathodal-first, biphasic electrical pulses.

The pattern of the electrical pulses emitted by the implantable device may be predetermined pulse patterns. The predetermined patterns may be stored in a memory on the device, or may be communicated to the implantable device. The predetermined pattern of electrical pulses includes parameters of the electrical pulse (e.g., one or more of frequency, pulse shape, amplitude, length, etc.) that are associated with the desired effect.

For example, the predetermined pattern may be associated with treating cancer in the subject when the plurality of electrical pulses in said predetermined pattern are used to stimulate the splenic nerve of the subject. For example, the predetermined pattern may be associated with increased circulation and/or activation of natural killer cells.

The predetermined pattern may be associated with treating cancer and increasing the circulation or activation of natural killer cells in the subject when the plurality of electrical pulses in said predetermined pattern are used to stimulate the splenic nerve of the subject.

The predetermined pattern may be associated with treating cancer and increasing inflammation (e.g., increasing the blood concentration of one or more pro-inflammatory cytokines (such as TNF-α, IL-6, and/or IL-1β) and/or decreasing the blood concentration of one or more anti-inflammatory cytokines (such as IL-10)) in the subject when the plurality of electrical pulses in said predetermined pattern are used to stimulate the splenic nerve of the subject.

The predetermined pattern may be associated with treating cancer, increasing the activation and/or circulation of natural killer cells, and increasing inflammation (e.g., increasing the blood concentration of one or more pro-inflammatory cytokines (such as TNF-α, IL-6, and/or IL-1β) and/or decreasing the blood concentration of one or more anti-inflammatory cytokines (such as IL-10)) in the subject when the plurality of electrical pulses in said predetermined pattern are used to stimulate the splenic nerve of the subject.

The predetermined pattern may be associated with treating cancer and decreasing inflammation (e.g., decreasing the blood concentration of one or more pro-inflammatory cytokines (such as TNF-α, IL-6, and/or IL-1β) and/or increasing the blood concentration of one or more anti-inflammatory cytokines (such as IL-10)) in the subject when the plurality of electrical pulses in said predetermined pattern are used to stimulate the splenic nerve of the subject.

The predetermined pattern may be associated with treating cancer, increasing the activation and/or circulation of natural killer cells, and decreasing inflammation (e.g., decreasing the blood concentration of one or more pro-inflammatory cytokines (such as TNF-α, IL-6, and/or IL-1β) and/or increasing the blood concentration of one or more anti-inflammatory cytokines (such as IL-10)) in the subject when the plurality of electrical pulses in said predetermined pattern are used to stimulate the splenic nerve of the subject.

The implantable device may include an integrated circuit that can select a mode of operation from a plurality of operation modes. For example, the plurality of operation modes may include a pro-inflammatory mode, which provides a plurality of electrical pulses in a predetermined inflammatory pattern associated with causing increased inflammation in a subject when the plurality of electrical pulses in said predetermined inflammatory pattern are used to stimulate the splenic nerve of the subject; and an anti-inflammatory mode, which provides a plurality of electrical pulses in a predetermined anti-inflammatory pattern associated with causing decreased inflammation in a subject when the plurality of electrical pulses in said predetermined inflammatory pattern are used to stimulate the splenic nerve of the subject. The integrated circuit may select the mode of operation based on a trigger signal. The trigger signal can signal to the implantable device, for example, to enter into a pro-inflammatory mode to cause increased inflammation if a lower than desirable inflammatory state is detected. Or the trigger signal may signal to the implantable device to enter into an anti-inflammatory mode to cause decreased inflammation if a higher than desirable inflammatory state is detected. The inflammatory state may be detected by the implantable device itself, for example based on splenic nerve activity and/or other physiological condition. Or the inflammatory state may be detected by a different device, which can communicate the trigger signal to the implantable device either directly or indirectly (i.e., through one or more intermediary devices).

The electrical pulse can be about 1 microsecond (μs) or longer (such as about 5 μs or longer, about 10 μs or longer, about 20 μs or longer, about 50 μs or longer, about 100 μs or longer, about 150 μs or longer, about 250 μs or longer, about 500 μs or longer, about 1 millisecond (ms) or longer, about 5 ms or longer, about 10 ms or longer, about 25 ms or longer, about 50 ms or longer, about 100 ms or longer, about 200 ms or longer, or about 500 ms or longer). The one or more electrical pulses can be about 1000 ms or shorter (such as about 500 ms or shorter, about 200 ms or shorter, about 100 ms or shorter, or about 50 ms or shorter, about 25 ms or shorter, about 10 ms or shorter, about 5 ms or shorter, about 1 ms or shorter, about 500 μs or shorter, about 250 μs or shorter, about 150 μs or shorter, about 100 μs or shorter, about 50 μs or shorter, about 20 μs or shorter, about 10 μs or shorter, or about 5 μs or shorter). The one or more electrical pulses can be less than 1 ms in length, such as about 50 μs to about 450 μs in length, about 100 μs to about 400 μs in length, or about 200 μs to about 400 μs in length.

The dwell time between electrical pulses (i.e., an inter-pulse interval) can be about 1 microsecond (μs) or longer (such as about 5 μs or longer, about 10 μs or longer, about 20 μs or longer, about 50 μs or longer, about 100 μs or longer, about 250 μs or longer, about 500 μs or longer, about 1 millisecond (ms) or longer, about 5 ms or longer, about 10 ms or longer, about 25 ms or longer, or about 50 ms or longer). The dwell time can be about 100 ms or shorter (such as about 50 ms or shorter, about 25 ms or shorter, about 10 ms or shorter, about 5 ms or shorter, about 1 ms or shorter, about 500 μs or shorter, about 250 μs or shorter, about 100 μs or shorter, about 50 μs or shorter, about 20 μs or shorter, about 10 μs or shorter, or about 5 μs or shorter).

The one or more electrical pulses can be about 1 microamp (μA) or more (such as about 5 μA or more, about 10 μA or more, about 25 μA or more, about 50 μA or more, about 100 μA or more, about 250 μA or more, about 500 μA or more, about 1 milliamp (mA) or more, about 5 mA or more, about 10 mA or more, or about 25 mA or more). The one or more electrical pulses can be about 50 mA or less (such as about 25 mA or less, about 10 mA or less, about 5 mA or less, about 1 mA or less, about 500 µA or less, about 250 µA or less, about 100 µA or less, about 50 µA or less, about 25 µA or less, about 10 µA or less, about 5 µA or less, or about 1 µA or less. By way of example, the amplitude of the one or more electrical pulses can be about 500 µA to about 10 mA (such as about 750 µA to about 5 mA, or about 1 mA to about 1.8 mA).

The one or more electrical pulses can have a frequency of about 0.1 Hz or more (such as about 0.5 Hz or more, about 1 Hz or more, about 3 Hz or more, about 5 Hz or more, about 10 Hz or more, about 25 Hz or more, about 30 Hz or more about 50 Hz or more, about 100 Hz or more, about 200 Hz or more, about 300 Hz or more, about 400 Hz or more, about 500 Hz or more about 600 Hz or more, about 700 Hz or more, about 800 Hz or more, about 1 kHz or more, about 2 kHz or more, or about 5 kHz or more). The one or more electrical pulses can have a frequency of about 10 kHz or less (such as about 5 kHz or less, about 2 kHz or less, about 1 kHz or less, about 800 Hz or less, about 700 Hz or less, about 600 Hz or less, about 500 Hz or less, about 400 Hz or less, about 300 Hz or less, about 200 Hz or less, about 100 Hz or less, about 50 Hz or less, about 30 Hz or less, about 25 Hz or less, about 10 Hz or less, about 5 Hz or less, about 3 Hz or less, about 1 Hz or less, or about 0.5 Hz or less).

The implanted device can be configured to generate a voltage pulse in the splenic nerve. The voltage can about 50 mV or more (such as about 100 mV or more, about 250 mV or more, about 500 mV or more about 1 V or more, about 2.5 V or more, about 5 V or more, or about 10 V or more). The voltage can be about 20 V or less (such as about 15 V or less, about 10 V or less, about 5 V or less, about 2.5 V or less, about 1 V or less, about 500 mV or less, about 250 mV or less, or about 100 mV or less).

The electrical pulses administered to the splenic nerve may be sinusoidal, square, sawtooth, or any other suitable shape. The electrical pulses may be monophasic (i.e., having only a cathodal phase or only an anodal phase) or biphasic (i.e., having both cathodal phase and anodal phase). A "biphasic pulse" as used herein refers to a single pulse with an anodal phase and a cathodal phase. The order of the cathodal phase and the anodal phase in a biphasic pulse may be in either order (i.e., anodal-first or cathodal-first). The anodal phase and the cathodal phase of the biphasic pulse may be separated by an interphase interval (for example about 10 µs to about 150 µs in length, such as about 10 µs to about 20 µs, about 20 µs to about 40 pts, about 40 µs to about 60 µs, about 60 µs to about 80 µs, about 80 µs to about 100 µs, or about 100 µs to about 150 µs in length). The interphase interval is generally short enough to allow for reversal of incidental redox reactions, long enough to allow for substantial depolarization of the nerve before the charge is reversed. The length of a biphasic pulse refers to the length of the anodal phase and the cathodal phase, and excludes the length of any optionally present interphase interval of the biphasic pulse.

The device can be configured to emit a plurality of electrical pulses in a pulse train, and pulse trains can be separated by a dwell time. The implantable device can charges the power circuit during the dwell time. For example, the device may receive wireless energy through ultrasonic or radiofrequency waves, which can be stored in a power circuit, during the dwell time. The dwell time between pulse trains can be about 50 milliseconds (ms) or longer, about 100 ms or longer, about 200 ms or longer, about 300 ms or longer, about 400 ms or longer, about 500 ms or longer about 600 ms or longer, about 700 ms or longer, about 1 second or longer, about 1.5 seconds or longer, about 2 seconds or longer, about 5 seconds or longer, or about 10 seconds or longer. The dwell time between pulse trains can be about 2 minutes or less, about 90 seconds or less, about 30 seconds or less, about 20 seconds or less, about 15 seconds or less, about 10 seconds or less, about 5 seconds or less such as about 4 seconds or less, about 3 seconds or less, about 2 seconds or less, about 1.5 seconds or less, or about 1.5 seconds or less. By way of example, the dwell time between pulse trains can be about 0.5 seconds to about 15 seconds, or any value therebetween. In another example, the dwell time between pulse trains can be between about 50 ms and about 2 minutes.

Electric pulse patterns that include dwell times between pulse trains may be particularly advantageous for implantable devices that are wirelessly powered. Because of limited space availability in the abdominal cavity, the implantable device is preferably small. Batteries are generally bulky, and it is generally preferred that the implantable device is batteryless (although in may include one or more energy storage capacitors for short term or transient energy storage). The emission of electrical pulses from the device, however, often consume substantial power. Thus, the implantable device can be configured to receive energy (for example through ultrasonic waves that power the device) during the dwell periods in between electrical pulse trains.

By way of example, the implantable device can be configured to electrically stimulate the splenic nerve using biphasic electrical pulses comprising an anodal phase followed by a cathodal phase for increasing inflammation in the subject, such as for increasing a blood concentration of an inflammatory cytokine in the subject, e.g. for treating cancer. The implantable device can be configured to electrically stimulate the splenic nerve using biphasic electrical pulses comprising a cathodal phase followed by an anodal phase for reducing inflammation in the subject, e.g. for treating cancer. Preferably, the device is configured to electrically stimulate the splenic nerve using the biphasic electrical pulses having a duration of 400 µs or less, such as 300 µs or less, preferably about 200 µs. The device can be configured such that a duration of the biphasic electrical pulse is split evenly between the cathodal and anodal phases. The device can be configured such that the biphasic electrical pulse comprises an inter-phase interval between the anodal phase and cathodal phase. The inter-phase interval preferably has a duration of 10 to 100 µs, such as 30-70 µs, such as 50-60 µs. The biphasic pulses can be biphasic square-wave pulses.

Electrical stimulation of the splenic nerve can occur in response to a trigger signal received by or generated by the implantable device. For example, the ultrasonic waves received by the implantable medical device can encode the trigger signal, which instructs the implantable medical device to electrically stimulate the splenic nerve. The trigger signal may include instructions that include a frequency, amplitude, duration, pulse pattern, pulse shape, or dwell time of the electrical pulse emitted by the implantable device. For example, the trigger signal can instruct the implantable device to stimulate the splenic nerve with a first frequency to stimulate neural activity, and a second frequency to block neural activity.

The trigger signal can be based on activity of the splenic nerve, a change in an immune system status, an increase or decrease in inflammation, or an inflammatory response. As further described herein, the implantable medical device can be configured to detect splenic nerve activity, and emit an ultrasonic backscatter that encodes information related to the splenic nerve activity. The ultrasonic backscatter can be received by an interrogator, which can decode the ultrasonic backscatter to obtain the information related to the splenic nerve activity. The information can be analyzed by the interrogator or relayed to another computer system to analyze the information. Based on the activity of the splenic nerve, the interrogator can transmit the trigger signal to the implantable medical device, instructing the device to electrically stimulate the splenic nerve. The trigger signal may be based on increase in splenic nerve activity compared to a baseline splenic nerve activity. A baseline splenic nerve activity can be established in an individual subject, for example, and the trigger signal can be based on deviations from the baseline splenic nerve activity.

The trigger signal can be based on, for example, a voltage potential change or a voltage potential change pattern measured from the splenic nerve over a period of time. The voltage change (e.g., a voltage spike) is indicative of the action potential passing through the splenic nerve, which is detected by the electrodes on the implanted device. A difference in the frequency and/or amplitude of the voltage spike (a single voltage spike or a compound voltage spike of the action potential) can indicate a change in immune activity, which may be modulated by emitting one or more electrical pulses to the splenic nerve.

The trigger system may also be based on one or more additional or alternative factors, such as a physiological condition, which may be measured by the implantable medical device or any other device or method. Exemplary physiological conditions that the trigger signal may be based on include, but are not limited to, a temperature, a blood pressure, or a pulse rate. Physiological conditions may demonstrate that the immune system should not be modulated or modulated using a different electrical pulse pattern for some reason, such as an acute illness, for example if the subject has a fever.

The trigger signal can be based on an analysis of splenic nerve activity patterns and a detected physiological condition, such as temperature, pulse, or blood pressure. The splenic nerve activity may be detected by the implantable medical device or by some other device or method.

The trigger signal can be based on information related to aggregate information (e.g., splenic nerve activity and/or physiological condition) detected over a trailing period of time, for example over a period of minutes, hours, or days. For example, the trigger can be based on information related to splenic nerve activity detected from within about 30 seconds, about 1 minute, about 5 minutes about 15 minutes, about 30 minutes, about 1 hour, about 2 hours, about 4 hours, about 8 hours, about 12 hours, about 24 hours, about 2 days, about 4 days, or about 7 days.

The implantable medical device can be operated using an interrogator, which can transmit ultrasonic waves that power and operate the implantable device. As further described herein, the interrogator is a device that includes an ultrasonic transducer that can transmit ultrasonic waves to the implantable device and/or receive ultrasonic backscatter emitted from the implantable device. The interrogator may be a device external to the subject, and can be worn by the subject. The ultrasonic waves transmitted by the interrogator can encode the trigger signal.

In an exemplary method of modulating the immune system of a subject (such as a human) with a cancer, the method includes electrically stimulating the splenic nerve of the subject using a fully implanted device comprising one or more electrodes in electrical communication with the splenic nerve, thereby modulating the immune system of the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of modulating the immune system of a subject (such as a human) with a cancer, the method includes electrically stimulating the splenic nerve of the subject using a fully implanted device comprising one or more electrodes in electrical communication with the splenic nerve, thereby activating one or more immune cells (such as natural killer cells) in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of modulating the immune system of a subject (such as a human) with a cancer, the method includes electrically stimulating the splenic nerve of the subject using a fully implanted device comprising one or more electrodes in electrical communication with the splenic nerve, thereby increasing inflammation in the subject (such as by increasing a blood concentration of one or more inflammatory cytokines (e.g., tumor necrosis factor alpha (TNF-$\alpha$), interleukin-6 (IL-6), and/or interleukin-1$\beta$ (IL-1$\beta$))) in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of modulating the immune system of a subject (such as a human) with a cancer, the method includes electrically stimulating the splenic nerve of the subject using a fully implanted device comprising one or more electrodes in electrical communication with the splenic nerve, thereby (i) activating one or more immune cells (such as natural killer cells and/or cytotoxic T-cells) in the subject, and/or (ii) increasing inflammation in the subject (such as by increasing a blood concentration of one or more inflammatory cytokines (e.g., tumor necrosis factor alpha (TNF-$\alpha$), interleukin-6 (IL-6), and/or interleukin-1$\beta$ (IL-1$\beta$)) in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of treating a cancer in a subject (such as a human), the method includes electrically stimulating the splenic nerve of the subject using a fully implanted device comprising one or more electrodes in electrical communication with the splenic nerve, thereby modulating the immune system of the subject and treating the cancer in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of treating a cancer in a subject (such as a human), the method includes electrically stimulating the splenic nerve of the subject using a fully implanted device comprising one or more electrodes in electrical communication with the splenic nerve, thereby activating one or more immune cells (such as natural killer cells) and treating the cancer in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of treating a cancer in a subject (such as a human), the method includes electrically stimulating the splenic nerve of the subject using a fully implanted device comprising one or more electrodes in electrical communication with the splenic nerve, thereby increasing inflammation in the subject (such as by increasing a blood concentration of one or more inflammatory cytokines (e.g., tumor necrosis factor alpha (TNF-α), interleukin-6 (IL-6), and/or interleukin-1β (IL-1β))) and treating the cancer in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of treating a cancer in a subject (such as a human), the method includes electrically stimulating the splenic nerve of the subject using a fully implanted device comprising one or more electrodes in electrical communication with the splenic nerve, thereby activating one or more immune cells (such as natural killer cells), increasing inflammation in the subject (such as by increasing a blood concentration of one or more inflammatory cytokines (e.g., tumor necrosis factor alpha (TNF-α), interleukin-6 (IL-6), and/or interleukin-1β (IL-1β))) and treating the cancer in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of reducing inflammation in a subject (such as a human) with cancer, the method includes electrically stimulating the splenic nerve of the subject using a fully implanted device comprising one or more electrodes in electrical communication with the splenic nerve, thereby modulating the immune system to reduce inflammation in the subject. The inflammation can be associated with pain, fever, non-cancerous tissue necrosis, or shock. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of reducing inflammation in a subject (such as a human) with cancer, the method includes electrically stimulating the splenic nerve of the subject using a fully implanted device comprising one or more electrodes in electrical communication with the splenic nerve, thereby deactivating one or more immune cells (such as natural killer cells and/or cytotoxic T-cells) in the subject. The inflammation can be associated with pain, fever, non-cancerous tissue necrosis, or shock. The method can optionally further include receiving, at the device, ultrasonic waves (for example, from an external ultrasonic transducer); and converting energy from the ultrasonic waves into electrical energy that powers the device. The splenic nerve is electrically stimulated in response to a trigger signal. The trigger signal may be, for example, encoded in ultrasonic waves received by the device or may be generated by the device itself. The trigger signal may be based on splenic nerve activity and/or a measured physiological condition (e.g., a temperature, a pulse rate, or a blood pressure). Optionally, the splenic nerve activity and/or the physiological condition is measured by the device itself.

In an exemplary method of reducing inflammation in a subject (such as a human) with cancer, the method includes electrically stimulating the splenic nerve of the subject using a fully implanted device comprising one or more electrodes in electrical communication with the splenic nerve, thereby decreasing a blood concentration of one or more inflammatory cytokines (e.g., tumor necrosis factor alpha (TNF-α), interleukin-6 (IL-6), and/or interleukin-1β (IL-1β)) in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

In an exemplary method of reducing inflammation in a subject (such as a human) with cancer, the method includes electrically stimulating the splenic nerve of the subject using a fully implanted device comprising one or more electrodes in electrical communication with the splenic nerve, thereby (i) deactivating one or more immune cells (such as natural killer cells and/or cytotoxic T cells) in the subject, and (ii) reducing inflammation in the subject (such as by decreasing a blood concentration of one or more inflammatory cytokines (e.g., tumor necrosis factor alpha (TNF-α), interleukin-6 (IL-6), and/or interleukin-1β (IL-1β))) in the subject. The method can optionally further include receiving, at the device, ultrasonic waves (for example, from an external ultrasonic transducer); and converting energy from the ultrasonic waves into electrical energy that powers the device. The splenic nerve can be electrically stimulated in response to a trigger signal. The trigger signal may be, for example, encoded in ultrasonic waves received by the device or may be generated by the device itself. The trigger signal can be based on splenic nerve activity and/or a measured physiological condition (e.g., a temperature, a pulse rate, or a blood pressure). Optionally, the splenic nerve activity and/or the physiological condition is measured by the device itself.

Methods of Monitoring Immune System Status or Inflammation in a Subject

The implantable medical device can configured to monitor an immune system status or inflammation in an individual. As discussed above, splenic nerve activity is associated with activity of immune cells that reside in or pass through the spleen, as well as splenic cytokine release, including pro-inflammatory cytokines such as TNF-α, IL-6, or IL-1β. Therefore, monitoring splenic nerve activity allows for monitoring of the immune system and inflammation, which can inform cancer treatment. For example, if a decrease in the inflammatory state of the subject is detected, e.g., by the implantable device (for example, relative to a target state), the implantable device may electrically stimulate the splenic nerve to activate and/or increase circulation of immune cells (e.g., NK cells and/or cytotoxic T-cells) and/or increase inflammation (e.g., by increasing a blood concentration of one or more pro-inflammatory cytokines). If an increase in the inflammatory state of the subject is detected, e.g., by the implantable device (for example, relative to a target state), the implantable device may electrically stimulate the splenic nerve to deactivate immune cells (e.g., NK cells and/or cytotoxic T cells) and/or reduce inflammation (e.g., by increasing a blood concentration of one or more pro-inflammatory cytokines). As further described herein, the implantable medical device can include one or more electrodes configured to detect splenic nerve activity. The one or more electrodes configured to detect splenic nerve activity may be the same or different as the one or more electrodes configured to electrically stimulate the splenic nerve.

Monitoring the immune system status through splenic nerve activity can allow for monitoring of an onset, offset, or magnitude of an immune response, such as an inflammatory response. A change in the status of the immune system may be detected by an increase in splenic nerve activity, a decrease in splenic nerve activity, or a change in a pattern of splenic nerve activity compared to a baseline splenic nerve activity. For example, an increase in inflammation can be indicated by a decrease in splenic nerve activity or a change in a pattern of splenic nerve activity.

The implantable medical device can include an ultrasonic transducer configured to emit an ultrasonic backscatter encoding information related splenic nerve activity. The information can include, for example, information related to an electrophysiological pulse transmitted by the splenic nerve, such as a frequency, voltage, shape or pulse pattern. The ultrasonic backscatter waves encoding the information can be received by an interrogator and analyzed to decode the information. The ultrasonic transducer of the implantable medical device can also receive ultrasonic waves that power the implantable device, which may be transmitted by the interrogator configured to receive the ultrasonic backscatter or a separate interrogator. The ultrasonic transducers on the implantable medical device receives the ultrasonic waves from an external transducer and converts energy from the ultrasonic waves into electrical energy that powers the implantable medical device.

Electrical current flows through the ultrasonic transducer, and the electrical current can be modulated to encode the information related to the splenic nerve activity. For example, the implantable medical device can include an integrated circuit electrically connected to the ultrasonic transducer and the electrodes configured to detect the splenic nerve activity. The integrated circuit can include a modulation circuit, which modulates the electrical current to encode the information related to the splenic nerve activity. Since the ultrasonic backscatter is affected by the electrical current flowing through the ultrasonic transducer, the ultrasonic backscatter emitted by the ultrasonic transducer encodes the splenic nerve activity information encoded into the modulated electrical current.

Deviation in the electrical signal detected by the implanted medical device indicates a change in the status of the immune system. For example, an increase in voltage potential of the splenic nerve over a period of time indicates increased inflammation in the subject. From the deviation of a baseline signal of splenic nerve activity, it is possible to determine an onset, offset, and a magnitude of an inflammatory response.

The ultrasonic backscatter emitted by the implantable medical device can be received by an external device (e.g., an interrogator), and the information encoded in the ultrasonic backscatter can be analyzed to determine the status of the immune system or a change in the status of the immune system, such as an inflammatory response.

A change in the immune response, such as an increase in inflammation, can indicate that a therapy, such as an anti-cancer therapy (e.g., electrically stimulating the splenic nerve and/or administration of an anti-cancer agent), should be administered to the subject. Accordingly, an anti-cancer therapy can be administered to the subject in response to a change in the immune system status. For example, a drug therapy is administered to the subject in response to a change in the status of the immune system. In another example, the therapy is an electrical stimulation of the splenic nerve.

Implantable Device

The implantable device includes two or more electrodes that are configured to be in electrical communication with the splenic nerve, and the device is configured to electrically stimulate the splenic nerve in a subject with cancer to modulate the immune system of the subject and/or treat the cancer. The implantable device can include a nerve cuff (which may be, for example, a helical nerve cuff) configured to position one or more of the electrodes in electrical communication with the splenic nerve. For example, the nerve cuff can include one or more of the electrodes, and be configured to at least partially wrap around the splenic nerve or the splenic neurovascular bundle. The implanted can device include a body, which contains a wireless communication system (e.g., one or more ultrasonic transducers or one or more radiofrequency antennas) and an integrated circuit that operates the device. For example, an ultrasonic transducer can be configured to receive ultrasonic waves, and convert the received ultrasonic waves into an electrical energy that powers the device. The body of the device can include or be connected to two or more electrodes or a sensor, which are in electric communication with the ultrasonic transducer (e.g., through the integrated circuit). An electric current that flows through the wireless communication system can be modulated to encode information in backscatter waves emitted by the wireless communication system. The encoded information may include, for example, data related to a physiological condition detected by the sensor (such as temperature, a pulse, and/or blood pressure), an electrophysiological signal detected by the electrodes, a status of the device (for example, a status confirming the device is receiving signals encoded in ultrasonic waves, confirming operation of the integrated circuit, or confirming that the device is being powered), or information related to an electrical pulse emitted by the implantable device.

The implantable device cab comprises a nerve cuff attached to the body that is sized and configured to attach the device to the splenic nerve or splenic nerve artery. The body may be attached to the nerve cuff, for example, by positioning the body (which may include a housing) on the outer surface of the nerve cuff. The nerve cuff is further sized and configured to position electrodes in electrical communication with the splenic nerve. The nerve cuff can be configured to at least partially surround the splenic nerve and position the two or more electrodes in electrical communication with the splenic nerve.

In an example of a fully implantable device, the device includes one or more electrodes configured to be in electrical communication with a splenic nerve of a subject with cancer, the device configured to electrically stimulate the splenic nerve, thereby modulating the immune system of the subject.

In an example of a fully implantable device, the device includes one or more electrodes configured to be in electrical communication with a splenic nerve of a subject with cancer, the device configured to electrically stimulate the splenic nerve, thereby activating and/or increasing the circulation of one or more immune cells (such as NK cells and/or cytotoxic T-cells) in the subject.

In an example of a fully implantable device, the device includes one or more electrodes configured to be in electrical communication with a splenic nerve of a subject with cancer, the device configured to electrically stimulate the splenic nerve, thereby increasing inflammation in the subject (such as by increasing a blood concentration of one or more inflammatory cytokines (e.g., pro-inflammatory cytokines, such as tumor necrosis factor alpha (TNF-α), interleukin-6 (IL-6), and/or interleukin-1β (IL-1β)) and/or decreasing a blood concentration of one or more anti-inflammatory cytokines (e.g., IL-10)).

In an example of a fully implantable device, the device includes one or more electrodes configured to be in electrical communication with a splenic nerve of a subject with cancer, the device configured to electrically stimulate the splenic nerve, thereby activating and/or increasing circulation of one or more immune cells (such as NK cells and/or cytotoxic T-cells) and increasing inflammation in the subject (such as by increasing a blood concentration of one or more inflammatory cytokines (e.g., pro-inflammatory cytokines, such as tumor necrosis factor alpha (TNF-α), interleukin-6 (IL-6), and/or interleukin-1β (IL-1β)) and/or decreasing a blood concentration of one or more anti-inflammatory cytokines (e.g., IL-10)) in the subject.

In an example of a fully implantable device, the device includes one or more electrodes configured to be in electrical communication with a splenic nerve of a subject with a cancer, the device configured to electrically stimulate the splenic nerve, thereby treating the cancer. Optionally, the device further includes an ultrasonic transducer configured to receive ultrasonic waves; and convert energy from the ultrasonic waves into electrical energy that powers the device.

In an example of a fully implantable device, the device includes one or more electrodes configured to be in electrical communication with a splenic nerve of a subject with a cancer, the device configured to electrically stimulate the splenic nerve, thereby activating and/or increasing circulation of one or more immune cells (such as NK cells and/or cytotoxic T-cells) and treating the cancer. Optionally, the device further includes an ultrasonic transducer configured to receive ultrasonic waves; and convert energy from the ultrasonic waves into electrical energy that powers the device.

In an example of a fully implantable device, the device includes one or more electrodes configured to be in electrical communication with a splenic nerve of a subject with a cancer, the device configured to electrically stimulate the splenic nerve, thereby increasing inflammation in the subject (such as by increasing a blood concentration of one or more inflammatory cytokines (e.g., pro-inflammatory cytokines, such as tumor necrosis factor alpha (TNF-α), interleukin-6 (IL-6), and/or interleukin-1β (IL-1β)) and/or decreasing a blood concentration of one or more anti-inflammatory cytokines (e.g., IL-10)) and treating the cancer. Optionally, the device further includes an ultrasonic transducer configured to receive ultrasonic waves; and convert energy from the ultrasonic waves into electrical energy that powers the device.

In an example of a fully implantable device, the device includes one or more electrodes configured to be in electrical communication with a splenic nerve of a subject with a cancer, the device configured to electrically stimulate the splenic nerve, thereby activating and/or increasing circulation of one or more immune cells (such as NK cells and/or cytotoxic T-cells), increasing inflammation in the subject (such as by increasing a blood concentration of one or more inflammatory cytokines (e.g., pro-inflammatory cytokines such as tumor necrosis factor alpha (TNF-α), interleukin-6 (IL-6), and/or interleukin-1β (IL-1β)) and/or decreasing a blood concentration of one or more anti-inflammatory cytokines (e.g., IL-10)), and treating the cancer. Optionally, the device further includes an ultrasonic transducer configured to receive ultrasonic waves; and convert energy from the ultrasonic waves into electrical energy that powers the device.

In an example of a fully implantable device, the device includes one or more electrodes configured to be in electrical communication with a splenic nerve of a subject with a cancer, the device configured to electrically stimulate the splenic nerve, thereby activating and/or increasing circulation of one or more immune cells (such as NK cells and/or cytotoxic T-cells), reducing inflammation in the subject (such as by reducing a blood concentration of one or more inflammatory cytokines (e.g., pro-inflammatory cytokines, such as tumor necrosis factor alpha (TNF-α), interleukin-6 (IL-6), and/or interleukin-1β (IL-1β)) and/or decreasing a blood concentration of one or more anti-inflammatory cytokines (e.g., IL-10)), and treating the cancer. Optionally, the device further includes an ultrasonic transducer configured to receive ultrasonic waves; and convert energy from the ultrasonic waves into electrical energy that powers the device.

In an example of a fully implantable device, the device includes one or more electrodes configured to be in electrical communication with a splenic nerve of a subject with cancer, the device configured to electrically stimulate the splenic nerve, thereby modulating the immune system of the subject to reduce inflammation in the subject. Optionally, the device further includes an ultrasonic transducer configured to receive ultrasonic waves; and convert energy from the ultrasonic waves into electrical energy that powers the device. The inflammation may be associated with pain, fever, non-cancerous tissue necrosis, or shock. The device can be configured to reduce a blood concentration of one or more inflammatory cytokines (e.g., pro-inflammatory cytokines, such as such as tumor necrosis factor alpha (TNF-α), interleukin-6 (IL-6), and/or interleukin-1β (IL-1β)) and/or increase a blood concentration of an anti-inflammatory cytokine (such as IL-10), in the subject upon electrically stimulating the splenic nerve. The device can be configured to decrease activation of one or more immune cells (such as NK cells and/or cytotoxic T-cells) in the subject electrically stimulating the splenic nerve.

Body of the Implantable Device

An implantable device, which may be used to detect an electrophysiological signal transmitted by a nerve or emit an electrical pulse to a nerve, can include a body attached to a nerve cuff configured to engage the splenic nerve or splenic neurovascular bundle. The body is, for example, attached to the nerve cuff without an interceding lead between the body and the nerve cuff. For example, the body may be positioned on the outer surface of the nerve cuff such that the body and the nerve cuff are simultaneously positioned when implanted in the body. The body may include a wireless communication system, which is electrically connected to two or more electrodes. The two or more electrodes can be configured to detect an electrophysiological signal transmitted by a nerve or emit an electrical pulse to the nerve, and at least one of the electrodes is included on the nerve cuff. The nerve cuff may be, for example, a helical nerve cuff as described in further detail herein. The implantable device is fully implantable; that is, no wires or leads connect outside the body of the subject after implantation.

The two or more electrodes of the device, including one or more of the electrodes on the nerve cuff, are electrically connected to the wireless communication system. The body of the device may further include an integrated circuit, and the electrodes are connected to the wireless communication system through the integrated circuit. The integrated circuit may be configured to operate the wireless communication system of the device body, and can operate the two or more electrodes of the implantable device to detect the electrophysiological signal and/or emit an electrical pulse. Optionally, the implantable device includes one or more sensors configured to detect a physiological condition (such as temperature sensor, an oxygen sensor, a pH sensor, a strain sensor, a pressure sensor, an impedance sensor, or a sensor that can detect a concentration of an analyte).

The body of the implantable device can include a wireless communication system, which can communicate with a separate device (such as an external interrogator or another implantable device). For example, the wireless communication may be configured to receive instructions for emitting one or more electrical pulses to the nerve and/or transmit information, such as data associated with detected electrophysiological signal transmitted by the nerve and/or data associated one or more physiological conditions (e.g., pulse, temperature, pressure, presence or concentration of an analyte, etc.). The wireless communication system can include, for example one or more ultrasonic transducers or one or more radiofrequency antennas. The wireless communication system may also be configured to receive energy (for example, through ultrasonic or radiofrequency (RF)) from another device, which can be used to power the implantable device.

Information about the detected electrophysiological signal or physiological condition may be transmitted using the wireless communication system to a receiving device. For example, the wireless communication system may include two or more ultrasonic transducers, which can be operated to encode information about the detected electrophysiological signal or physiological condition using ultrasonic backscatter waves or radiofrequency backscatter waves. Exemplary implantable devices that can detect an electrophysiological signal and encode information related to the detected electrophysiological signal are described in WO 2018/009910 A2. Exemplary implantable devices that can be operated using ultrasonic waves to emit an electrical pulse are described in WO 2018/009912 A2. Exemplary implantable devices that are powered by ultrasonic waves and can emit an ultrasonic backscatter encoding a detected physiological condition are described in WO 2018/009905 A2 and WO 2018/009911 A2.

An integrated circuit included in the device body can electrically connect and communicate between the electrodes or sensor and the wireless communication system (e.g., the one or more ultrasonic transducers or one or more RF antennas). The integrated circuit can include or operate a modulation circuit within the wireless communication system, which modulates an electrical current flowing through the wireless communication system (e.g., one or more ultrasonic transducers or one or more radiofrequency antennas) to encode information in the electrical current. The modulated electrical current affects backscatter waves (e.g., ultrasonic backscatter waves or radiofrequency backscatter waves) emitted by the wireless communication system, and the backscatter waves encode the information.

FIG. 1 shows a side view of an exemplary board assembly for an implantable device body, which may be surrounded by a housing, and can be attached to a nerve cuff. The board assembly includes a wireless communication system (e.g., an ultrasonic transducer) 102 and an integrated circuit 104. In this example, the integrated circuit 104 includes a power circuit that includes a capacitor 106. In this example, the capacitor is an "off chip" capacitor (in that it is not on the integrated circuit chip), but is still electrically integrated into the circuit. The capacitor can temporarily store electrical energy converted from energy (e.g., ultrasonic waves) received by the wireless communication system, and can be operated by the integrated circuit 104 to store or release energy. Optionally, the body further includes a sensor 108, configured to detect a physiological condition. The ultrasonic transducer 102, integrated circuit 104, the capacitor 106, and the optional sensor 108 are mounted on a circuit board 110 in this example, which may be a printed circuit board. The circuit board 110 may further include one or more feedthroughs 112a, 112b, 112c, and 112d that electrically connect the circuit board and/or integrated circuit to one or more electrodes of the nerve cuff. The wireless communication system 102 is electrically connected to the integrated circuit 104, and the integrated circuit 104 is electrically connected to the electrodes, here via the feedthroughs 112a, 112b, 112c, and 112d, thereby electrically connecting the wireless communication system 102 to the electrodes.

The wireless communication system can be configured to receive instructions for operating the implantable device. The instructions may be transmitted, for example, by a separate device, such as an interrogator. By way of example, ultrasonic waves received by the implantable device (for example, those transmitted by the interrogator) can encode instructions for operating the implantable device. In another example, RF waves received by the implantable device can encode instructions for operating the implantable device. The instructions may include, for example, a trigger signal that instructs the implantable device to emit an electrical pulse through the electrodes of the device. The trigger signal may include, for example, information relating to when the electrical pulse should be emitted, a pulse frequency, a pulse power or voltage, a pulse shape, and/or a pulse duration.

The implantable device can optionally be configured and operated to transmit information (i.e., uplink communication), which can be received by the interrogator, through the wireless communication system. The wireless communication system can be configured to actively generate a communication signal (e.g., ultrasonic waves or radiofrequency waves) that encode the information. The wireless communication system can be configured to transmit information encoded on backscatter waves (e.g., ultrasonic backscatter waves or RF backscatter waves). Backscatter communication provides a lower power method of transmitting information, which is particularly beneficial for small devices to minimize energy used. By way of example, the wireless communication system may include one or more ultrasonic transducers configured to receive ultrasonic waves and emit an ultrasonic backscatter, which can encode information transmitted by the implantable device. Current flows through the ultrasonic transducer, which can be modulated to encode the information. The current may be modulated directly, for example by passing the current through a sensor that modulates the current, or indirectly, for example by modulating the current using a modulation circuit based on a detected physiological condition or an electrophysiological pulse.

The information transmitted by the wireless communication system can include information unrelated to a detected physiological condition or electrophysiological pules detected by the implantable device. For example, the information can include one or more of: information related to the status of the implantable device or a confirmation signal that confirms an electrical pulse was emitted, the power, frequency, voltage, duration, or other information related to an emitted electrical pulse, and/or an identification code for the implantable device. Optionally, the integrated circuit is configured to digitize the information, and the wireless communication system can transmit the digitized information.

The information wirelessly transmitted using the wireless communication system can be received by an interrogator. The information can be transmitted by being encoded in backscatter waves (e.g., ultrasonic backscatter or radiofrequency backscatter). The backscatter can be received by the interrogator, for example, and deciphered to determine the encoded information. Additional details about backscatter communication are provided herein, and additional examples are provided in WO 2018/009905; WO 2018/009908; WO 2018/009910; WO 2018/009911; WO 2018/009912; International Patent Application No. PCT/US2019/028381; International Patent Application No. PCT/US2019/028385; and International Patent Application No. PCT/2019/048647; each of which is incorporated herein by reference for all purposes. The information can be encoded by the integrated circuit using a modulation circuit. The modulation circuit is part of the wireless communication system, and can be operated by or contained within the integrated circuit.

An interrogator can transmit energy waves (e.g., ultrasonic waves or radiofrequency waves), which are received by the wireless communication system of the device to generate an electrical current flowing through the wireless communication system (e.g., to generate an electrical current flowing through the ultrasonic transducer or the radiofrequency antenna). The flowing current can then generate backscatter waves that are emitted by the wireless communication system. The modulation circuit can be configured to modulate the current flowing through the wireless communication system to encode the information. For example, the modulation circuit may be electrically connected to an ultrasonic transducer, which received ultrasonic waves from an interrogator. The current generated by the received ultrasonic waves can be modulated using the modulation circuit to encode the information, which results in ultrasonic backscatter waves emitted by the ultrasonic transducer to encode the information. A similar approach may be taken with a radiofrequency antenna that receives radiofrequency waves. The modulation circuit includes one or more switches, such as an on/off switch or a field-effect transistor (FET). An exemplary FET that can be used with the implantable device is a metal-oxide-semiconductor field-effect transistor (MOSFET). The modulation circuit can alter the impedance of a current flowing through the wireless communication system, and variation in current flowing through the wireless communication system encodes the information. Information encoded in the backscatter waves can include information related to an electrophysiological signal transmitted by the nerve, an electrical pulse emitted by the implantable device, or a physiological condition detected by a sensor of the implantable device. Information encoded in the backscatter waves can include a unique identifier for the implantable device. This can be useful, for example, to ensure the interrogator is in communication with the correct implantable device when a plurality of implantable devices is implanted in the subject. The information encoded in the backscatter waves can include a verification signal that verifies an electrical pulse was emitted by the implantable device. The information encoded in the backscatter waves can include an amount of energy stored or a voltage in the energy storage circuit (or one or more capacitors in the energy storage circuit). The information encoded in the backscatter waves can include a detected impedance. Changes in the impedance measurement can identify scarring tissue or degradation of the electrodes over time.

The modulation circuit may be operated using a digital circuit or a mixed-signal integrated circuit (which may be part of the integrated circuit), which can actively encode the information in a digitized or analog signal. The digital circuit or mixed-signal integrated circuit may include a memory and one or more circuit blocks, systems, or processors for operating the implantable device. The memory may store, for example, one or more predetermined patterns of electrical pulses, which can be emitted by the implantable device These systems can include, for example, an onboard controller (e.g., microcontroller or processor, a finite state machine implementation, or digital circuit) capable of executing one or more programs stored on the implant or provided via ultrasonic communication between interrogator and implantable device. The digital circuit or a mixed-signal integrated circuit can include an analog-to-digital converter (ADC), which can convert analog signal encoded in the ultrasonic waves emitted from the interrogator so that the signal can be processed by the digital circuit or the mixed-signal integrated circuit. The digital circuit or mixed-signal integrated circuit can also operate the power circuit, for example to generate the electrical pulse to stimulate the tissue. The digital circuit or the mixed-signal integrated circuit can be configured to receive the trigger signal encoded in the ultrasonic waves transmitted by the interrogator, and operates the power circuit to discharge the electrical pulse in response to the trigger signal.

Figure 2:
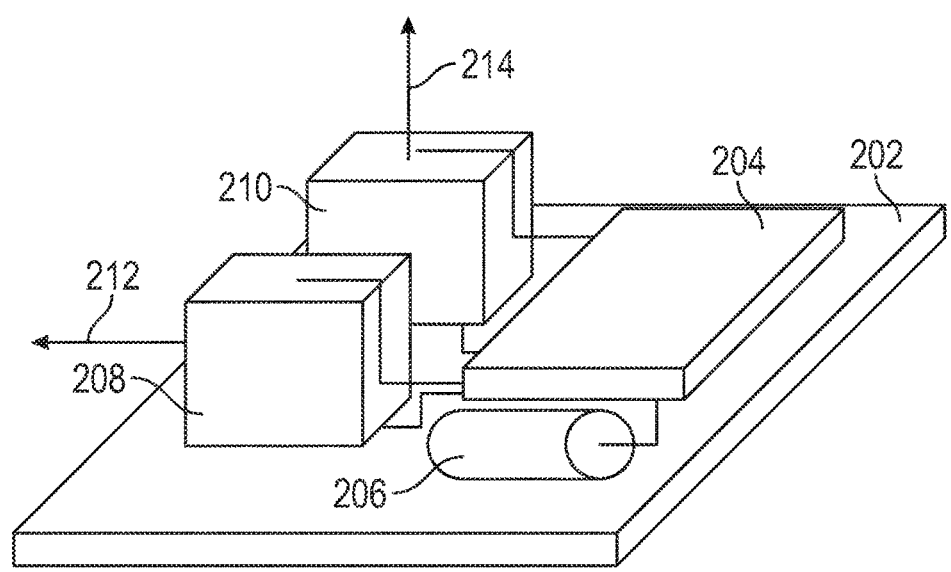
FIG. 2 shows an exemplary board assembly for a body of a device that includes two orthogonally positioned ultrasonic transducers.

The wireless communication system may include one or more ultrasonic transducers, such as one, two, or three or more ultrasonic transducers. The wireless communication system can include, for example, a first ultrasonic transducer having a first polarization axis and a second ultrasonic transducer having a second polarization axis, wherein the second ultrasonic transducer is positioned so that the second polarization axis is orthogonal to the first polarization axis, and wherein the first ultrasonic transducer and the second ultrasonic transducer are configured to receive ultrasonic waves that power the device and emit an ultrasonic backscatter. The wireless communication system may include a first ultrasonic transducer having a first polarization axis, a second ultrasonic transducer having a second polarization axis, and a third ultrasonic transducer having a third polarization axis, wherein the second ultrasonic transducer is positioned so that the second polarization axis is orthogonal to the first polarization axis and the third polarization axis, wherein the third ultrasonic transducer is positioned so that the third polarization axis is orthogonal to the first polarization and the second polarization axis, and wherein the first ultrasonic transducer and the second ultrasonic transducer are configured to receive ultrasonic waves that power the device and emit an ultrasonic backscatter. FIG. 2 shows an example of a board assembly for a body of a device that includes two orthogonally positioned ultrasonic transducers. The board assembly includes a circuit board 202, such as a printed circuit board, and an integrated circuit 204, which a power circuit that includes a capacitor 206. The body further includes a first ultrasonic transducer 208 electrically connected to the integrated circuit 204, and a second ultrasonic transducer 210 electrically connected to the integrated circuit 204. The first ultrasonic transducer 208 includes a first polarization axis 212, and the second ultrasonic transducer 210 includes a second polarization axis 214. The first ultrasonic transducer 208 and the second ultrasonic transducer are positioned such that the first polarization axis 212 is orthogonal to the second polarization axis 214.

The ultrasonic transducer, if included in the wireless communication system, can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO3$), lead zirconate titanate (PLT), zinc oxide (ZO), aluminum nitride (AlN), quartz, berlinite ($AlPO4$), topaz, langasite ($La3Ga5SiO14$), gallium orthophosphate ($GaPO4$), lithium niobate ($LiNbO3$), lithium tantalite ($LiTaO3$), potassium niobate ($KNbO3$), sodium tungstate ($Na2WO3$), bismuth ferrite ($BiFeO3$), polyvinylidene (di)fluoride (PVDF), and lead magnesium niobate-lead titanate (PMN-PT).

The bulk piezoelectric transducer may be approximately cubic (i.e., an aspect ratio of about 1:1:1 (length:width:height). The piezoelectric transducer may be plate-like, with an aspect ratio of about 5:5:1 or greater in either the length or width aspect, such as about 7:5:1 or greater, or about 10:10:1 or greater. The bulk piezoelectric transducer is long and narrow, with an aspect ratio of about 3:1:1 or greater, and where the longest dimension is aligned to the direction of the ultrasonic backscatter waves (i.e., the polarization axis). One dimension of the bulk piezoelectric transducer can be equal to one half of the wavelength ($\lambda$) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 μm to about 1000 μm (such as about 40 μm to about 400 μm, about 100 μm to about 250 μm, about 250 μm to about 500 μm, or about 500 μm to about 1000 μm). The height of the piezoelectric transducer can be about 5 mm or less (such as about 4 mm or less, about 3 mm or less, about 2 mm or less, about 1 mm or less, about 500 μm or less, about 400 μm or less, 250 μm or less, about 100 μm or less, or about 40 μm or less). The height of the piezoelectric transducer can be about 20 μm or more (such as about 40 μm or more, about 100 μm or more, about 250 μm or more, about 400 μm or more, about 500 μm or more, about 1 mm or more, about 2 mm or more, about 3 mm or more, or about 4 mm or more) in length. The ultrasonic transducer can have a length of about 5 mm or less such as about 4 mm or less, about 3 mm or less, about 2 mm or less, about 1 mm or less, about 500 μm or less, about 400 μm or less, 250 μm or less, about 100 μm or less, or about 40 μm or less) in the longest dimension. The ultrasonic transducer can have a length of about 20 μm or more (such as about 40 μm or more, about 100 μm or more, about 250 μm or more, about 400 μm or more, about 500 m or more, about 1 mm or more, about 2 mm or more, about 3 mm or more, or about 4 mm or more) in the longest dimension.

The ultrasonic transducer, if included in the wireless communication system, can be connected two electrodes to allow electrical communication with the integrated circuit. The first electrode is attached to a first face of the transducer and the second electrode is attached to a second face of the transducer, wherein the first face and the second face are opposite sides of the transducer along one dimension. The electrodes can comprise, for example, silver, gold, platinum, platinum-black, poly(3,4-ethylenedioxythiophene (PEDOT), a conductive polymer (such as conductive PDMS or polyimide), or nickel. The axis between the electrodes of the transducer may be orthogonal to the motion of the transducer.

The implantable device may be configured to wirelessly receive energy and convert the energy into an electrical energy, which may be used to power the device. The wireless communication system may be used to wirelessly receive the energy, or a separate system may be configured to receive the energy. For example, an ultrasonic transducer (which may be an ultrasonic transducer contained within the wireless communication system or a different ultrasonic transducer) can be configured to receive ultrasonic waves and convert energy from the ultrasonic waves into an electrical energy. Optionally, an RF antenna (which may be an RF antenna contained within the wireless communication system or a different RF antenna) is configured to receive RF waves and convert the energy from the RF waves into an electrical energy. The electrical energy is transmitted to the integrated circuit to power the device. The electrical energy may power the device directly, or the integrated circuit may operate a power circuit to store the energy for later use.

The integrated circuit can include a power circuit, which can include an energy storage circuit. The energy storage circuit may include a battery, or an alternative energy storage device such as one or more capacitors. The implantable device is preferably batteryless, and may instead rely on one or more capacitors. By way of example, energy from ultrasonic waves or radiofrequency waves received by the implantable device (for example, through the wireless communication system) is converted into a current, and can be stored in the energy storage circuit. The energy can be used to operate the implantable device, such as providing power to the digital circuit, the modulation circuit, or one or more amplifiers, or can be used to generate the electrical pulse used to stimulate the tissue. The power circuit may further includes, for example, a rectifier and/or a charge pump.

The integrated circuit may be configured to operate the two or more electrodes of the device configured to detect an electrophysiological signal transmitted by a nerve or emit an electrical pulse to the nerve, and at least one of the electrodes is included on the nerve cuff. The electrodes may be positioned on the nerve cuff, the body of the device, or both (e.g., one or more electrodes may be on the body of the device and one or more electrodes may be on the nerve cuff). In some embodiments, the housing of the body operates as an electrode. For example, the device may include one or more working electrodes on the nerve cuff, and the housing may be configured as a counter electrode. Accordingly, the housing of the device may be electrically connected to the integrated circuit. The one or more electrodes on the nerve cuff are electrically connected to the integrated circuit, for example through one or more feedthroughs.

The implantable device can include one or more sensors configured to detect a physiological condition. The sensor(s) may be, for example, included as part of the body of the device or on the nerve cuff. The sensors are configured to detect a physiological condition, such as temperature, oxygen concentration, pH, an analyte (such as glucose), strain, or pressure. Variation in the physiological condition modulates impedance, which in turn modulates current flowing through a detection circuit electrically connected to or part of the integrated circuit. The implantable device may comprise, for example, one or more (such as 2, 3, 4, 5 or more) sensors, which may detect the same physiological condition or different physiological conditions. The implantable device can comprises, for example, 10, 9, 8, 7, 6 or 5 or fewer sensors). For example, the implantable device may comprises a first sensor configured to detect temperature and a second sensor configured to detect oxygen, such as $spO_2$. Changes in both physiological conditions can be encoded in the backscatter waves emitted by the wireless communication system, which can be deciphered by an external computing system (such as the interrogator).

The body of the implantable device is attached to the nerve cuff, for example on the outer surface of the helical nerve cuff. The body may be attached to an end of the nerve cuff, or at a middle portion of the nerve cuff. Optionally, a handle portion may be attached to the nerve cuff, and may be attached at a position proximal to the body. The implantable device can include, for example, a handle portion attached to the helical nerve cuff at a position proximal to the body attached to the nerve cuff, and a second handle portion attached to the nerve cuff at a distal position, such as at an end of the nerve cuff. Examples of an implantable device body attached to a helical nerve cuff is shown in FIGS. 7D, 7E, 7F, 8C, and 9C. A handle portion can optionally be attached to the body of the implantable device.

Figure 3:
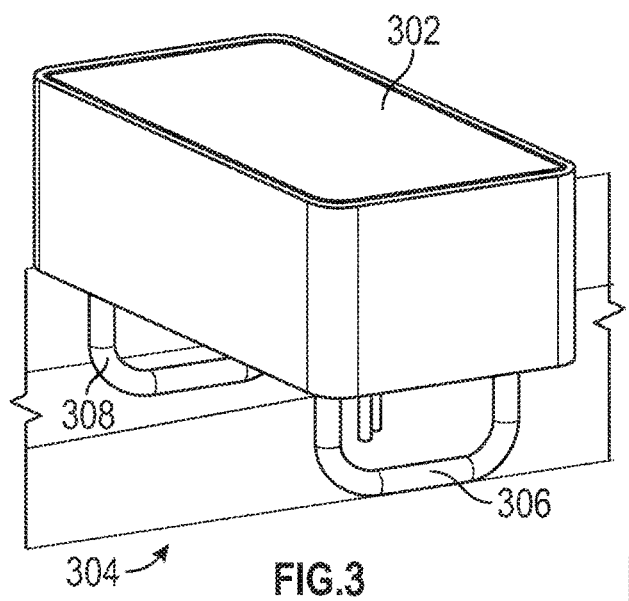
FIG. 3 shows an exemplary body housing attached to a nerve cuff using fasteners.

The body of the of the implantable device may be attached to nerve cuff through an adhesive (e.g., an epoxy, glue, cement, solder, or other binder), one or more fasteners (e.g., a staple, screw, bolt, clap, rivet, pin, rod, etc.), or any other suitable means to securely attach the body to the nerve cuff to ensure that it does not become separated from the nerve cuff after implantation. FIG. 3 shows an exemplary body 302 attached to a nerve cuff 304 using fasteners (306 and 308). The body may have an elongated shape, and one end of the body (i.e., the attachment end) can be attached to the nerve cuff, and the opposite end (i.e., an extension end) can extend from the nerve cuff (see, for example, the body attached to the nerve cuff in FIG. 7E). The body is, in this example, directly attached to the outer surface of the nerve cuff (i.e., without any interceding lead between body and the nerve cuff).

The body can include a housing, which can include a base, one or more sidewalls, and a top. The housing is optionally made from an electrically conductive material and may be configured as one of the one or more electrodes of the implantable device configured to detect an electrophysiological signal transmitted by a nerve or emit an electrical pulse to the nerve. For example, the housing of the body may be configured as a counter electrode, and one or more electrodes on the nerve cuff may be configured as an operating electrode. The housing can be made from a bioinert material, such as a bioinert metal (e.g., steel or titanium) or a bioinert ceramic (e.g., titania or alumina). The housing is preferably hermetically sealed, which prevents body fluids from entering the body.

Figure 4:
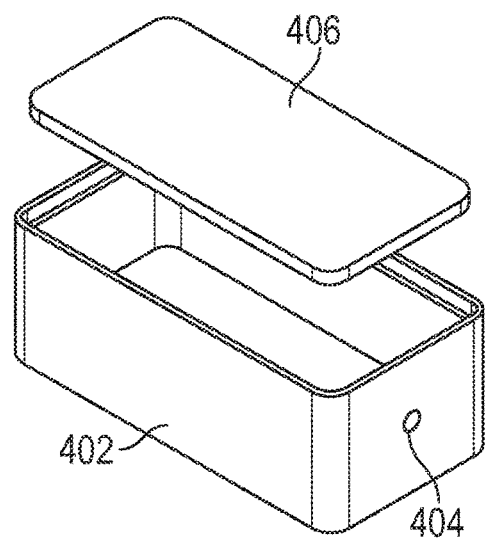
FIG. 4 shows an exemplary housing with an acoustic window that may be attached to the top of the housing, and a port that may be used to fill the housing with an acoustically conductive material.

Referring to FIG. 4, an acoustic window 406 can be included in the housing 402 of the body, for example on the top of the housing. An acoustic window is a thinner material (such as a foil) that allows acoustic waves to penetrate the housing so that they may be received by one or more ultrasonic transducers within the body of the implantable device. The housing (or the acoustic window of the housing) may be thin to allow ultrasonic waves to penetrate through the housing is about 100 micrometers (μm) or less in thickness, such as about 75 μm or less, about 50 μm or less, about 25 μm or less, about 15 μm or less, or about 10 μm or less. The thickness of the housing (or the acoustic window of the housing) may be about 5 µm to about 10 µm, about 10 µm to about 15 µm, about 15 m to about 25 µm, about 25 µm to about 50 µm, about 50 µm to about 75 µm, or about 75 µm to about 100 µm in thickness.

The housing 402 may be filled with an acoustically conductive material, such as a polymer or oil (such as a silicone oil). The material can fill empty space within the housing to reduce acoustic impedance mismatch between the tissue outside of the housing and within the housing. Accordingly, the body of the device is preferably void of air or vacuum. A port 404 can be included on the housing, for example on the sidewall of the housing (see FIG. 4), to allow the housing to be filled with the acoustically conductive material. Once the housing is filled with the material, the port can be sealed to avoid leakage of the material after implantation.

The housing of the implantable device is relatively small, which allows for comfortable and long-term implantation while limiting tissue inflammation that is often associated with implantable devices. The longest dimension of the housing of the device may be about 8 mm or less, about 7 mm or less, about 6 m or less, about 5 mm or less, about 4 mm or less, about 3 mm or less, about 2 mm or less, about 1 mm or less, about 0.5 mm or less, about 0.3 mm or less, about 0.1 mm or less in length. The longest dimension of the housing of the device may be about 0.05 mm or longer, about 0.1 mm or longer, about 0.3 mm or longer, about 0.5 mm or longer, about 1 mm or longer, about 2 mm or longer, about 3 mm or longer, about 4 mm or longer, about 5 mm or longer, about 6 mm or longer, or about 7 mm or longer in the longest dimension of the device. For example, the longest dimension of the housing of the device can be about 0.3 mm to about 8 mm in length, about 1 mm to about 7 mm in length, about 2 mm to about 6 mm in length, or about 3 mm to about 5 mm in length. The housing of the implantable device can have a volume of about 10 mm$^3$ or less (such as about 8 mm$^3$ or less, 6 mm$^3$ or less, 4 mm$^3$ or less, or 3 mm$^3$ or less). In some embodiments, the housing of the implantable device has a volume of about 0.5 mm$^3$ to about 8 mm$^3$, about 1 mm$^3$ to about 7 mm$^3$, about 2 mm$^3$ to about 6 mm$^3$, or about 3 mm$^3$ to about 5 mm$^3$.

Figure 5A:
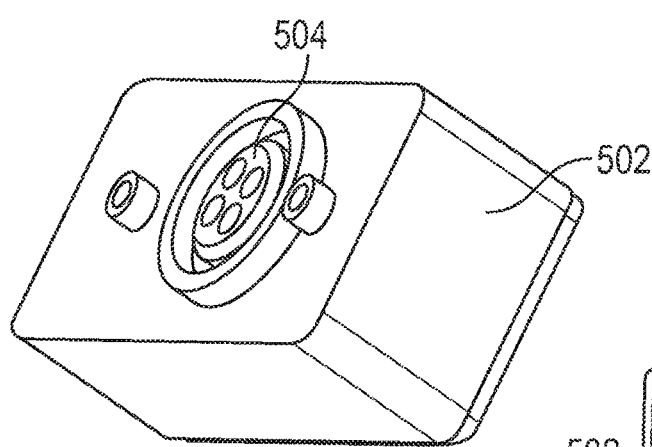
FIG. 5A shows an exemplary housing with a feedthrough port at the base of the housing.
Figure 5B:
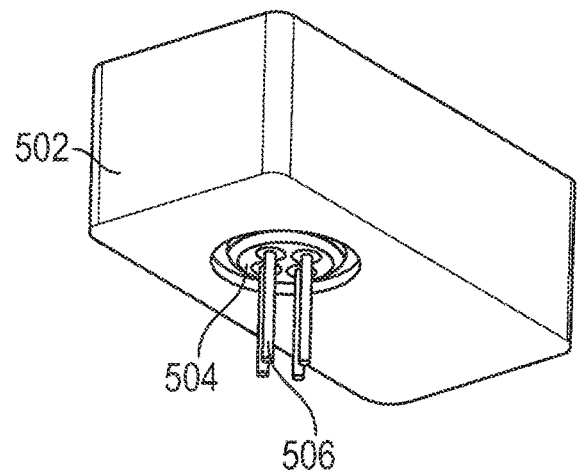
FIG. 5B shows a housing with a feedthrough attached to the housing. The feedthroughs fit through the feedthrough port, and are brazed, soldered, or otherwise attached to the housing to form a hermetic seal.

The housing (such as the bottom of the housing) can include a feedthrough port, which may be aligned with the feedthrough port of the nerve cuff. A feedthrough can electrically connect the one or more electrodes of the nerve cuff to components of the body within the housing. For example, the feedthrough may be electrically connected to an integrated circuit and/or the wireless communication system of the device body. FIG. 5A shows a housing 502 with a feedthrough port 504, and FIG. 5B shows the housing with the feedthrough 506 positioned to electrically connect the body components to one or more electrodes of the nerve cuff. FIG. 5C shows a cross-sectional view of an exemplary device, wherein the feedthrough 506 electronically connects electrodes 508 on the nerve cuff to the electronic circuitry 510 (integrated circuit, wireless communication system, etc.) positioned within the body housing 502. The feedthroughs may include or be, for example, a metal (such as a metal comprising silver, copper, gold, platinum, platinum-black, or nickel) sapphire, or a conductive ceramic (for example indium tin oxide (ITO)). The electrodes may be connected to the feedthrough using any suitable means, such as soldering, laser welding, or crimping the feedthrough to the electrodes.

The implantable device can be implanted in a subject. The subject can be for example, a mammal. The subject can be a human, dog, cat, horse, cow, pig, sheep, goat, monkey, or a rodent (such as a rat or mouse). The nerve cuff may be configured to at least partially wrap around a filamentous tissue (such as a splenic nerve, or a splenic neurovascular bundle) within any of these animals, or others.

Implantable Device Nerve Cuff

The implantable device can include a nerve cuff sized and configured to attach the device to the splenic nerve and/or a splenic artery and position at least one of the two or more electrodes in electrical communication with the splenic nerve. The splenic nerve cuff can be a helical nerve cuff.

The splenic nerve cuff is configured to hold the implantable device in place on the splenic nerve and/or splenic artery. The splenic nerve cuff can be configured to allow for some rotational movement of the implantable device on the splenic nerve and/or splenic artery. The splenic nerve cuff may grip the splenic nerve and/or splenic artery by exerting an inward pressure on the nerve and/or artery. The amount of inward pressure exerted by the splenic nerve cuff can be determined based on the size and curvature of the splenic nerve cuff, as well as by the spring constant of the splenic nerve cuff. The inward pressure should be sufficient to hold the implantable device in place while the tissue heals after insertion, but not so high that the epineurium or vascular walls that contact the legs are damaged. Inward pressure on the splenic nerve or neurovascular bundle can be about 1 MPa or less (such as about 0.7 MPa or less, about 0.5 MPa or less, or about 0.3 MPa or less). The inward pressure on the splenic nerve or neurovascular bundle can be about 0.1 MPa to about 1 MPa (such as about 0.1 MPa to about 0.3 MPa, about 0.3 MPa to about 0.5 MPa, about 0.5 MPa to about 0.7 MPa, or about 0.7 MPa to about 1 MPa).

The nerve cuff includes a helical substrate configured to at least partially wrap around a filamentous tissue comprising a nerve, and one or more electrodes positioned along the length of the substrate. The nerve cuff may optionally include one or more handle portions, for example a handle portion attached to an end of the substrate. The nerve cuff may be a helical nerve cuff.

The inner diameter of the nerve cuff may be selected based on the diameter of the filamentous tissue, which may different depending on the species of the subject or other anatomical differences within the subject (e.g., the size of the nerve within the specific subject. By way of example, the inner diameter may be between about 1 mm and about 8 mm in diameter (such as between about 1 mm and about 2 mm, about 2 mm and about 3 mm, about 3 mm and about 4 mm, about 4 mm and about 5 mm, about 5 mm and about 6 mm, about 6 mm and about 7 mm, or about 7 mm and about 8 mm in diameter).

The nerve cuff may be configured to wrap around the nerve by at least one revolution. For example, the nerve cuff may wrap around the nerve by about 1 to about 4 revolutions, such as about 1 to about 1.3 revolutions, about 1.3 to about 1.7 revolutions, about 1.7 to about 2 revolutions, about 2 to about 2.5 revolutions, about 2.5 to about 3 revolutions, or about 3 to about 4 revolutions. The nerve cuff may be configured to wrap around the nerve by about 1.5 revolutions.

Optionally, the substrate of the nerve cuff is an elongated material wound into a helical shape. The helical substrate may have a substantially flat inner surface and/or a substantially flat outer surface. The width of the substrate may be substantially uniform, with optionally tapered or rounded ends. The width of the substrates define edges, and the edges may or may not contact each other as the substrate winds in the helical shape when the nerve cuff is in a relaxed position. For example, a gap may or may not separate the revolutions of the substrate. The substrate can have a width that defines an inner surface, a first edge of the substrate, and a second edge of the substrate, and wherein at least a portion of the first edge contacts at least a portion of the second edge when the nerve cuff is in a relaxed position. Alternatively, the substrate can have a width that defines an inner surface, a first edge of the substrate, and a second edge of the substrate, and wherein the first edge does not contact the second edge when the nerve cuff is in a relaxed position.

The substrate of the nerve cuff is made from an electrically insulating material, which may be a biocompatible and/or elastomeric material. Exemplary substrate materials include, but are not limited to, silicone, silicone rubber, polydimethylsioloxane (PDMS), a urethane polymer, a poly (p-xylylene) polymer (such as a poly(p-xylylene) polymer sold under the tradename PARYLENE®), or a polyimide.

The substrate of the nerve cuff may include two or more layers, which may be of the same material or of different materials. The layers can included an inner layer that forms the inner surface of the nerve cuff and contacts the fibrous tissue, and an outer layer that forms the outer surface of the nerve cuff. An electrically conductive material may be positioned between the inner and outer layers, which can form the electrodes of the nerve cuff. For example, the inner layer can include one or more opening on the inner surface to expose the electrically conductive material, which defines the electrodes. The separate inner and outer layers can further define the helical shape of the substrate. For example, the inner layer may be under higher tensile force than the outer layer when the helical nerve cuff is in a flexed configuration, which forces the substrate to curl inwards when the helical nerve cuff is in a relaxed configuration.

The width of the nerve cuff can depend on the on the length of nerve cuff (i.e., the maximal distance along an axis running through the center of the helix between the ends of the nerve cuff), the number of revolutions of the substrate, and size of a gap between substrate revolutions (if any). The length of the nerve cuff can be about 4 mm to about 20 mm (such as about 4 mm to about 7 mm, about 7 m to about 10 mm, about 10 mm to about 13 mm, about 13 mm to about 16 mm, or about 16 mm to about 20 mm). The width (or the inner width) of the substrate can be about 2 mm to about 8 mm (such as about 2 mm to about 4 mm, about 4 mm to about 6 mm, or about 6 mm to about 8 mm).

The nerve cuff may be flexible, which allows for manipulation of the nerve cuff upon implantation. For example, in some embodiments, the helical nerve cuff can be configured in a flexed position by at least partially unwinding the helical nerve cuff, and a relaxed position with the helical nerve cuff in a helical configuration. FIG. 6A shows an exemplary helical nerve cuff in a flexed position, wherein both the right-handed helical portion and the left-handed helical portion of the nerve cuff are partially unwound by pulling a first handle portion and a second handle portion which are joined together and attached to either end of the right-handed helical portion and the left-handed helical portion in one direction, and pulling a third handle portion attached to a joining member in the opposite direction. FIG. 6B shows the same helical nerve cuff shown in FIG. 6A in a relaxed position.

The nerve cuff may include a right-handed helical portion, a left-handed helical portion, or both a right-handed helical portion a left-handed helical portion. For example, the nerve cuff may include a right-handed helical portion joined to a left-handed helical portion, either directly or through a connecting member (which may be linear, curved, or hinged).

The one or more electrodes of the nerve cuff may be positioned on the inner surface of the nerve cuff substrate, and may be uncoated or coated with an electrically conductive material (e.g., electroplated with a poly(3,4-ethylenedioxythiophene) (PEDOT) polymer or other electrically conductive polymer or a metal to improve electrical characteristics of the electrode). One or more of the electrodes can be point electrodes. I One or more of the electrodes can be elongated, and may be positioned, for example, along the length of the substrate. The electrodes may terminate before the end of the substrate, at the end of the substrate, or beyond the end of the substrate. The one or more electrodes may be connected to a feed through on the nerve cuff, which allows the electrodes to be electrically connected to the outer surface of the substrate or a body attached to the outer surface of the nerve cuff.

The nerve cuff can include one or more electrodes, such as 1, 2, 3, 4, 5, 6, 7, 8, 9, 10 or more electrodes. One or more of the electrodes can be configured to emit an electrical pulse to the nerve. The nerve cuff can include 1, 2, 3, 4, 5, 6, 7, 8, 9, 10 or more electrodes configured to emit an electrical pulse to the nerve. One or more of the electrodes can be configured to detect an electrophysiological signal transmitted by the nerve. The nerve cuff can includes 1, 2, 3, 4, 5, 6, 7, 8, 9, 10 or more electrodes configured to detect an electrophysiological signal transmitted by the nerve. One or more electrodes can be configured to emit an electrical pulse to the nerve, and one or more of the electrodes can be configured to detect an electrophysiological signal transmitted by the nerve. An electrode configured to emit an electrical pulse may be wider than an electrode configured to detect an electrophysiological signal. Electrodes of the nerve cuff (having more than one electrode) may be positioned along the length of the nerve cuff alongside each other, or in different directions.

The optional handle portion is configured to be grasped by a surgical grasping tool (e.g., forceps, hook, or other grasping or gripping instrument), and may be useful for manipulating the nerve cuff during implantation. The handle portion may extend from or be partially embedded within the substrate, and may be more flexible and/or thinner than the substrate to facilitate grasping of the handle portion and manipulation of the nerve cuff. The handle portion may include a loop, for example within the handle portion or by forming a loop by either end of the handle portion being attached to the substrate. The handle portion can comprise a flexible filament (such as a thread, string, cord, suture, or wire), which is optionally biodegradable once implanted within the subject. The handle portion can comprises a bioabsorbable material, such as polyglycolide, polydioxanone, polycaprolactone, or copolymers thereof.

The optional handle portion may be attached to the nerve cuff proximal to the end of the nerve cuff (e.g., at the tip of the nerve cuff). The nerve cuff optionally includes more than one handle portion. For example, the substrate may include an additional handle portion proximal to the opposite end of the substrate and/or an additional handle portion proximal to a middle portion of the substrate. If the nerve cuff is attached to a body, as further discussed herein, the one of the handle portions may be proximal to the body or distal to the body. By way of example, the body can be attached proximal to a first end of the nerve cuff, and the handle portion is attached proximal to the second end of the helical nerve cuff. The body can be attached proximal to a first end of the nerve cuff, and the handle portion is attached proximal to the first end of the nerve cuff. In some embodiments, a body is attached proximal to a first end of the nerve cuff, and a first handle portion is attached proximal to the body and a second handle portion is attached proximal to a second end of the nerve cuff. Alternatively, the body can be attached to a middle portion of the nerve cuff, a first handle portion is attached proximal to a first end of the nerve cuff, a second handle portion is attached proximal to the body, and optionally a third handle portion is attached proximal to the second end of the nerve cuff.

Optionally, two or more handle portions attached to the nerve cuff are joined together. For example, a first handle portion includes a first end attached proximal to a first end of the helical nerve cuff, a second handle portion includes a first end attached proximal to a second end of the nerve cuff, and the second end of the first handle portion and the second end of the second handle portion are joined together.

Figure 7A:
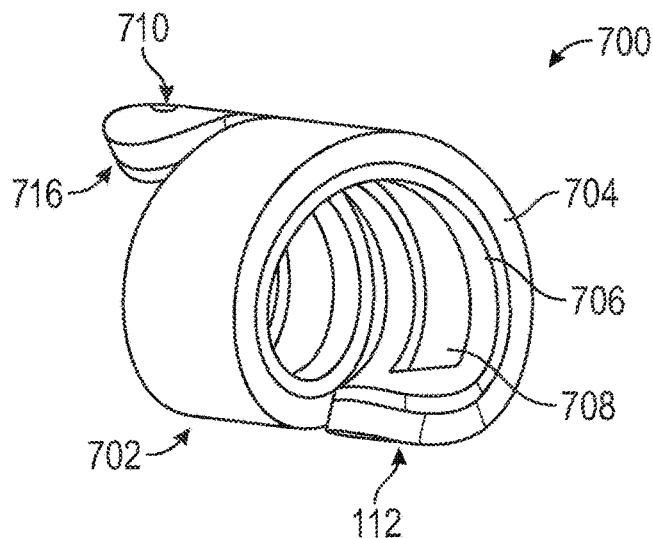
FIG. 7A shows an exemplary helical nerve cuff, which may optionally be part of the implantable device described herein.
Figure 7B:
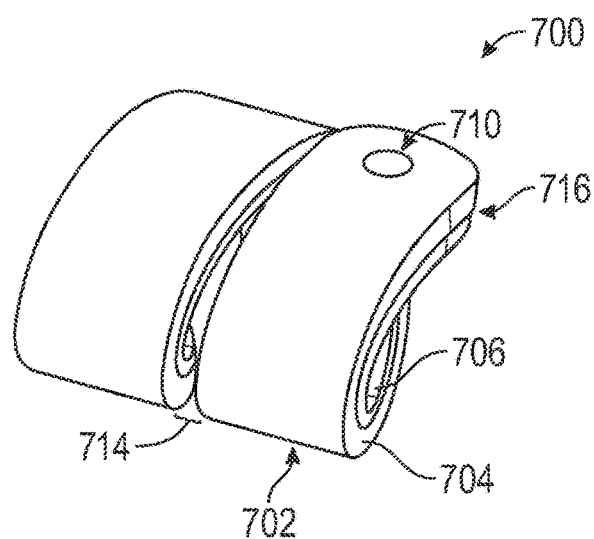
FIG. 7B shows the nerve cuff illustrated in FIG. 7A from a different angle.

FIG. 7A illustrates an exemplary helical nerve cuff, which may optionally be part of the implantable device described herein. FIG. 7B shows the nerve cuff illustrated in FIG. 7A from a different angle. The nerve cuff 700 includes a helical substrate 702 that includes an outer layer 704 and an inner layer 706. The nerve cuff is configured to wrap around the nerve by about 1.5 revolutions, and a gap 714 separates substrate revolutions. The substrate 702 is configured as a left-handed helix, although an embodiment with a right-handed helical substrate is also contemplated. An elongate electrode 708 is positioned on the inner surface of the helical substrate 702. The elongated electrode 708 spans from a feedthrough port 710, and terminates at a position before the end 712 of the helical substrate 702. The electrode 708 is between the outer layer 704 and the inner layer 706, and the inner layer 106 includes an elongated cutout that exposes the electrode 708 to the inner surface of the nerve cuff 700. In an alternative embodiment, the electrode is positioned on top of the inner layer 706. FIG. 7D and FIG. 7E show the helical nerve cuff of FIG. 7A and FIG. 7B attached to a body having a housing 722. The housing 722 is attached to the outer surface of the helical nerve cuff substrate 702. A feedthrough 724 passes through the feedthrough port 710 that electrically connects the elongated electrode 708 to the body.

Figure 7C:
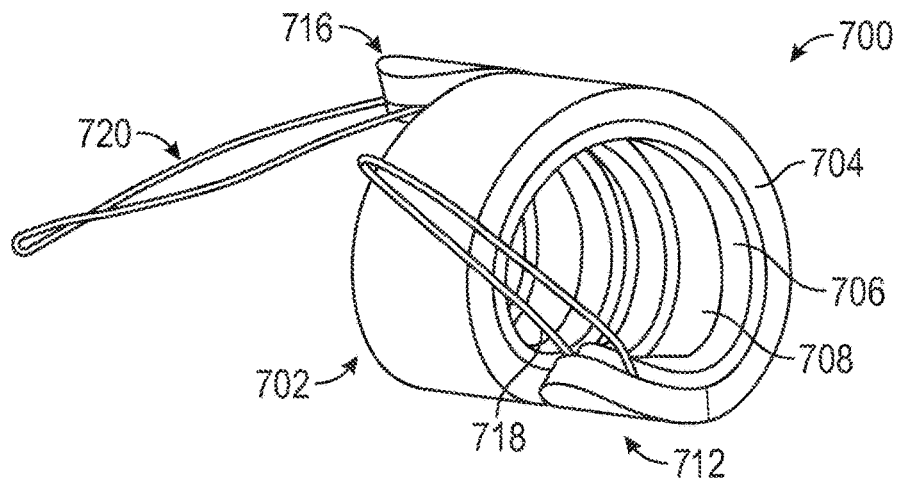
FIG. 7C shows an exemplary helical nerve cuff similar to the nerve cuff shown in FIG. 7A and FIG. 7B, but further includes a first handle portion attached to the helical substrate proximal to a first end of the substrate, and a second handle portion attached to the helical substrate proximal to a second end of the substrate.
Figure 7D:
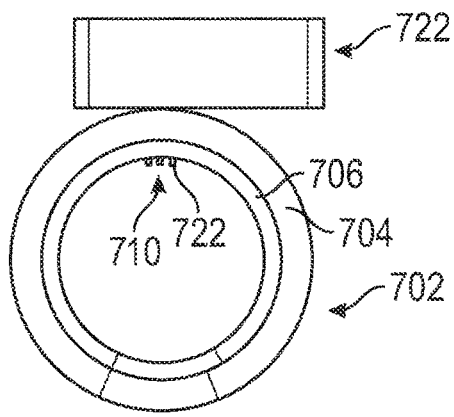
FIG. 7D and FIG. 7E show the helical nerve cuff of FIG. 7A and FIG. 7B attached to a body having a housing.
Figure 7E:
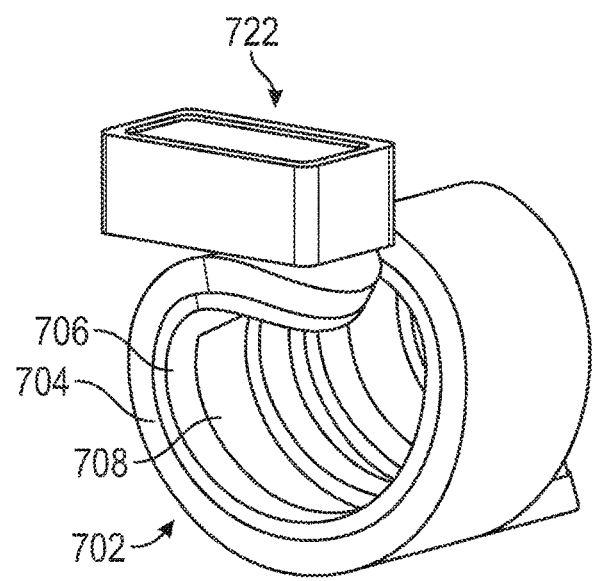
Figure 7F:
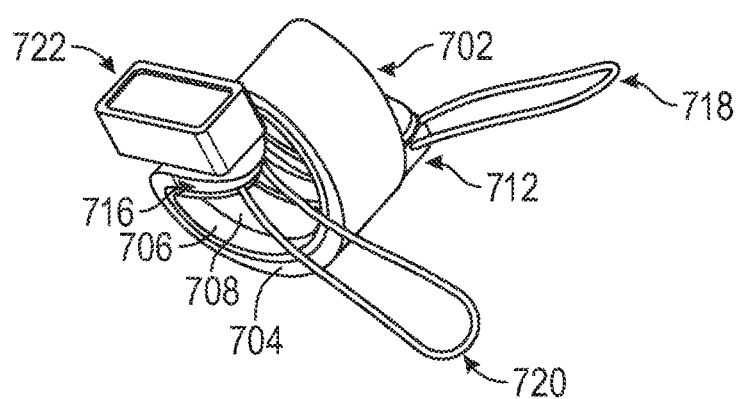
FIG. 7F shows the helical nerve cuff of FIG. 7C attached to a body having a housing.

FIG. 7C illustrates an exemplary helical nerve cuff similar to the nerve cuff illustrated in FIG. 7A and FIG. 7B, but further includes a first handle portion 718 attached to the helical substrate 702 proximal to a first end 712 of the substrate 702, and a second handle portion 720 attached to the helical substrate 702 proximal to a second end 716 of the substrate 702. The first handle portion 718 and the second handle portion 720 are each flexible filaments that form a loop, with each end of the filament attached to the substrate 702. The ends of the filament are embedded within the substrate 702 between the inner layer 706 and the outer layer 704. FIG. 7F shows the helical nerve cuff of FIG. 7C attached to a body having a housing 722. The housing 722 is attached to the outer surface of the helical nerve cuff substrate 702.

Figure 8A:
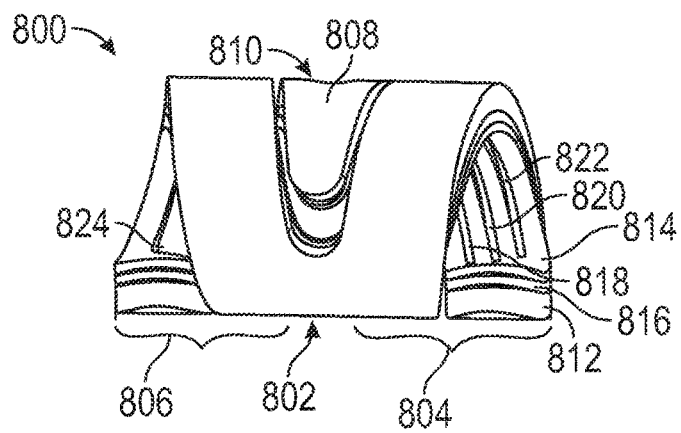
FIG. 8A and FIG. 8B show front and back perspectives, respectively, of another exemplary helical nerve cuff.
Figure 8B:
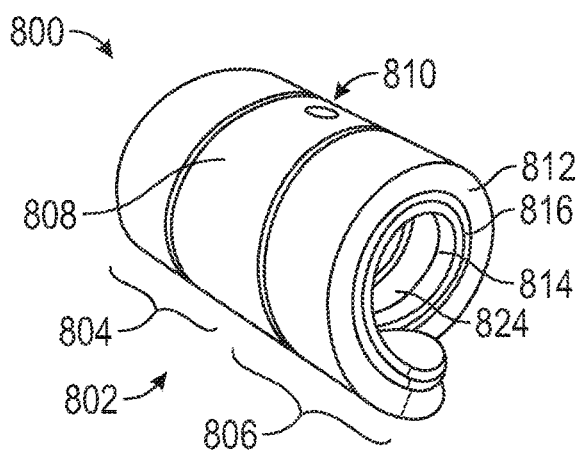
Figure 8C:
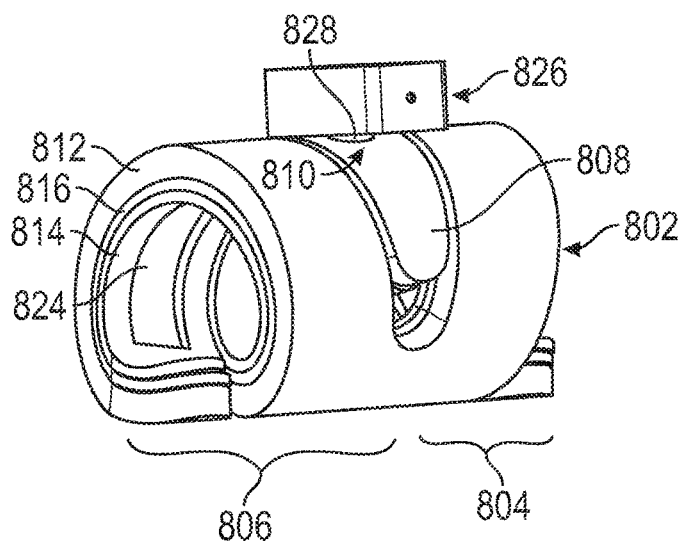
FIG. 8C shows the helical nerve cuff of FIG. 8A and FIG. 8B attached to a body having a housing.

FIG. 8A and FIG. 8B illustrate front and back perspectives, respectively, of another example of a helical nerve cuff 800. The nerve cuff 800 includes a substrate 802 with a left-handed helical segment 804 and a right-handed helical segment 806 joined together through a connecting member 808. The connecting member 808 of the illustrated nerve cuff 800 is a curved and elongated portion of the substrate 802 that makes slightly less than one full rotation around the nerve. A feedthrough port 810 is positioned along the connecting member 808, which allows a body to be electrically connected to electrodes positioned on the inner surface of the substrate. The substrate 802 includes an outer layer 812 and an inner layer 814, which sandwiches and electrically conductive middle layer 816 between the outer layer 812 and the inner layer 814. The helical nerve cuff, in this example, includes three parallel elongated electrodes (818, 820, and 822) configured to detect an electrophysiological signal transmitted by a nerve on the inner surface of the substrate 802 at the left-handed helical segment 204, and a fourth elongated electrode 824 configured to emit an electrical pulse to the nerve on the inner surface of the substrate 802 at the right-handed helical segment 206. The electrodes are defined by an opening in the inner layer 814. In the illustrated example, the fourth elongated electrode 824 is wider than the electrodes 818, 820, and 822. FIG. 8C shows the helical nerve cuff of FIG. 8A and FIG. 8B attached to a body having a housing 826. The housing 826 is attached to the outer surface of the helical nerve cuff substrate 802 at the connecting member 808. A feedthrough 828 passes through the feedthrough port 810 at electrically connects the electrodes 818, 820, 822, and 824 to the body.

Figure 9A:
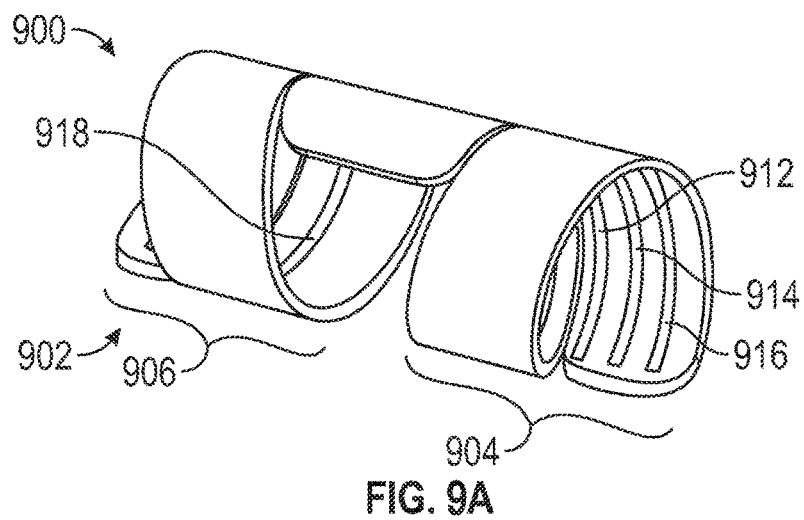
FIG. 9A and FIG. 9B show front and bottom perspectives, respectively, of another exemplary helical nerve cuff.
Figure 9B:
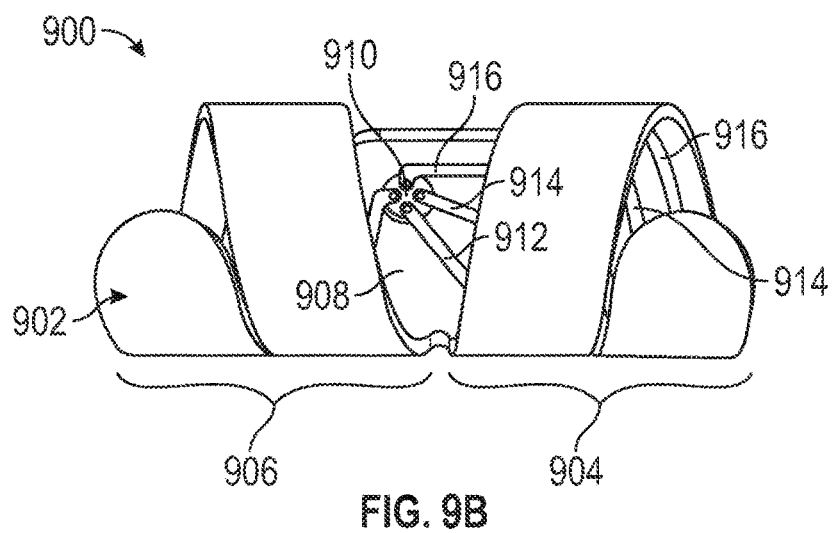
Figure 9C:
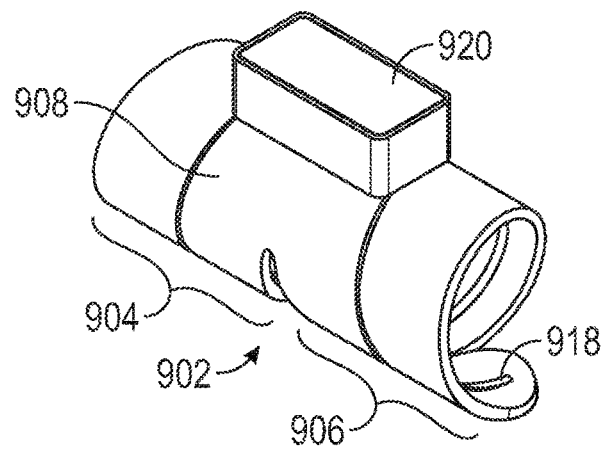
FIG. 9C shows the helical nerve cuff of FIG. 9A and FIG. 9B attached to a body having a housing.

FIG. 9A and FIG. 9B illustrate front and bottom perspectives, respectively, of another example of a helical nerve cuff 900. The nerve cuff 900 includes a substrate 902 with a left-handed helical segment 904 and a right-handed helical segment 906 joined together through a connecting member 908. The connecting member 908 of the illustrated nerve cuff 900 is a curved and elongated portion of the substrate 902, which is shorter than the connecting member of the nerve cuff illustrated in FIG. 8A and FIG. 8B. A feedthrough port 910 is positioned along the connecting member 908, which allows a body to be electrically connected to electrodes positioned on the inner surface of the substrate. The substrate 902 of the illustrated never cuff 900 includes a single layer, with electrodes positioned along the inner surface of the substrate 902. The helical nerve cuff, in this example, includes three elongated electrodes (912, 914, and 916) on the inner surface of the substrate 902 at the left-handed helical segment 904, and a fourth elongated electrode 918 on the inner surface of the substrate 902 at the right-handed helical segment 906. FIG. 9C shows the helical nerve cuff of FIG. 9A and FIG. 9B attached to a body having a housing 920. The housing 920 is attached to the outer surface of the helical nerve cuff substrate 902.

Figure 10A:
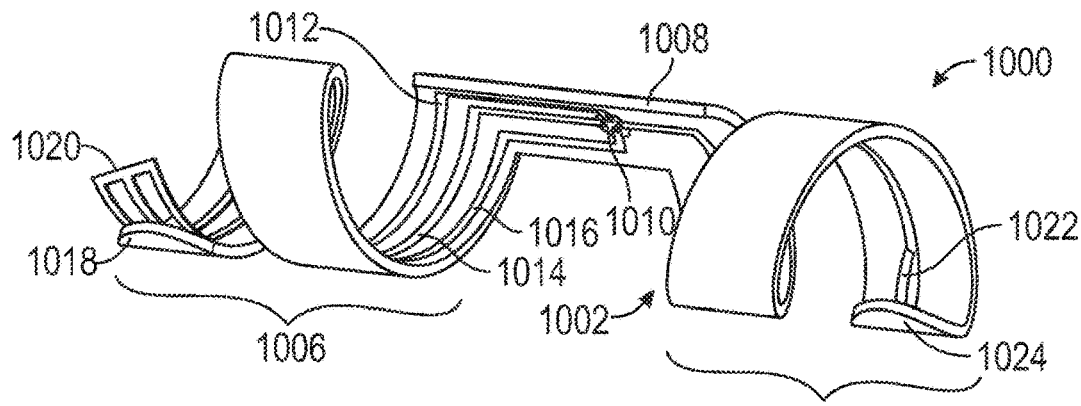
FIG. 10A and FIG. 10B show bottom and top perspectives, respectively, of another example of a helical nerve cuff.
Figure 10B:
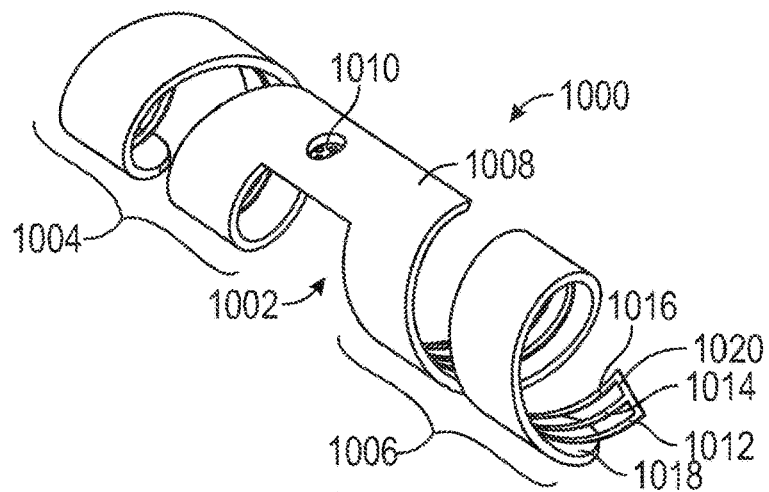

FIG. 10A and FIG. 10B illustrate bottom and top perspectives, respectively, of another example of a helical nerve cuff 1000. The nerve cuff 1000 includes a substrate 1002 with a left-handed helical segment 1004 and a right-handed helical segment 1006 joined together through a connecting member 1008. The connecting member 1008 of the illustrated nerve cuff 1000 is an elongated and linear connecting member. A feedthrough port 1010 is positioned along the connecting member 1008, which allows a body to be electrically connected to electrodes positioned on the inner surface of the substrate. The substrate 1002 of the illustrated never cuff 1000 includes a single layer, with electrodes positioned along the inner surface of the substrate 1002. The helical nerve cuff, in this example, includes three parallel elongated electrodes (1012, 1014, and 1016) on the inner surface of the substrate 1002 at the left-handed helical segment 1004, and extend beyond the end 1018 of the nerve cuff 1000. In the illustrated example, the electrodes 1012, 1014, and 1016 which are joined together at a joining end 1020. The nerve cuff further includes a fourth elongated electrode 1022 on the inner surface of the substrate 1002 at the right-handed helical segment 1006, which extends beyond the opposite end 1024 of the nerve cuff 1000.

Figure 11A:
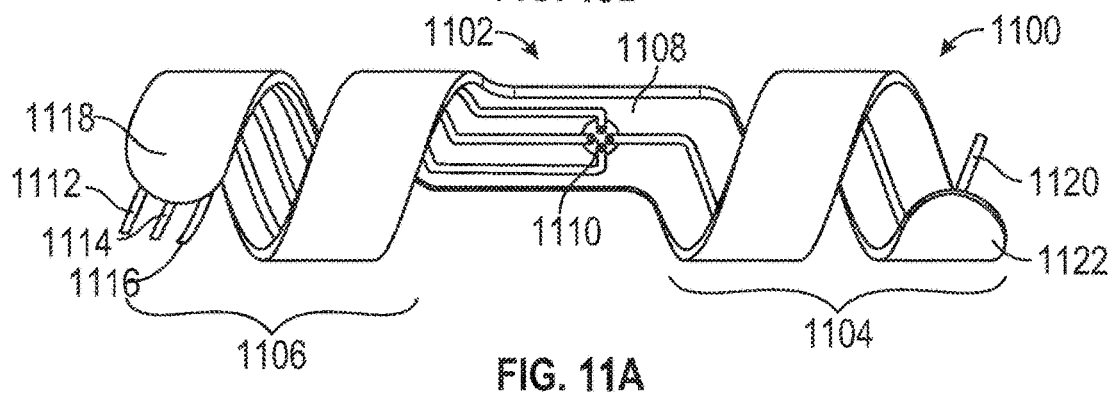
FIG. 11A and FIG. 11B show bottom and top perspectives, respectively, of another example of a helical nerve cuff.
Figure 11B:
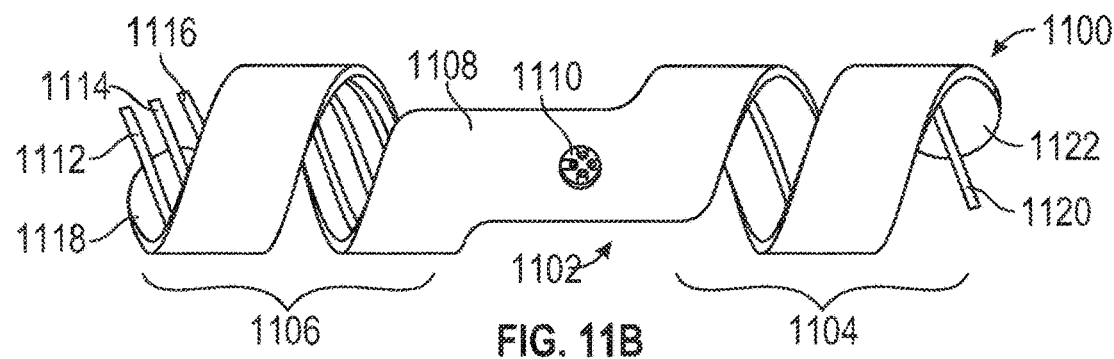

FIG. 11A and FIG. 11B illustrate bottom and top perspectives, respectively, of another example of a helical nerve cuff

1100. The nerve cuff 1100 includes a substrate 1102 with a first left-handed helical segment 1104 and a second left-handed helical segment 1106 joined together through a connecting member 1108. The connecting member 1108 of the illustrated nerve cuff 1100 is an elongated and linear connecting member. A feedthrough port 1110 is positioned along the connecting member 1108, which allows a body to be electrically connected to electrodes positioned on the inner surface of the substrate. The substrate 1102 of the illustrated never cuff 1100 includes a single layer, with electrodes positioned along the inner surface of the substrate 1102. The helical nerve cuff, in this example, includes three parallel elongated electrodes (1112, 1114, and 1116) on the inner surface of the substrate 1102 at the first left-handed helical segment 1104, and extend beyond the end 1118 of the nerve cuff 1100. The nerve cuff further includes a fourth elongated electrode 1120 on the inner surface of the substrate 1102 at the second left-handed helical segment 1106, which extends beyond the opposite end 1122 of the nerve cuff 1100.

Interrogator

The interrogator is configured to wirelessly communicate with one or more implantable devices using ultrasonic waves, which are used to power and/or operate the implantable device. For example, the interrogator can transmit ultrasonic waves that encode instructions for operating the device, such as a trigger signal that instructs the implantable device to emit an electrical pulse. The interrogator can further receive ultrasonic backscatter from the implantable device, which encodes information transmitted by the implantable device. The information may include, for example, information related to a detected electrophysiological pulse, an electrical pulse emitted by the implantable device, and/or a measured physiological condition. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. The ultrasound transmitting function can be separated from the ultrasound receiving function on separate devices. That is, optionally, the interrogator comprises a first device configured to transmit ultrasonic waves to the implantable device, and a second device configured to receive ultrasonic backscatter from the implantable device. The transducers in the array can have regular spacing, irregular spacing, or be sparsely placed. Optionally, the array is flexible. The array may be planar or non-planar.

Figure 12:
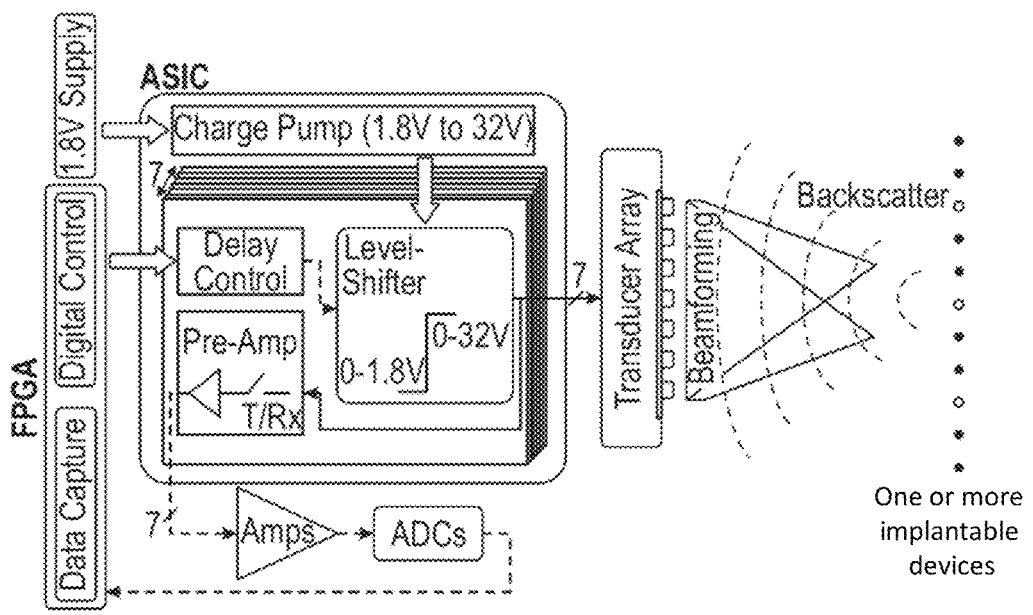
FIG. 12 shows an exemplary interrogator that can be used with the implantable device.

An exemplary interrogator is shown in FIG. 12. The illustrated interrogator shows a transducer array with a plurality of ultrasonic transducers. The transducer array can include 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. The transducer array can include 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels.

The interrogator shown in FIG. 12 illustrates a single transducer array; however the interrogator can include 1 or more, 2 or more, or 3 or more separate arrays. The interrogator can include, for example, 10 or fewer transducer arrays (such as 9, 8, 7, 6, 5, 4, 3, 2, or 1 transducer arrays). The separate arrays, for example, can be placed at different points of a subject, and can communicate to the same or different implantable devices. The arrays can be located on opposite sides of an implantable device. The interrogator can include an application specific integrated circuit (ASIC), which includes a channel for each transducer in the transducer array. The channel can include a switch (indicated in FIG. 12 by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit.

The transducer connected to the channel may be configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. The data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. The ASIC can include a charge pump (illustrated in FIG. 12) to convert a first voltage supplied to the ASIC to a higher second voltage, which is applied to the channel. The channels can be controlled by a controller, such as a digital controller, which operates the delay control.

In the ultrasound receiving circuit, the received ultrasonic waves are converted to current by the transducers (set in a receiving mode), which is transmitted to a data capture circuit. An amplifier, an analog-to-digital converter (ADC), a variable-gain-amplifier, or a time-gain-controlled variable-gain-amplifier which compensates for tissue loss, and/or a band pass filter can be included in the receiving circuit. The ASIC can draw power from a power supply, such as a battery (which is preferred for a wearable embodiment of the interrogator). In the example illustrated in FIG. 12, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. The T/Rx circuit can include a circulator. The transducer array can contain more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

The interrogator can be configured to be implantable. Alternatively, the interrogator is configured to be external (i.e., not implanted). By way of example, the external interrogator can be a wearable, which may be fixed to the body by a strap or adhesive. In another example, the external interrogator can be a wand, which may be held by a user (such as a healthcare professional). The interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator.

The specific design of the transducer array depends on the desired penetration depth, aperture size, and size of the individual transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and X is the wavelength of ultrasound in the propagation medium (i.e., the tissue). As understood in the art, the Rayleigh distance is the distance at which the beam radiated by the array is fully formed. That is, the pressure field converges to a natural focus at the Rayleigh distance in order to maximize the received power. Therefore, the implantable device may be approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). Beam steering may be performed by adjusting the power or phase of the ultrasonic waves emitted by the transducers in an array.

The interrogator can include one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Optionally, the interrogator is controlled using a separate computer system, such as a mobile device (e.g., a smartphone or a tablet). The computer system can wirelessly communicate to the interrogator, for example through a network connection, a radiofrequency (RF) connection, or Bluetooth. The computer system may, for example, turn on or off the interrogator or analyze information encoded in ultrasonic waves received by the interrogator.

Communication Between an Implantable Device and an Interrogator

The implantable device and the interrogator wirelessly communicate with each other using ultrasonic waves. The implantable device receives ultrasonic waves from the interrogator through one or more ultrasonic transducers on the implantable device, and the ultrasonic waves can encode instructions for operating the implantable device. Vibrations of the ultrasonic transducer(s) on the implantable device generate a voltage across the electric terminals of the transducer, and current flows through the device, including the integrated circuit. The current can be used to charge an energy storage circuit, which can store energy to be used to emit an electrical pulse, for example after receiving a trigger signal. The trigger signal can be transmitted from the interrogator to the implantable device, signaling that an electrical pulse should be emitted. The trigger signal can include information regarding the electrical pulse to be emitted, such as frequency, amplitude, pulse length, or pulse shape (e.g., alternating current, direct current, or pulse pattern). A digital circuit can decipher the trigger signal and operate the electrodes and electrical storage circuit to emit the pulse.

Ultrasonic backscatter may be emitted from the implantable device, which can encode information relating to the implantable device, the electrical pulse emitted by the implantable device, an electrophysiological pulse detected by the implantable device, or a detected physiological condition. For example, the ultrasonic backscatter can encode a verification signal, which verifies that electrical pulse was emitted. An implantable device can be configured to detect an electrophysiological signal, and information regarding the detected electrophysiological signal can be transmitted to the interrogator by the ultrasonic backscatter. To encode signals in the ultrasonic backscatter, current flowing through the ultrasonic transducer(s) of the implantable device is modulated as a function of the encoded information, such as a detected electrophysiological signal or measured physiological condition. Modulation of the current can be an analog signal, which may be, for example, directly modulated by the detected splenic nerve activity. Alternatively, modulation of the current encodes a digitized signal, which may be controlled by a digital circuit in the integrated circuit. The backscatter is received by an external ultrasonic transceiver (which may be the same or different from the external ultrasonic transceiver that transmitted the initial ultrasonic waves). The information from the electrophysiological signal can thus be encoded by changes in amplitude, frequency, or phase of the backscattered ultrasound waves.

Figure 13:
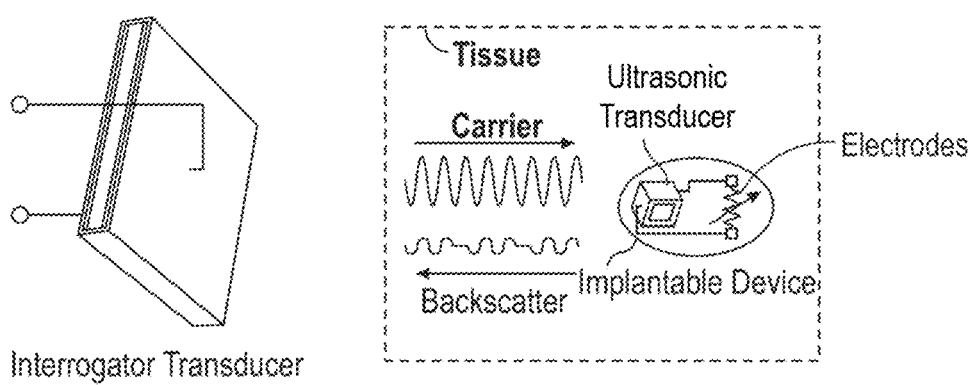
FIG. 13 shows an exemplary interrogator in communication with an implantable device. The interrogator can transmit ultrasonic waves, which can encode a trigger signal. The implantable device emits an ultrasonic backscatter, which can be modulated by the implantable device to encode information.

FIG. 13 shows an interrogator in communication with an implantable device. The external ultrasonic transceiver emits ultrasonic waves ("carrier waves"), which can pass through tissue. The carrier waves cause mechanical vibrations on the miniaturized ultrasonic transducer (e.g., a miniaturized bulk piezoelectric transducer, a PUMT, or a CMUT). A voltage across the ultrasonic transducer is generated, which imparts a current flowing through an integrated circuit on the implantable device. The current flowing through to the ultrasonic transducer causes the transducer on the implantable device to emit backscatter ultrasonic waves. The integrated circuit can modulate the current flowing through the ultrasonic transducer to encode information, and the resulting ultrasonic backscatter waves can encode the information. The backscatter waves can be detected by the interrogator, and can be analyzed to interpret information encoded in the ultrasonic backscatter.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. The pulses can be square, rectangular, triangular, sawtooth, or sinusoidal. The pulses output can be two-level (GND and POS), three-level (GND, NEG, POS), 5-level, or any other multiple-level (for example, if using 24-bit DAC). The pulses can be continuously transmitted by the interrogator during operation. When the pulses are continuously transmitted by the interrogator, a portion of the transducers on the interrogator can be configured to receive ultrasonic waves and a portion of the transducers on the interrogator can be configured to transmit ultrasonic waves. Transducers configured to receive ultrasonic waves and transducers configured to transmit ultrasonic waves can be on the same transducer array or on different transducer arrays of the interrogator. A transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period.

The backscattered ultrasound can be digitized by the implantable device. For example, the implantable device can include an oscilloscope or analog-to-digital converter (ADC) and/or a memory, which can digitally encode information in current (or impedance) fluctuations. The digitized current fluctuations, which can encode information, are received by the ultrasonic transducer, which then transmits digitized acoustic waves. The digitized data can compress the analog data, for example by using singular value decomposition (SVD) and least squares-based compression. The compression can be performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

The digitized data can include a unique identifier. The unique identifier can be useful, for example, in a system comprising a plurality of implantable devices and/or an implantable device comprising a plurality of electrode pairs. For example, the unique identifier can identify the implantable device of origin when from a plurality of implantable devices, for example when transmitting information from the implantable device (such as a verification signal). An implantable device can comprises a plurality of electrode pairs, which may simultaneously or alternatively emit an electrical pulse by a single implantable device. Different pairs of electrodes, for example, can be configured to emit an electrical pulse in different tissues (e.g., different nerves or different muscles) or in different regions of the same tissue. The digitized circuit can encode a unique identifier to identify and/or verify which electrode pairs emitted the electrical pulse.

The digitized signal can compress the size of the analog signal. The decreased size of the digitized signal can allow for more efficient reporting of information encoded in the ultrasonic backscatter. By compressing the size of the transmitted information through digitization, potentially overlapping signals can be accurately transmitted.

An interrogator can communicate with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. The interrogator can receive a combined backscatter from the plurality of the implantable devices, which can be deconvoluted, thereby extracting information from each implantable device. The interrogator can focuse the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. The interrogator can transmit ultrasonic waves to a plurality of implantable devices, and then receives ultrasonic waves from the plurality of implantable devices.

Exemplary Embodiments

The following embodiments are exemplary and are not intended to limit the scope of the present application:

Embodiment 1. A method of modulating the immune system of a subject with a cancer, comprising:
electrically stimulating the splenic nerve of the subject using a fully implanted device comprising one or more electrodes in electrical communication with the splenic nerve sufficient to modulate the immune system of the subject.

Embodiment 2. The method of embodiment 1, further comprising identifying a subject with cancer.

Embodiment 3. A method of treating a cancer in a subject, comprising: electrically stimulating the splenic nerve of the subject using a fully implanted device comprising one or more electrodes in electrical communication with the splenic nerve sufficient to modulate the immune system of the subject and treat the cancer in the subject.

Embodiment 4. The method of embodiment 3, further comprising identifying a subject with cancer.

Embodiment 5. The method of embodiment any one of embodiments 1-4, wherein modulating the immune system comprises increasing activation of one or more immune cells in the subject.

Embodiment 6. The method of embodiment 5, wherein modulating the immune system comprises increasing activation of natural killer (NK) cells or cytotoxic T-cells in the subject.

Embodiment 7. The method of any one of embodiments 1-6, wherein modulating the immune system comprises increasing circulation or activation of NK cells in the subject.

Embodiment 8. The method of any one of embodiments 1-7, wherein modulating the immune system comprises increasing a blood concentration of an inflammatory cytokine in the subject.

Embodiment 9. The method of any one of embodiments 1-7, wherein modulating the immune system comprises decreasing a blood concentration of an inflammatory cytokine in the subject.

Embodiment 10. The method of embodiment 8 or 9, wherein the inflammatory cytokine is tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), or RANTES.

Embodiment 11. The method of embodiment 8 or 9, wherein the inflammatory cytokine is a pro-inflammatory cytokine.

Embodiment 12. The method of embodiment 11, wherein the pro-inflammatory cytokine is tumor necrosis factor alpha (TNF-α), interleukin-6 (IL-6), or interleukin-1β (IL-1β).

Embodiment 13. The method of embodiment 8 or 9, wherein the inflammatory cytokine is an anti-inflammatory cytokine Embodiment 14A. The method of embodiment 13, wherein the anti-inflammatory cytokine is interleukin-10 (IL-10).

Embodiment 14B. The method of any one of embodiments 1-7, wherein modulating the immune system comprises increasing inflammation in the subject.

Embodiment 15. The method of embodiment 14B, wherein modulating the immune system comprises increasing a blood concentration of a pro-inflammatory cytokine in the subject.

Embodiment 16. The method of embodiment 15, wherein the pro-inflammatory cytokine is tumor necrosis factor alpha (TNF-α), interleukin-6 (IL-6), or interleukin-1β (IL-1β).

Embodiment 17. The method of any one of embodiments 14B-16, wherein modulating the immune system comprises decreasing a blood concentration of an anti-inflammatory cytokine in the subject.

Embodiment 18. The method of embodiment 17, wherein the anti-inflammatory cytokine is interleukin-10 (IL-10).

Embodiment 19. The method of any one of embodiments 14B-18, wherein modulating the immune system comprises increasing a blood concentration of tumor necrosis factor alpha (TNF-α), and reducing a blood concentration of interleukin-10 (IL-10).

Embodiment 20. The method of any one of embodiments 14B-19, wherein the splenic nerve is electrically stimulated with a plurality of electrical pulses emitted at a frequency of about 25 Hz or higher.

Embodiment 21. The method of any one of embodiments 14B-20, wherein the splenic nerve is electrically stimulated with a plurality of electrical pulses emitted at a frequency of about 30 Hz to about 100 Hz.

Embodiment 22. The method of any one of embodiments 14B-21, wherein the splenic nerve is electrically stimulated using a plurality of biphasic electrical pulses comprising an anodal phase followed by a cathodal phase.

Embodiment 23. The method of any one of embodiments 1-7, wherein modulating the immune system comprises reducing inflammation in the subject.

Embodiment 24. The method of embodiment 23, wherein modulating the immune system comprises increasing a blood concentration of an anti-inflammatory cytokine in the subject.

Embodiment 25. The method of embodiment 24, wherein the anti-inflammatory cytokine is interleukin-10 (IL-10).

Embodiment 26. The method of any one of embodiments 23-25, wherein modulating the immune system comprises reducing a blood concentration of a pro-inflammatory cytokine in the subject.

Embodiment 27. The method of embodiment 26, wherein the pro-inflammatory cytokine is tumor necrosis factor alpha (TNF-α), interleukin-6 (IL-6), or interleukin-1β (IL-1β).

Embodiment 28. The method of any one of embodiments 23-27, wherein modulating the immune system comprises reducing a blood concentration of tumor necrosis factor alpha (TNF-α), and increasing a blood concentration of interleukin-10 (IL-10).

Embodiment 29. The method of any one of embodiments 23-28, wherein the splenic nerve is electrically stimulated with a plurality of electrical pulses emitted at a frequency of less than 25 Hz.

Embodiment 30. The method of any one of embodiments 23-29, wherein the splenic nerve is electrically stimulated with a plurality of electrical pulses emitted at a frequency of about 3 Hz to about 20 Hz.

Embodiment 31. The method of any one of embodiments 23-30, wherein the splenic nerve is electrically stimulated using a plurality of biphasic electrical pulses comprising a cathodal phase followed by an anodal phase.

Embodiment 32. A method of reducing inflammation in a subject with cancer, comprising:
electrically stimulating the splenic nerve of the subject using a fully implanted device comprising one or more electrodes in electrical communication with the splenic nerve sufficient to modulate the immune system to reduce inflammation in the subject.

Embodiment 33. The method of embodiment 32, further comprising identifying the subject with cancer.

Embodiment 34. The method of embodiment 32 or 33, wherein the inflammation is associated with pain, fever, non-cancerous tissue necrosis, or shock.

Embodiment 35. The method of any one of embodiments 1-34, comprising:
receiving, at the device, ultrasonic waves from an external ultrasonic transducer; and
converting energy from the ultrasonic waves into electrical energy that powers the device.

Embodiment 36. The method of embodiment 35, comprising transmitting the ultrasonic waves that power the implanted device using an external device.

Embodiment 37. The method of any one of embodiment 1-36, wherein the splenic nerve is electrically stimulated using one or more electrical pulses about 1 ms in length or less.

Embodiment 38. The method of any one of embodiments 1-37, wherein the splenic nerve is electrically stimulated using one or more electrical pulses having an amplitude of about 250 µA to about 10 mA.

Embodiment 39. The method of any one of embodiments 1-38, wherein the splenic nerve is electrically stimulated using one or more electrical pulses at a frequency of about 100 Hz or less.

Embodiment 40. The method of any one of embodiments 1-21, 23-30, and 32-39, wherein the splenic nerve is electrically stimulated using a pulse train comprising a plurality of biphasic electrical pulses.

Embodiment 41. The method of embodiment 23, wherein the biphasic electrical pulses comprises an anodal phase followed by a cathodal phase.

Embodiment 42. The method of embodiment 23, wherein the biphasic electrical pulses comprises a cathodal phase followed by an anodal phase.

Embodiment 43. The method of any one of embodiments 1-42, wherein the splenic nerve is electrically stimulated using a plurality of pulse trains comprising two or more electrical pulses, the pulse trains separated by a dwell time of about 50 ms or more.

Embodiment 44. The method of embodiment 43, wherein the dwell time is about 50 ms to about 2 minutes, or about 500 ms or more.

Embodiment 45. The method of embodiment 43 or 44, wherein the plurality of pulse trains comprises at least a first pulse train followed by a second pulse train, wherein electrical pulses in the first pulse train have an amplitude lower than an amplitude of electrical pulses in the second pulse train.

Embodiment 46. The method of any one of embodiments 1-42, wherein the splenic nerve is electrically stimulated using tonic electrical pulses.

Embodiment 47. The method of any one of embodiments 1-46, wherein electrically stimulating the splenic nerve occurs in response to a trigger signal.

Embodiment 48. The method of embodiment 47, wherein the trigger signal is encoded in the ultrasonic waves received by the device.

Embodiment 49. The method of embodiment 47 or 48, wherein the trigger signal is based on splenic nerve activity.

Embodiment 50. The method of any one of embodiments 47-49, wherein the trigger signal is based on a deviation from a baseline splenic nerve activity.

Embodiment 51. The method of any one of embodiments 49 or 50, wherein the splenic nerve activity is monitored by the implanted device.

Embodiment 52. The method of any one of embodiments 47-51, wherein the trigger signal is based on a measured physiological condition.

Embodiment 53. The method of embodiment 52, wherein the physiological condition is a temperature, a pulse rate, or a blood pressure.

Embodiment 54. The method of embodiment 52 or 53, wherein the physiological condition is measured by the implanted device.

Embodiment 55. The method of any one of embodiments 51-53, comprising emitting an ultrasonic backscatter encoding information related to the splenic nerve activity or the physiological condition.

Embodiment 56. The method of embodiment 55, wherein the ultrasonic backscatter encoding the information related to the splenic nerve activity or the physiological condition is received by an external device.

Embodiment 57. The method of embodiment 55 or 56, wherein the ultrasonic backscatter further encodes information related to the status of the device or one or more electrical pulses emitted by the device.

Embodiment 58. The method of any one of embodiments 56 or 57, comprising transmitting, at the external device, ultrasonic waves that encode the trigger signal.

Embodiment 59. The method of any one of embodiments 1-58, wherein the implanted device is fully implanted with in the perivascular fascia surrounding the splenic nerve and splenic artery.

Embodiment 60. The method of any one of embodiments 1-59, further comprising administering to the subject an anti-cancer drug.

Embodiment 61. The method of any one of embodiments 1-60, wherein the subject is a human.

Embodiment 62. An implantable device configured to perform the method of any one of embodiments 1-61.

Embodiment 63. An implantable device comprising two or more electrodes configured to be in electrical communication with a splenic nerve of a subject.

Embodiment 64. An implantable device comprising two or more electrodes configured to be in electrical communication with a splenic nerve of a subject with cancer, the device configured to electrically stimulate the splenic nerve sufficient to modulate the immune system of the subject.

Embodiment 65. An implantable device comprising two or more electrodes configured to be in electrical communication with a splenic nerve of a subject with a cancer, the device configured to electrically stimulate the splenic nerve sufficient to treat the cancer.

Embodiment 66. The device of any one of embodiments 63-65, wherein the device is configured to activate one or more immune cells in the subject upon electrically stimulating the splenic nerve.

Embodiment 67. The device of embodiment 6, wherein the device is configured to activate natural killer (NK) cells or cytotoxic T-cells in the subject upon electrically stimulating the splenic nerve.

Embodiment 68. The device of embodiment 67, wherein the device is configured to increase circulation of or activate natural killer (NK) cells in the subject upon electrically stimulating the splenic nerve.

Embodiment 69. The device of any one of embodiments 63-68, wherein the device is configured to increase a blood concentration of an inflammatory cytokine in the subject upon electrically stimulating the splenic nerve.

Embodiment 70. The device of any one of embodiments 63-68, wherein the device is configured to decrease a blood concentration of an inflammatory cytokine in the subject upon electrically stimulating the splenic nerve.

Embodiment 71. The device of embodiment 69 or 70, wherein the inflammatory cytokine is tumor necrosis factor alpha (TNF-α), interleukin-6 (IL-6), interleukin-1β (IL-1β), interleukin-2 (IL-2) vascular endothelial growth factor (VEGF), interferon-γ (IFN-γ), granulocyte colony-stimulating factor (G-SCF), interleukin-10 (IL-10), or RANTES.

Embodiment 72. The device of embodiment 69 or 70, wherein the inflammatory cytokine is a pro-inflammatory cytokine.

Embodiment 73. The device of embodiment 72, wherein the pro-inflammatory cytokine is tumor necrosis factor alpha (TNF-α), interleukin-6 (IL-6), or interleukin-1β (IL-1β).

Embodiment 74. The device of embodiment 69 or 70, wherein the inflammatory cytokine is an anti-inflammatory cytokine Embodiment 75. The device of embodiment 74, wherein the anti-inflammatory cytokine is interleukin-10 (IL-10).

Embodiment 76. The device of any one of embodiments 63-68, wherein the device is configured to increase inflammation in the subject upon electrically stimulating the splenic nerve.

Embodiment 77. The device of embodiment 76, wherein the device is configured to increase a blood concentration of a pro-inflammatory cytokine in the subject upon electrically stimulating the splenic nerve.

Embodiment 78. The device of embodiment 77, wherein the pro-inflammatory cytokine is tumor necrosis factor alpha (TNF-α), interleukin-6 (IL-6), or interleukin-1β (IL-1β).

Embodiment 79. The device of embodiment 77 or 78, wherein the device is configured to decrease a blood concentration of an anti-inflammatory cytokine in the subject upon electrically stimulating the splenic nerve.

Embodiment 80. The device of embodiment 79, wherein the anti-inflammatory cytokine is interleukin-10 (IL-10).

Embodiment 81. The device of any one of embodiments 76-80, wherein the device is configured to increase a blood concentration of tumor necrosis factor alpha (TNF-α) and reducing a blood concentration of interleukin-10 (IL-10) in the subject upon electrically stimulating the splenic nerve.

Embodiment 82. The device of any one of embodiments 76-81, wherein the device is configured to electrically stimulate the splenic nerve with a plurality of electrical pulses emitted at a frequency of about 25 Hz or higher.

Embodiment 83. The device of any one of embodiments 76-82, wherein the device is configured to electrically stimulate the splenic nerve with a plurality of electrical pulses emitted at a frequency of about 30 Hz to about 100 Hz.

Embodiment 84. The device of any one of embodiments 76-83, wherein the device is configured to electrically stimulate the splenic nerve using a plurality of biphasic electrical pulses comprising an anodal phase followed by a cathodal phase.

Embodiment 85. The device of any one of embodiments 63-68, wherein the device is configured to reduce inflammation in the subject upon electrically stimulating the splenic nerve.

Embodiment 86. An implantable device comprising two or more electrodes configured to be in electrical communication with a splenic nerve of a subject with cancer, the device configured to electrically stimulate the splenic nerve sufficient to modulate the immune system of the subject to reduce inflammation in the subject.

Embodiment 87. The device of embodiment 85 or 86, wherein the inflammation is associated with pain, fever, non-cancerous tissue necrosis, or shock.

Embodiment 88. The device of any one of embodiments 85-87, wherein the device is configured to increase a blood concentration of an anti-inflammatory cytokine in the subject upon electrically stimulating the splenic nerve.

Embodiment 89. The device of embodiment 88, wherein the anti-inflammatory cytokine is interleukin-10 (IL-10).

Embodiment 90. The device of any one of embodiments 85-89, wherein the device is configured to reduce a blood concentration of a pro-inflammatory cytokine in the subject upon electrically stimulating the splenic nerve.

Embodiment 91. The device of embodiment 90, wherein the pro-inflammatory cytokine is tumor necrosis factor alpha (TNF-α), interleukin-6 (IL-6), or interleukin-1β (IL-1β).

Embodiment 92. The device of any one of embodiments 85-91, wherein the device is configured to reduce a blood concentration of tumor necrosis factor alpha (TNF-α) and increase a blood concentration of interleukin-10 (IL-10) in the subject upon electrically stimulating the splenic nerve.

Embodiment 93. The device of any one of embodiments 85-92, wherein the wherein the device is configured to electrically stimulate the splenic nerve with a plurality of electrical pulses emitted at a frequency of less than 25 Hz.

Embodiment 94. The device of any one of embodiments 85-93, wherein the device is configured to electrically stimulate the splenic nerve with a plurality of electrical pulses emitted at a frequency of about 3 Hz to about 20 Hz.

Embodiment 95. The device of any one of embodiments 85-94, wherein the device is configured to electrically stimulate the splenic nerve using a plurality of biphasic electrical pulses comprising a cathodal phase followed by an anodal phase.

Embodiment 96. An implantable device comprising:
two or more electrodes configured to be in electrical communication with a splenic nerve of a subject;
a nerve cuff configured to at least partially wrap around the splenic nerve or a splenic neurovascular bundle; and
an integrated circuit configured to operate the two or more electrodes to emit a plurality of electrical pulses in a predetermined pattern associated with treating cancer in a subject when the plurality of electrical pulses in said predetermined pattern are used to stimulate the splenic nerve of the subject.

Embodiment 97. The device of embodiment 96, wherein the predetermined pattern is associated with causing an increase in the circulation or activation of NK cells or cytotoxic T cells in a subject when the plurality of electrical pulses in said predetermined pattern are used to stimulate the splenic nerve of the subject.

Embodiment 98. The device of embodiment 96, wherein the predetermined pattern is associated with causing an increase in the circulation or activation of NK cells in a subject when the plurality of electrical pulses in said predetermined pattern are used to stimulate the splenic nerve of the subject.

Embodiment 99. The device of any one of embodiments 96-98, wherein the predetermined pattern is associated with causing an increase in a blood concentration of an inflammatory cytokine in a subject when the plurality of electrical pulses in said predetermined pattern are used to stimulate the splenic nerve of the subject.

Embodiment 100. The device of any one of embodiments 96-98, wherein the predetermined pattern is associated with causing a decrease in a blood concentration of an inflammatory cytokine in a subject when the plurality of electrical pulses in said predetermined pattern are used to stimulate the splenic nerve of the subject.

Embodiment 101. The device of embodiment 99 or 100, wherein the inflammatory cytokine is a pro-inflammatory cytokine.

Embodiment 102. The device of embodiment 101, wherein the pro-inflammatory cytokine is tumor necrosis factor alpha (TNF-α), interleukin-6 (IL-6), or interleukin-1β (IL-1β).

Embodiment 103. The device of embodiment 99 or 100, wherein the inflammatory cytokine is an anti-inflammatory cytokine.

Embodiment 104. The device of embodiment 103, wherein the anti-inflammatory cytokine is interleukin-10 (IL-10).

Embodiment 105. The device of any one of embodiments 96-98, wherein the predetermined pattern is associated with causing increased inflammation in a subject when the plurality of electrical pulses in said predetermined pattern are used to stimulate the splenic nerve of the subject.

Embodiment 106. The device of embodiment 105, wherein the predetermined pattern is associated with causing an increase in a blood concentration of a pro-inflammatory cytokine and/or a decrease in a blood concentration of an anti-inflammatory cytokine in a subject when the plurality of electrical pulses in said predetermined pattern are used to stimulate the splenic nerve of the subject.

Embodiment 107. The device of any one of embodiments 96-98, wherein the predetermined pattern is associated with causing decreased inflammation in a subject when the plurality of electrical pulses in said predetermined pattern are used to stimulate the splenic nerve of the subject.

Embodiment 108. The device of any one of embodiments 96-98, wherein the predetermined pattern is associated with causing an increase in a blood concentration of an anti-inflammatory cytokine and/or a decrease in a blood concentration of a pro-inflammatory cytokine in a subject when the plurality of electrical pulses in said predetermined pattern are used to stimulate the splenic nerve of the subject.

Embodiment 109. The device of embodiment 106 or 108, wherein the pro-inflammatory cytokine is tumor necrosis factor alpha (TNF-α), interleukin-6 (IL-6), or interleukin-1β (IL-1β).

Embodiment 110. The device of any one of embodiments 106, 108, and 109, wherein anti-inflammatory cytokine is interleukin-10 (IL-10).

Embodiment 111. The device of any one of embodiments 96-110, wherein the controller is configured to select a mode of operation from a plurality of operation modes comprising:
- a first mode of operation that provides a plurality of electrical pulses in a predetermined inflammatory pattern associated with causing increased inflammation in a subject when the plurality of electrical pulses in said predetermined inflammatory pattern are used to stimulate the splenic nerve of the subject; and
- a second mode of operation that provides a plurality of electrical pulses in a predetermined anti-inflammatory pattern associated with causing decreased inflammation in a subject when the plurality of electrical pulses in said predetermined inflammatory pattern are used to stimulate the splenic nerve of the subject.

Embodiment 112. The device of embodiment 111, wherein the mode of operation is selected based on a trigger signal.

Embodiment 113. The device of embodiment 112, wherein the trigger signal is based on splenic nerve activity.

Embodiment 114. The device of embodiment 112, wherein the device comprises a wireless communication system, and is configured to wirelessly receive the trigger signal.

Embodiment 115. The device of any one of embodiments 63-81, 96-106, and 111-114, wherein the device is configured to provide, using at least one of the two or more electrodes, a plurality of electrical pulses emitted at a frequency of about 25 Hz or higher.

Embodiment 116. The device of any one of embodiments 63-81, 96-106, and 111-115, wherein the device is configured to provide, using at least one of the two or more electrodes, a plurality of electrical pulses emitted at a frequency between about 30 Hz and about 100 Hz.

Embodiment 117. The device of any one of embodiments 63-81, 96-106, and 109-116, wherein the device is configured to provide, using at least one of the two or more electrodes, a plurality of biphasic electrical pulses comprising an anodal phase followed by a cathodal phase.

Embodiment 118. The device of any one of embodiments 63-71, 85-92, 96-104, and 107-114, wherein the device is configured to provide, using at least one of the two or more electrodes, a plurality of electrical pulses emitted at a frequency of less than 25 Hz.

Embodiment 119. The device of any one of embodiments 63-71, 85-92, 96-104, 107-114, and 118, wherein the device is configured to provide, using at least one of the two or more electrodes, a plurality of electrical pulses emitted at a frequency of about 3 Hz to about 20 Hz.

Embodiment 120. The device of any one of embodiments 63-71, 85-92, 96-104, 107-114, 118 and 19, wherein the device is configured to provide, using at least one of the two or more electrodes, a plurality of biphasic electrical pulses comprising a cathodal phase followed by an anodal phase.

Embodiment 121. The device of any one of embodiments 63-120, wherein the device is configured to electrically stimulate the splenic nerve using one or more electrical pulses about 1 ms in length or less.

Embodiment 122. The device of any one of embodiments 63-120, wherein the device is configured to provide, using at least one of the two or more electrodes, one or more electrical pulses about 1 ms in length or less.

Embodiment 123. The device of any one of embodiments 63-122, wherein the device is configured to electrically stimulate the splenic nerve using one or more electrical pulses having an amplitude of about 250 µA to about 10 mA.

Embodiment 124. The device of any one of embodiments 63-122, wherein t the device is configured to provide, using at least one of the two or more electrodes, one or more electrical pulses having an amplitude of about 250 µA to about 10 mA.

Embodiment 125. The device of any one of embodiments 63-124, wherein the device is configured to electrically stimulate the splenic nerve using one or more electrical pulses at a frequency of about 100 Hz or less.

Embodiment 126. The device of any one of embodiments 63-125, wherein the device is configured to electrically stimulate the splenic nerve using a pulse train comprising a plurality of biphasic electrical pulses.

Embodiment 127. The device of any one of embodiments 63-125, wherein the device is configured to provide, using at least one of the two or more electrodes, a plurality of biphasic electrical pulse Embodiment 128. The device of embodiment 126 or 127, wherein the biphasic electrical pulses comprises an anodal phase followed by a cathodal phase.

Embodiment 129. The device of embodiment 126 or 127, wherein the biphasic electrical pulses comprises a cathodal phase followed by an anodal phase.

Embodiment 130. The device of any one of embodiment 63-129, wherein the device is configured to electrically stimulate the splenic nerve using a plurality of pulse trains comprising two or more electrical pulses, the pulse trains separated by a dwell time of about 50 ms or more.

Embodiment 131. The device of any one of embodiment 63-129, wherein the device is configured to provide, using at least one of the two or more electrodes, a plurality of pulse trains comprising two or more electrical pulses, the pulse trains separated by a dwell time of about 50 ms or more.

Embodiment 132. The device of embodiment 130 or 131, wherein the dwell time is about 50 ms to about 2 minutes.

Embodiment 133. The device of any one of embodiments 130-132, wherein the dwell time is about 500 ms or more.

Embodiment 134. The device of any one of embodiments 130-133, wherein the plurality of pulse trains comprises at least a first pulse train followed by a second pulse train, wherein electrical pulses in the first pulse train have an amplitude lower than an amplitude of electrical pulses in the second pulse train.

Embodiment 135. The device of any one of embodiments 63-129, wherein the splenic nerve is electrically stimulated using tonic electrical pulses.

Embodiment 136. The device of any one of embodiments 63-129, wherein the device is configured to provide, using at least one of the two or more electrodes, tonic electrical pulses.

Embodiment 137. The device of any one of embodiments 63-136, further comprising a nerve cuff configured to position at least one of the two or more electrodes in electrical communication with the splenic nerve.

Embodiment 138. The device of embodiment 137, wherein the nerve cuff is a helical nerve cuff configured to at least partially wrap around the splenic neurovascular bundle.

Embodiment 139. The device of any one of embodiments 63-138, further comprising a body comprising a wireless communication system attached to the nerve cuff.

Embodiment 140. The device of embodiment 139, wherein the body is positioned on an outer surface of the helical nerve cuff.

Embodiment 141. The device of any one of embodiments 63-140, further comprising a wireless communication system.

Embodiment 142. The device of any one of embodiments 63-141, comprising an ultrasonic transducer configured to:
receive ultrasonic waves; and
convert energy from the ultrasonic waves into electrical energy that powers the device.

Embodiment 143. The device of any one of embodiments 63-142, wherein the device is configured to electrically stimulate the splenic nerve in response to a trigger signal.

Embodiment 144. The device of any one of embodiments 63-143, wherein the device is configured to provide a plurality of electrical pulses, using at least one of the two or more electrodes, in response to a trigger signal.

Embodiment 145. The device of embodiment 143 or 144, wherein the trigger signal is wirelessly received by the device.

Embodiment 146. The device of any one of embodiments 143-145, wherein the trigger signal is encoded in ultrasonic waves received by the device.

Embodiment 147. The device of any one of embodiments 143-146, wherein the trigger signal is based on splenic nerve activity.

Embodiment 148. The device of any one of embodiments 143-147, wherein the trigger signal is based on a deviation from a baseline splenic nerve activity.

Embodiment 149. The device of any one of embodiments 143-148, wherein the trigger signal is based on a measured physiological condition.

Embodiment 150. The device of any one of embodiments 63-149, wherein the device comprises a sensor configured to measure a physiological condition.

Embodiment 151. The device of embodiment 150, wherein the physiological condition is a temperature, a pulse rate, or a blood pressure.

Embodiment 152. The device of any one of embodiments 63-151, wherein the device is configured to monitor splenic nerve activity.

Embodiment 153. The device of any one of embodiments 63-152, wherein the device is configured to emit backscatter waves encoding information related to the splenic nerve activity or the physiological condition.

Embodiment 154. The device of embodiment 153, wherein the backscatter waves encoding the information related to the splenic nerve activity or the physiological condition are configured to be received by an external device.

Embodiment 155. The device of embodiment 153 or 154, wherein the backscatter waves further encodes information related to the status of the device or one or more electrical pulses emitted by the device.

Embodiment 156. The device of any one of embodiments 153-155, wherein the backscatter waves are ultrasonic backscatter waves.

Embodiment 157. The device of any one of embodiments 62-156, wherein the implanted device has a volume of about 5 mm$^3$ or smaller.

Embodiment 158. A system, comprising the device of any one of embodiments 62-157, and an interrogator comprising a wireless communication system configured to wirelessly communication or power the device.

EXAMPLES

The application may be better understood by reference to the following non-limiting examples. The following examples are presented in order to more fully illustrate the application and should in no way be construed as limiting the scope of the application. While certain examples of the present application have been shown and described herein, it will be obvious that such examples are provided by way of example only. Numerous variations, changes, and substitutions may occur to those skilled in the art without departing from the spirit and scope of the invention. It should be understood that various alternatives to the examples described herein may be employed in practicing the methods described herein.

Example 1: Stimulation of Splenic Nerve to Modulate Immune System

In this example, splenic nerve stimulation was used as a method to reduce the inflammatory response to an acute immune challenge, triggered by intravenous infusion of lipopolysaccharides (LPS). Adult male and female Lewis rats, weighing approximately 250-400 grams, were sourced from Charles River Laboratories in Wilmington, MA. Rats were housed in pairs on a 12-hour light/dark cycle and fed ad libitum. All experiments were performed according to local Animal Care and Use Committee guidelines.

Animals were fully anesthetized with isoflurane gas mixed with pure oxygen using a digital vaporizer (Kent Scientific. Torrington, CT). Animals were placed in the supine position, a rectal thermometer was inserted to monitor core temperature and control an infrared heating pad, and a pulse oximeter (Kent Scientific, Torrington, CT) was clipped to the right front paw to monitor oxygen saturation. Fur around the left flank and abdomen was clipped. The left femoral artery and vein were catheterized using medical-grade micro-urethane tubing (Scientific Commodities. Inc., Lake Havasu City, AZ), and catheters were locked with a solution of 50 U/ml sodium heparin from porcine intestinal mucosa (Sigma-Aldrich. St. Louis, MO). The arterial line was connected to a pressure transducer (Stoelting, Wood Dale, IL) in order to capture the arterial pressure waveform, and the venous line was used as an infusion and withdrawal point in later steps.

A midline laparotomy was performed in order to gain access to the abdominal cavity. The splenic neurovascular bundle was identified, and a segment was chosen in between the proximal origin from the celiac artery and the distal point at which the artery branches before entering the hilum of the spleen. A roughly 3 mm section of artery along with its accompanying splenic nerve branches was gently isolated from the vein and surrounding tissue and placed into a nerve cuff containing 3×50 μm-wide platinum electrodes spaced 1 mm apart (Microprobes, Inc., Gaithersburg, MD). A custom-fabricated counter electrode, made from a 3 mm×3 mm square of 0.004" platinum sheet, was placed nearby in contact with the pancreatic tissue a few millimeters away from the cuff. Finally, Ag/Cl pellet ground electrode (WPI, Sarasota, FL) was placed in the abdominal cavity.

In order to verify that the nerve cuff electrodes were in electrical contact with the splenic nerves, the three electrodes of the cuff and the ground electrode were connected in pseudo-tripolar configuration to a differential amplifier (A-M systems, Sequim, WA). Signals were amplified 1000× and bandpass filtered between 100 Hz and 5 kHz, and viewed on a digital oscilloscope (Tektronix. Beaverton, OR). The presence of spontaneous sympathetic nerve activity was used as an indicator that the cuff was placed correctly and that the nerves had not been injured by the surgical procedure. Stable nerve activity was monitored for 15 minutes before continuing to the next phase of the procedure.

Following verification of proper electrode placement, the splenic nerve was stimulated using a constant-current isolated pulse stimulator (A-M Systems, Sequim. WA). The positive terminal of the stimulator was connected to the counter electrode, and the negative terminal was connected to the middle electrode of the nerve cuff. Pulses were monopolar, cathodal-first, biphasic, square-wave pulses with the following parameters: 300 µs pulse length (150 µs cathodal phase, 60 µs inter-phase interval, 150 µs anodal phase), pulse amplitudes between 1 and 1.8 mA, and at an average frequency of 5 Hz over a 20 min period. A total of 27 rats received the stimulatory pulses (23 rats received tonic 5 Hz pulses, and 4 rats received "burst" simulations with pulse trains being separated by a dwell time with an average frequency of 5 Hz), and 24 rats received no stimulatory pulse (control).

In order to trigger an innate immune reaction, a sub-lethal dose of lipopolysaccharides (LPS) from *E. coli* (Sigma-Aldrich, St. Louis. MO) was infused at a concentration of 60 µg/kg in a 500 µl bolus of saline through the venous catheter, 10 minutes after the end of stimulation. LPS was prepared fresh daily from 1 mg/ml aliquots frozen at −20° C.

Approximately 200 µl of blood was drawn from the venous catheter at the following intervals: "baseline", which corresponded to the end of the 15-min spontaneous recording period and immediately prior to the onset of stimulation, and then 45, 90, 135, and 180 min after infusion of LPS. Blood was allowed to clot for 30 min at room temperature, and then centrifuged for 20 min, after which the serum was immediately extracted and frozen at −20° C. until further analysis.

Serum cytokine (TNF-α and IL-1β) levels were determined using quantitative ELISA kits (R&D systems. Minneapolis, MN) according to manufacturer instructions. Fluorescence absorption was measured using a 96-well plate reader (Thermo-Fisher Scientific, Waltham, MA). A 4-parameter logistic regression curve was used to compute cytokine concentrations in samples by fitting the curve to known standard samples supplied by the manufacturer.

Figure 14A:
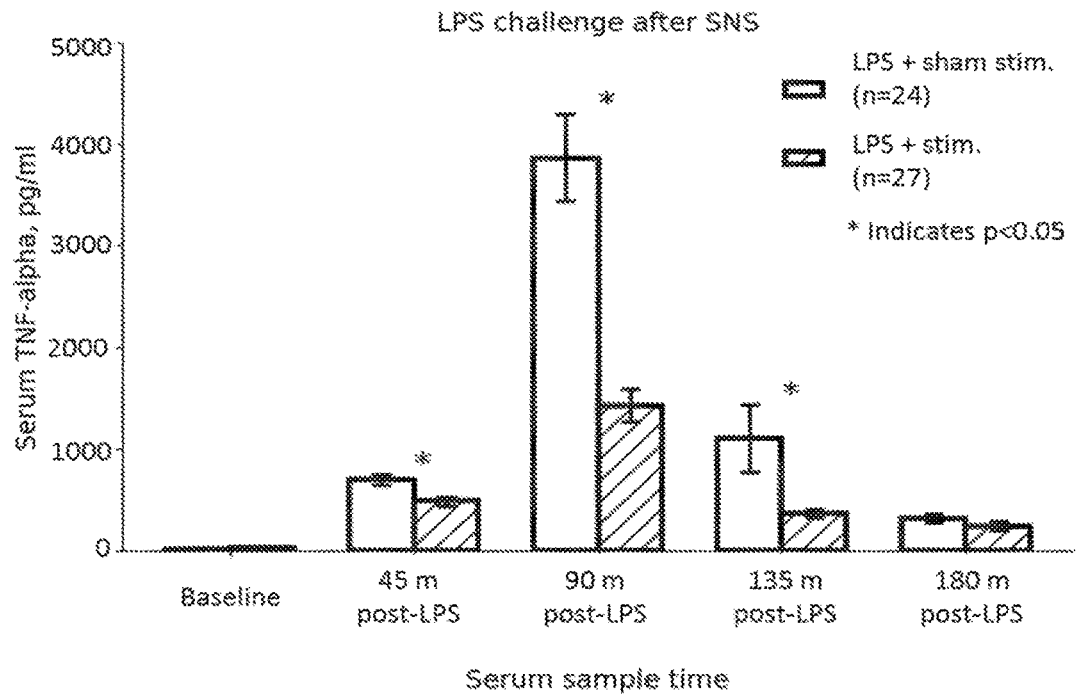
FIG. 14A and FIG. 14B show the TNF-α (FIG. 14A and FIG. 14C) and IL-1β (FIG. 14B) serum concentration in rats with or without stimulation of the splenic nerve for 20 minutes using monopolar, cathodal-first, biphasic, square-wave pulses 300 μs in length (150 μs cathodal phase and 150 μs anodal phase, with a 60 μs inter-phase interval), 1.8 mA pulse amplitude, and with a 200 ms dwell time between the biphasic pulses. Rats were infused with 60 μg/ml I.V. LPS at time 0 to trigger an immune reaction.
Figure 14B:
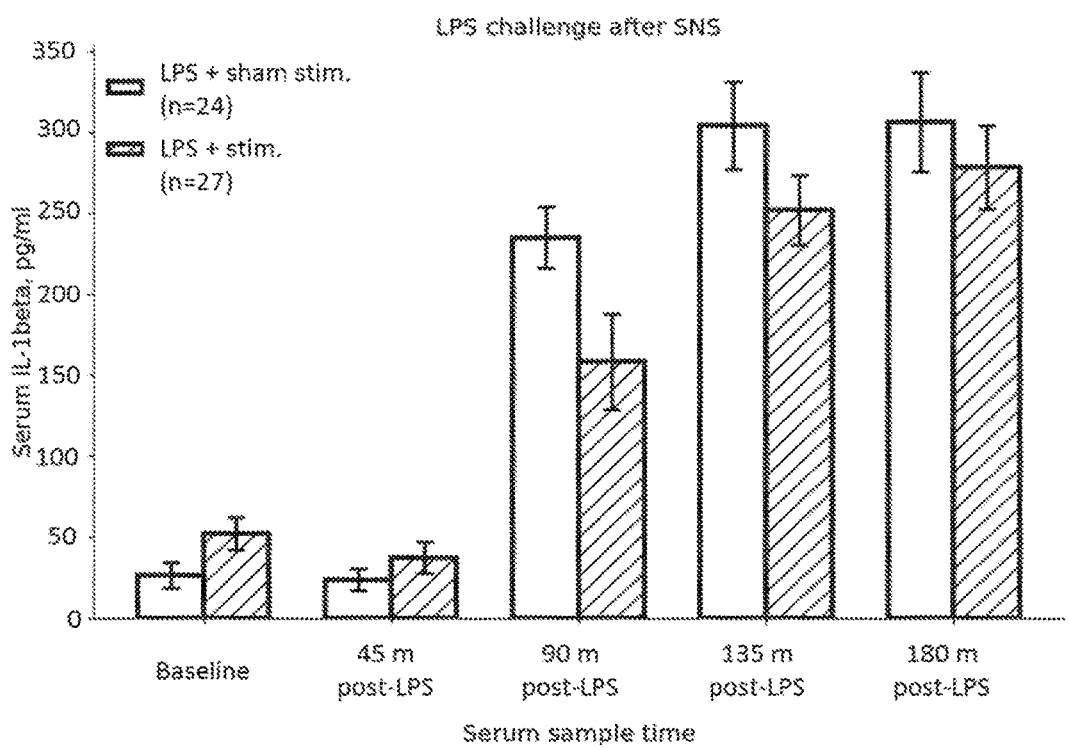

Serum concentration of TNF-α and IL-1β measured in each sample is shown relative to the onset of LPS infusion in FIG. 14A and FIG. 14B, respectively. In FIG. 14B, only animals receiving tonic stimulation pulses between 1.5 mA and 1.8 mA are shown, as lower amplitude stimulation did not appear to influence IL-1β levels. TNF-α serum concentration in both cohorts peaked about 90 minutes following LPS administration. The immune suppressing nerve stimulation resulted in a substantial decrease of peak TNF-α serum concentration compared to the serum concentration in rats that did not receive the immune suppressing nerve stimulation (3872 pg/ml versus 1424 pg/ml, respectively). IL-1β serum concentration continued to increase during the 180 minutes experiment, although IL-1β serum concentration in rats that received the immune suppressing nerve stimulation was lower than the IL-1β serum concentration in rats that did not receive the immune suppressing nerve stimulation (292 pg/ml versus 296 pg/ml after 180 minutes, respectively).

Figure 14C:
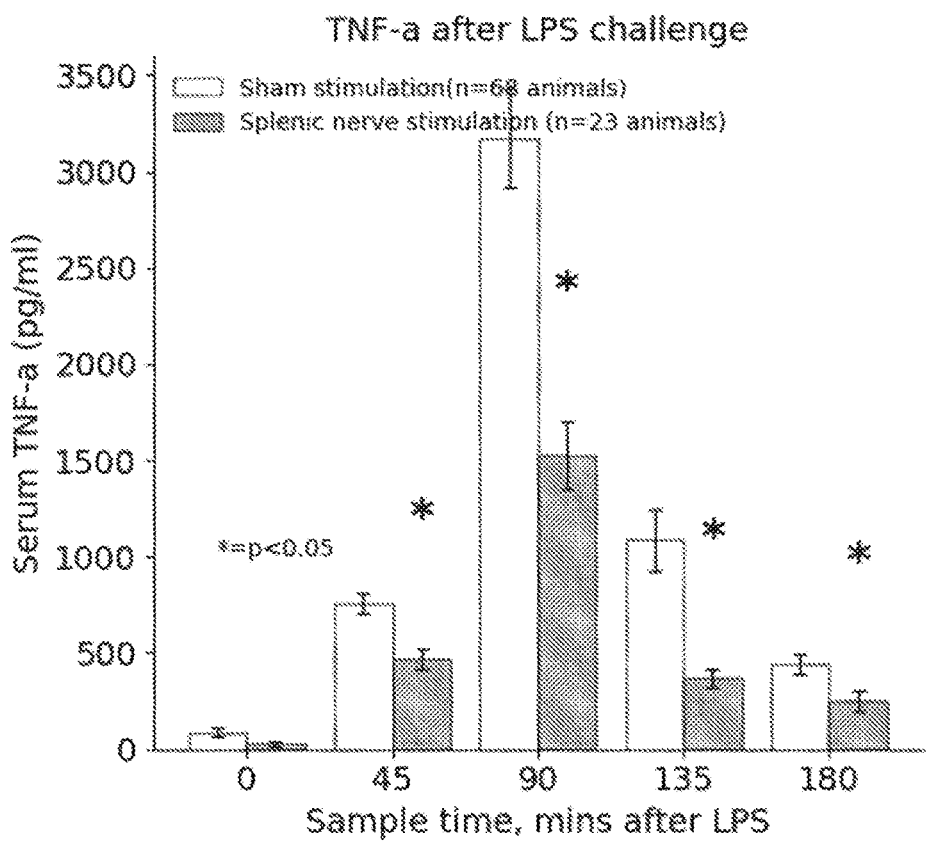

Further analysis was conducted on the 23 rats receiving the tonic 5 Hz electrical pulses. Data was also collected for 44 additional control rats (total n=68). Serum concentration of TNF-α measured in each sample for this selection of rats is shown relative to the onset of LPS infusion in FIG. 14C. TNF-α serum concentration in both cohorts peaked about 90 minutes following LPS administration. The immune suppressing nerve stimulation resulted in a substantial decrease of peak TNF-α serum concentration compared to the serum concentration in rats that did not receive the immune suppressing nerve. Levels of TNF-α in the stimulation group were significantly lower (P<0.05, student's T-test) at the 45, 90, 135, and 180 minute time points relative to sham animals.

Example 2: Splenic Nerve Stimulation-Response Curve and Stimulation Response Efficiency In order to test the efficacy of different stimulation pulse parameters for eliciting an evoked compound action potential (CAP) in the splenic nerve, the splenic neurovascular bundle was exposed and cuff electrodes were implanted for a cohort of rats as described in Example 1. Two approximately 3-mm lengths of nerve/artery complex were identified for electrode placement: A proximal location was chosen to be immediately distal to the branch point of the splenic nerve and artery from the celiac artery. A distal location was chosen to be immediately proximal to the point at which the splenic artery splits into several branches before entering the hilum of the spleen. This was done to maximize the distance between recording and stimulating electrodes in order to ensure that the neural response would not be obscured by the stimulus artifact. Typical separation between the proximal and distal locations was between 10 and 15 mm. A cuff electrode for stimulation was placed at the proximal location, while a cuff electrode for recording was placed at the distal location. Stimulation cathodal-first, biphasic, square-wave pulses of varying parameters (pulse length and/or amplitude) were delivered at the stimulating electrodes, and the evoked CAP was measured and recorded at the recording electrodes. For each set of parameters, we generated a recruitment curve by determining the minimum amplitude pulse (in mA) necessary to evoke a measurable CAP (in µV), and then increasing the amplitude in a stepwise manner until the peak-to-peak amplitude of the CAP no longer grew with increased pulse amplitude—the saturation point at which the stimulation pulses were activating all of the axons in the nerve. For each pulse amplitude level, the splenic nerve was stimulated with 100 pulses, and the average CAP of those 100 trials was used to compute the peak-to-peak response. A direct comparison of the efficiency of each set of parameters in terms of the amount of charge required to evoke a given amplitude CAP from the nerve can be compared in this manner, as the charge delivered by a square current pulse is the product of the amplitude and the duration.

Figure 15A:
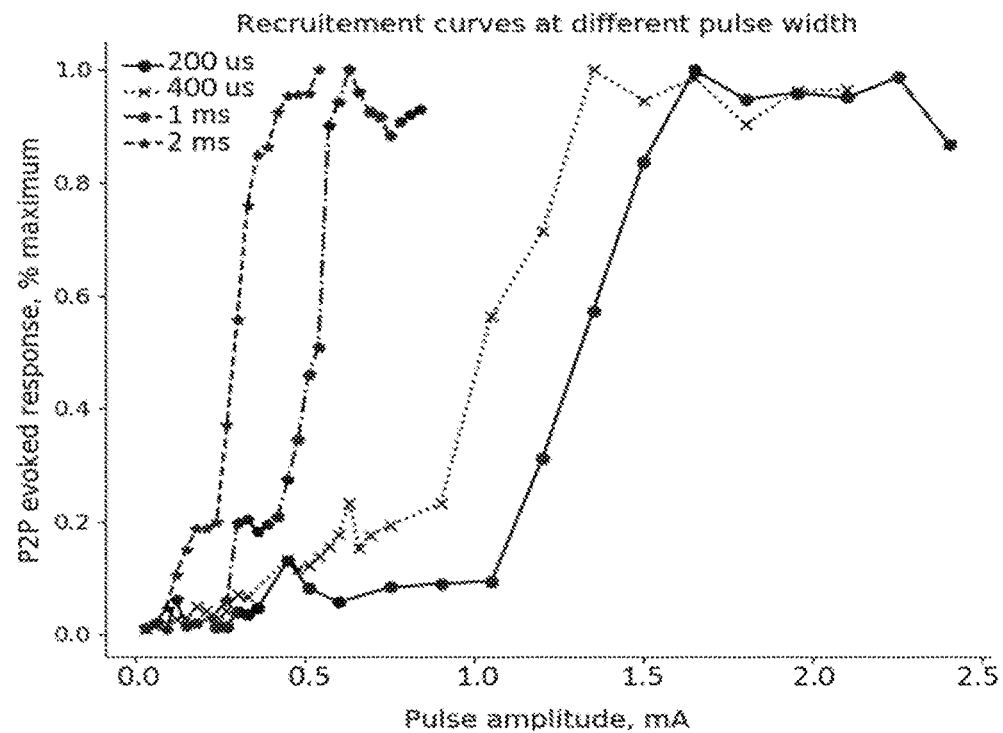
FIG. 15A shows evoked peak-to-peak (P2P) compound action potential (CAP) response upon stimulation of the splenic nerve for 2 ms, 1 ms, 400 μs, or 200 μs (split evenly between cathodal and anodal phases, with a 60 μs inter-phase interval) at various amplitude ranges (ranging from 50 μA to 2.5 mA) using cathodal-first, biphasic, square-wave pulses. Longer pulses required lower pulse amplitude to evoke the same peak-to-peak CAP response.
Figure 15B:
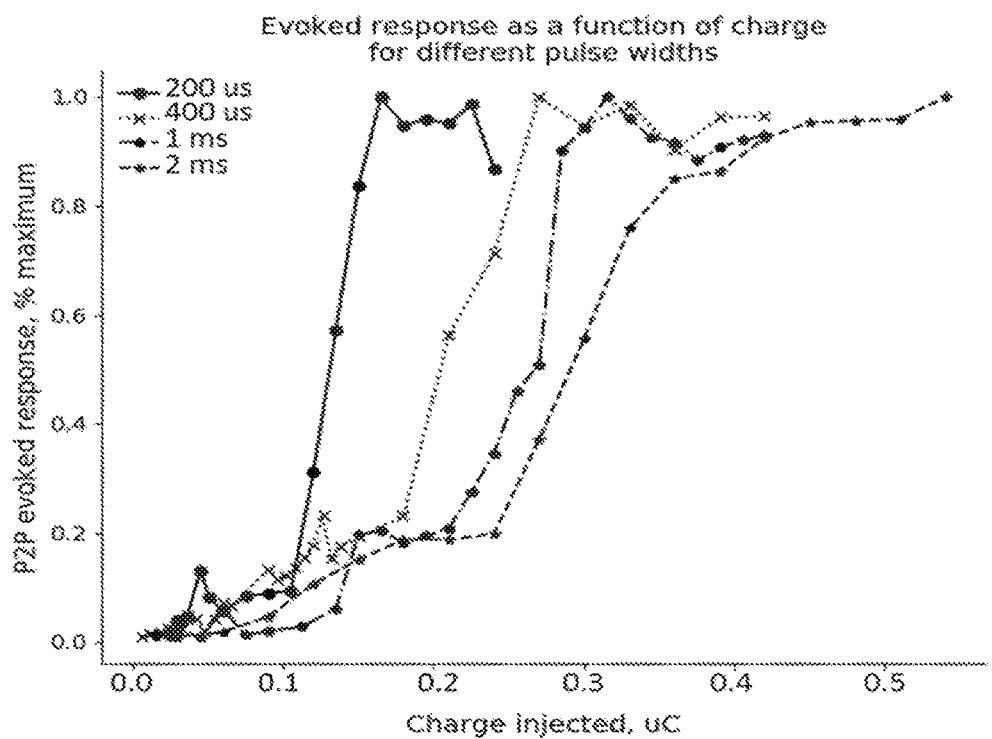
FIG. 15B shows the evokes peak-to-peak (P2P) compound action potential (CAP) response upon stimulation of the splenic nerve for 2 ms, 1 ms, 400 μs, or 200 μs (split evenly between cathodal and anodal phases, with a 60 μs inter-phase interval) at various charges (as determined by applied current amplitude and pulse length). This demonstrates the lower pulse length is more efficient when delivering a charge for a given CAP response.

In order to determine if different pulse widths had different charge efficiency, recruitment curves plotting the amplitude of evoked splenic nerve responses as a function of charge delivery for varying pulse widths were generated. It was found that for a given pulse amplitude, longer pulses elicited larger compound action potentials (CAPs) from the splenic nerve. Cathodal-first, biphasic, square-wave pulses of 200 µs, 400 µs, 1 ms, or 2 ms (split evenly between cathodal and anodal phases, with a 60 µs inter-phase interval) of varying amplitudes ranging from 50 µA to 2.5 mA were delivered at the stimulating electrodes, and the evoked CAP was measured and recorded at the recording electrodes. For a given pulse amplitude, longer pulses elicited larger CAPs from the splenic nerve (see FIG. 15A for exemplary results). However, by plotting the evoked response as a function of total charge injected at a given pulse, it can be seen that 200 µs pulses outperform longer pulse widths, as determined by the larger peak-to-peak evoked response in the detected signal. See FIG. 15B for exemplary results. Thus, delivery of a stimulatory pulse is more efficient using a shorter pulse width. The results shown in FIG. 15A and FIG. 15B were each taken from a single animal, although similar results were observed for different animals at different pulse lengths and/or amplitudes.

For stimulatory pulses with 200 μs pulse lengths, the pulse amplitude threshold for eliciting a splenic nerve response was around 1 mA and saturated around 1.8 mA, with larger amplitude pulses generating diminishing returns in terms of evoked responses.

Figure 16:
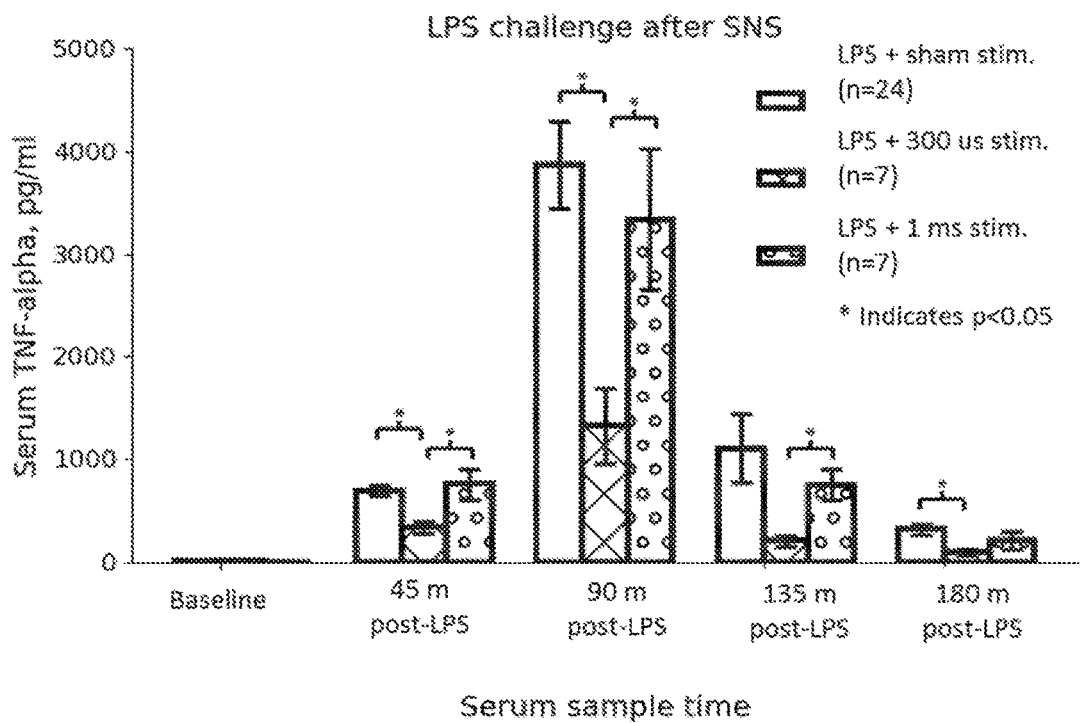
FIG. 16 shows serum TNF-α levels as a function of time after completion of 20 minutes of splenic nerve stimulation (followed by LPS infusion) using cathodal-first, biphasic 1.8 mA pulses of 300 μs (n=7) or 1 ms (n=4) (split evenly between cathodal and anodal phases, with a 60 μs inter-phase interval), or unstimulated (n=24), applied to the splenic nerve at 5 Hz. The shorter pulse length was more effective at modulating the TNF-α level of the subject.

Example 3: Splenic Nerve Stimulation Pulse Lengths for Modulation of Cytokine Release In order to test how the splenic nerve stimulatory pulse length affects modulation of serum TNF-α level in subjects after stimulation of the splenic nerve, the splenic nerve was stimulated using a series of electrical pulses in a cohort of rats. The splenic neurovascular bundle was exposed and cuff electrodes were implanted for a cohort of rats as described in Example 1. The splenic nerve of the rats was stimulated for 20 minutes using a train of 1.8 mA cathodal-first, biphasic, square-wave pulses applied at 5 pulses per second (5 Hz) using 300 μs (n=7) or 1 ms pulse lengths (n=4) (pulse lengths split evenly between cathodal and anodal phases, with a 60 μs inter-phase interval), before a 10 minute rest followed by infusing the rats with 60 μg/kg LPS in a 500 μl bolus of saline through the venous catheter to induce an immune reaction. A control cohort (n=24) was implanted with the electrodes and infused with LPS, but did not receive any stimulatory pulses. Serum TNF-α levels were measured as described in Example 1 at time points of 0 minutes, 45 minutes, 90 minutes, and 180 minutes following LPS infusion. Serum TNF-α levels as a function of time after LPS infusion and completion of stimulation is shown in FIG. 16. Stimulation with 1.8 mA pulse amplitudes was effective at reducing TNF-α release after LPS challenge when delivered with 200 μs pulse lengths, but not when 1 ms pulse lengths were used. Thus, pulse lengths were chosen in order to reduce the power needed and to generate effective stimulation.

Figure 17A:
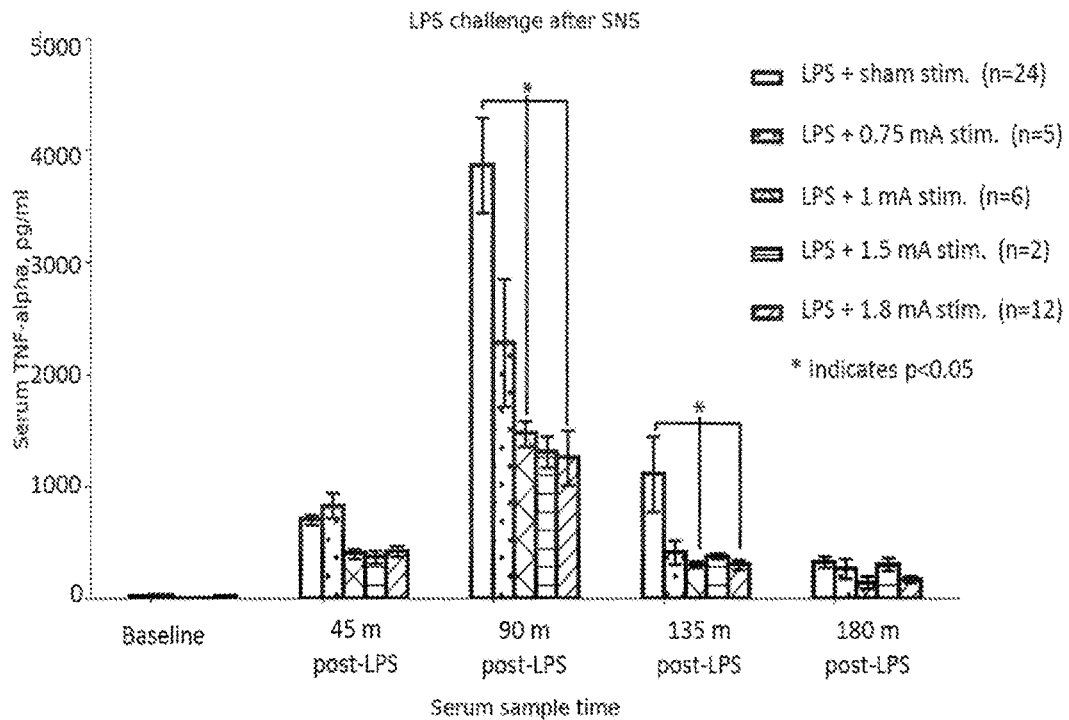
FIG. 17A shows serum TNF-α levels as a function of time after completion of 20 minutes of splenic nerve stimulation (followed by LPS infusion) using a train of cathodal-first, biphasic 300 μs pulses (split evenly between cathodal and anodal phases, with a 60 μs inter-phase interval) applied at 5 pulses per second (5 Hz) using amplitudes of 750 μA (n=5), 1.0 mA (n=6), 1.5 mA (n=2) or 1.8 mA (n=12), or unstimulated (n=24). All amplitudes were effective at reducing serum TNF-α level.

Example 4: Splenic Nerve Stimulation Pulse Amplitude for Modulation of Cytokine Release In order to test how the splenic nerve stimulatory pulse amplitude affects modulation of serum TNF-α level in subjects after stimulation of the splenic nerve, the splenic nerve was stimulated using a series of electrical pulses in a cohort of rats. The splenic neurovascular bundle was exposed and cuff electrodes were implanted for a cohort of rats as described in Example 1. The splenic nerve of the rats was stimulated for 20 minutes using a train of 300 μs cathodal-first, biphasic, square-wave pulses (split evenly between cathodal and anodal phases, with a 60 μs inter-phase interval) applied at 5 pulses per second (5 Hz) using amplitudes of 750 μA (n=5), 1.0 mA (n=4), 1.5 mA (n=2) or 1.8 mA (n=7) before a 10 minute rest followed by infusing the rats with 60 μg/kg LPS in a 500 μl bolus of saline through the venous catheter. A control cohort (n=24) was implanted with the electrodes and infused with LPS, but did not receive any stimulatory pulses. Serum TNF-α levels were measured as described in Example 1 at time points of 0 minutes, 45 minutes, 90 minutes, and 180 minutes following LPS infusion. Serum TNF-α levels as a function of time after LPS infusion and completion of stimulation is shown in FIG. 17A. All pulse amplitudes were effective in reducing the serum TNF-α levels after LPS infusion, with currents of 1 mA or more producing the most effective TNF-α reduction.

Figure 17B:
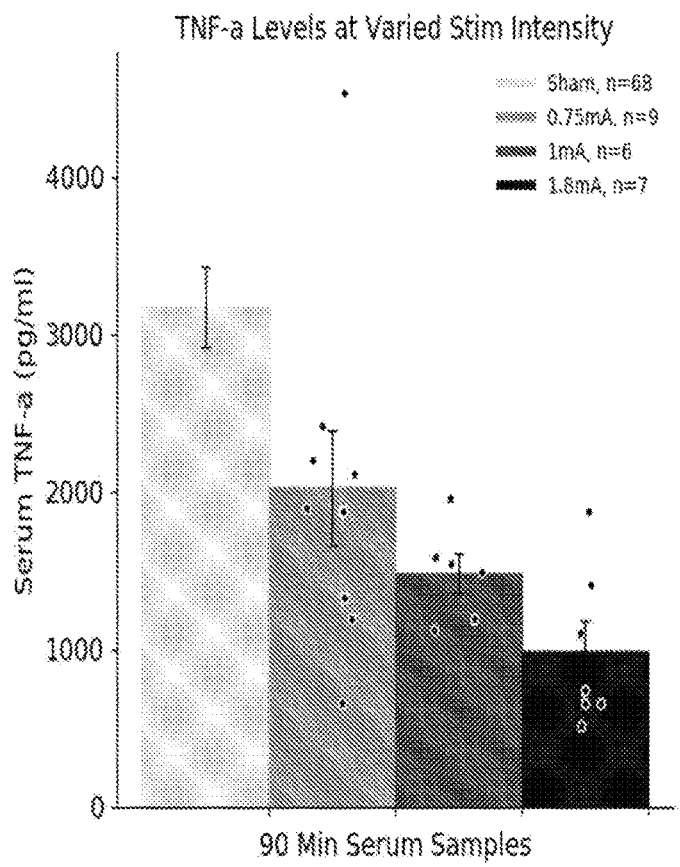
FIG. 17B shows peak serum TNF-α levels (at 90 minutes) in rats as a after infusion of 60 μg/ml I.V. LPS and completion of 20 minutes of splenic nerve stimulation using a train of cathodal-first, biphasic 300 μs pulses (split evenly between cathodal and anodal phases, with a 60 μs inter-phase interval) applied at 5 pulses per second (5 Hz) using amplitudes of 750 μA (n=9), 1.0 mA (n=6), or 1.8 mA (n=7), or unstimulated (n=68). All amplitudes were effective at reducing serum TNF-α level compared to unstimulated shams.

Additional data was collected using the same protocol, with 4 additional rats being stimulated using the 750 μA pulses (total n=9), 2 additional rats being stimulated using the 1.0 mA pulses (total n=6), and additional 44 control rats (total n=6). Serum TNF-α levels at 90 minutes after LPS infusion is shown in FIG. 17B, relative to the unstimulated (control) animals. Data for animals stimulated using 1.5 mA pulses was omitted from FIG. 17B due to low cohort size. Higher amplitude pulses were more effective at reducing TNF-α levels than lower amplitude pulses, demonstrating that the strength of the effect can be modulated with varied pulse amplitudes.

Figure 18A:
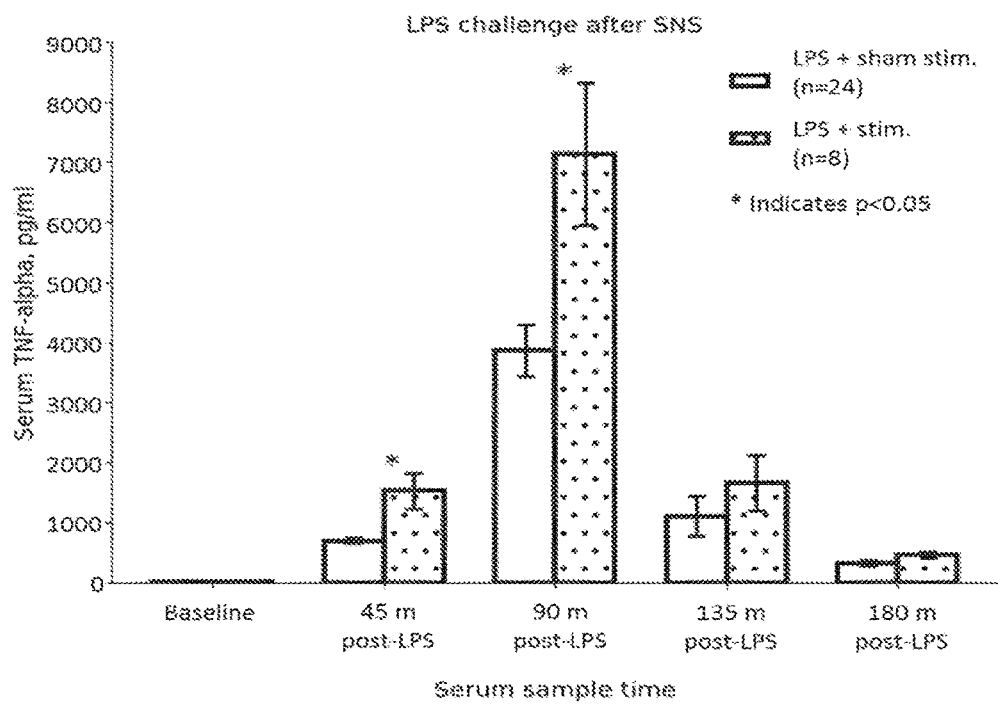
FIG. 18A shows serum TNF-α levels as a function of time starting immediately prior to the time of LPS infusion (baseline). After a 10 minute rest period following LPS administration, the splenic nerve was stimulated for 40 minutes using a train of 1.8 mA anodal-first, biphasic, square wave pulses at a rate of 30 per second (30 Hz), using a 300 μs (split evenly between cathodal and anodal phases, with a 60 μs inter-phase interval) pulse length (n=8), or unstimulated (n=24).

Example 5: Splenic Nerve Stimulation for Increase or Decrease of Cytokine Release Experiments were also conducted to demonstrate that cytokine levels (such as TNF-α levels) can also be increased by altering the stimulation parameters (e.g., pulse frequency and/or pulse polarity). In this experiment, splenic nerve stimulation was used as a method to increase the inflammatory response to an acute immune challenge triggered by IV infusion of LPS. A cohort of rats were implanted with splenic nerve stimulating electrode cuffs as described in Example 1, by placing the cuff around the splenic neurovascular bundle. The splenic nerve of the rats was stimulated for 40 minutes using a train of 1.8 mA anodal-first, biphasic, square wave pulses at a rate of 30 per second (30 Hz), using a 300 μs pulse length (n=8) (split evenly between cathodal and anodal phases, with a 60 μs inter-phase interval). The stimulation period began 10 minutes after infusing rats with 60 μg/kg LPS in a 500 μl bolus of saline through the venous catheter. A control cohort (n=24) was implanted with the electrodes and infused with LPS, but did not receive any stimulatory pulses. Serum TNF-α levels were measured as described in Example 1 at baseline (immediately before LPS administration), 45 minutes, 90 minutes, and 180 minutes following LPS infusion. Serum TNF-α levels as a function of time after LPS infusion and completion of stimulation is shown in FIG. 18A. Rats receiving splenic nerve stimulation using these parameters had significantly higher TNF-α concentrations compared to the control animals at the 45-min timepoint (1536 pg/mL compared to 686 pg/mL, respectively), as well as the 90 min-timepoint (7123 pg/mL compared to 3869 pg/mL, respectively). These data demonstrate the potential of splenic nerve stimulation to augment immune responses.

Figure 18B:
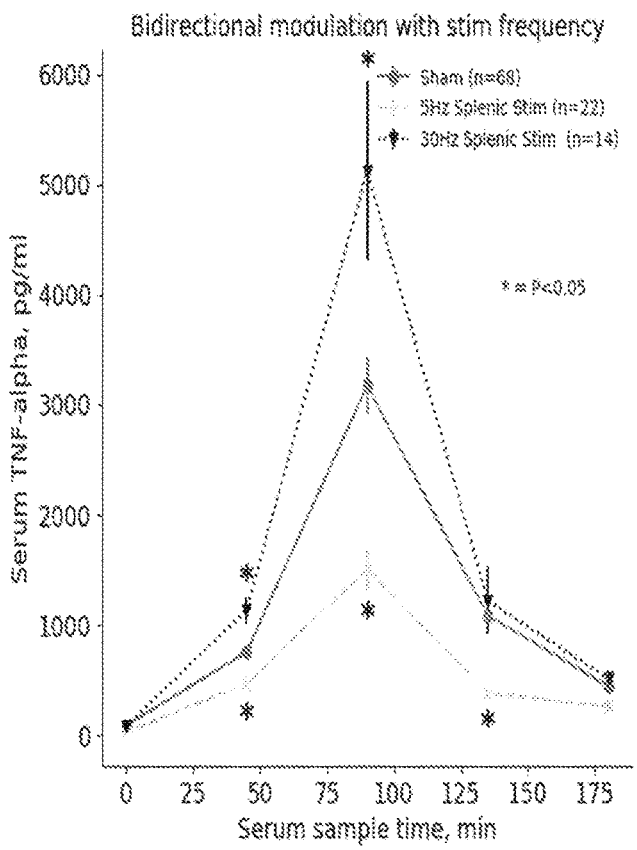
FIG. 18B shows serum TNF-α levels in 3 groups of rats as a function of time beginning immediately prior to LPS infusion (60 μg/ml I.V., time 0). After a 10 minute rest period following LPS administration, the splenic nerve in one group was stimulated using a train of anodal-first, biphasic 1.8 mA, 300 μs (split evenly between cathodal and anodal phases, with a 60 μs inter-phase interval), square wave pulses at a rate of 30 per second (30 Hz, n=14. A second group was stimulated with the same pulses, but cathodal-first biphasic and at a rate of 5 per second (5 Hz, n=22). The final group was unstimulated (sham, n=68). Asterisks indicate time points at which differences in values between the sham group and one of the stimulation groups were statistically significant.

Data for an additional 6 rats was collected using the above protocol (total n=14). For comparison, a second cohort was stimulated for 20 minutes using a train of 1.8 mA cathodal-first, biphasic, square wave pulses at a rate of 5 per second (5 Hz), using a 300 μs pulse length (split evenly between cathodal and anodal phases, with a 60 μs inter-phase interval, n=22). The stimulation period for this group began 10 minutes before infusing rats with 60 μg/kg LPS. Data for additional control animals was also collected (total n=68). Serum TNF-α levels as a function of time after LPS infusion and completion of stimulation is shown in FIG. 18B. Rats receiving splenic nerve stimulation using the 30 Hz parameters had significantly higher TNF-α concentrations compared to the control animals at the 45-min timepoint as well as the 90 min-timepoint. In contrast, animals stimulated with the 5 Hz pulse parameters showed a reduction in the serum concentration of TNF-α relative to controls, with significant differences occurring at 45, 90 and 135 minutes. These data demonstrate the potential of splenic nerve stimulation to augment immune responses as well as reduce them, depending on the choice of stimulation parameters used.

Example 6: Splenic Nerve Stimulation Pulse Pattern for Modulation of Cytokine Release In order to test how the splenic nerve stimulatory pulse pattern affects modulation of serum TNF-α level in subjects after stimulation of the splenic nerve, the splenic nerve was stimulated using a series of electrical pulses in a cohort of rats with a dwell time (i.e., a quiescent period) between pulse trains. This was compared to a tonic stimulation paradigm, which delivered pulses at a steady frequency throughout the stimulation period. The total number of pulses delivered within a 2-second period was controlled between the study groups.

Figure 19A:
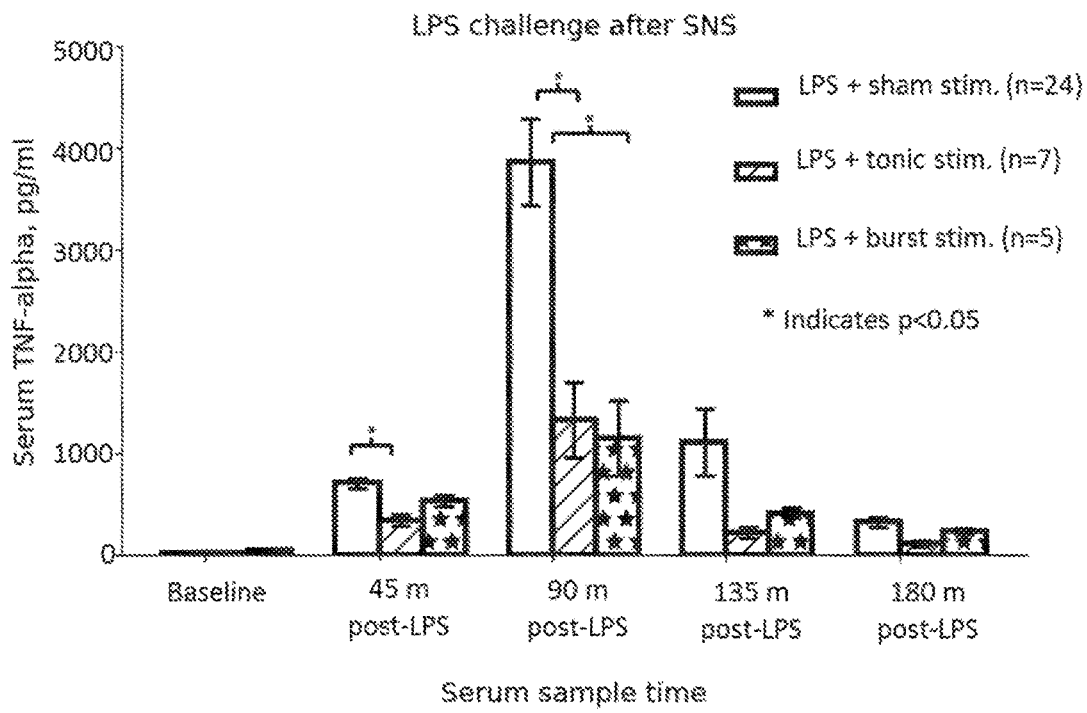
FIG. 19A shows serum TNF-α levels as a function of time starting after completion of 20 minutes of splenic nerve stimulation followed by 10 minutes rest and LPS infusion using either (I) regularly spaced cathodal-first, biphasic pulses (5 Hz) of 1.8 mA (n=7); (2) a train of 10 cathodal-first, biphasic pulses (20 Hz) for 500 ms, followed by a 1.5 second dwell time (n=5); or (3) unstimulated (n=24). The train of pulses followed by a dwell time was as effective as the regularly spaced pulses in modulating serum TNF-α level in the subject.

The splenic neurovascular bundle was exposed and cuff electrodes were implanted for a cohort of rats as described in Example 1. The splenic nerve was stimulated with a 1.8 mA "burst" pulse train (ten cathodal-first, biphasic 300 μs pulses (split evenly between cathodal and anodal phases, with a 60 μs inter-phase interval) at 20 Hz for 500 ms, followed by a 1.5 second dwell time; n=5) or a 1.8 mA "tonic" pulse train (continuous cathodal-first, biphasic 300 μs pulses (split evenly between cathodal and anodal phases, with a 60 μs inter-phase interval) at 5 Hz; n=7) for 20 minutes, before a 10 minute rest followed by infusing the rats with 60 μg/kg LPS in a 500 μl bolus of saline through the venous catheter. A control cohort (n=24) was implanted with the electrodes and infused with LPS, but did not receive any stimulatory pulses. Serum TNF-α levels were measured as described in Example 1 at time points of baseline, 45 minutes, 90 minutes, and 180 minutes following LPS infusion. Serum TNF-α levels as a function of time after LPS infusion and completion of stimulation is shown in FIG. 19A. It was found that the burst pattern was equally effective for reducing TNF-α release compared to a tonic pattern, and thus may be an optimal method when delivering stimulation using a wirelessly-charged implanted device so that the device can charge during the dwell time.

Figure 19B:
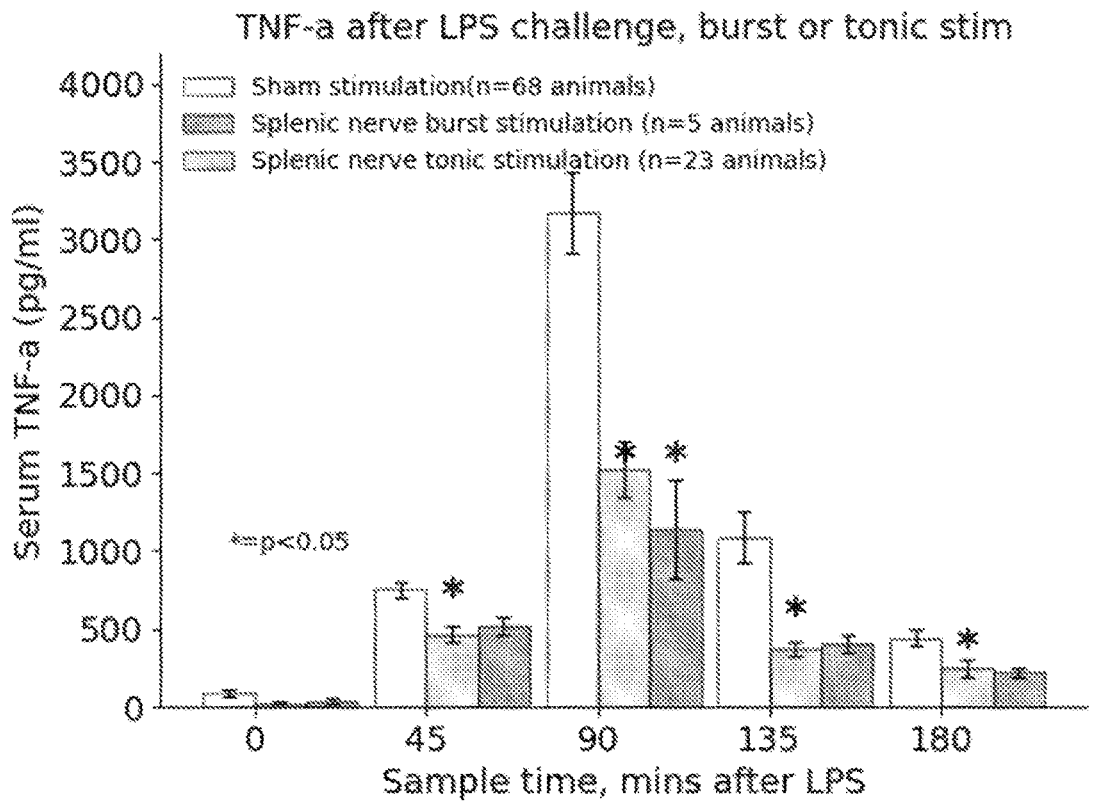
FIGS. 19B-19D show serum TNF-α (FIG. 19B), IL-1β (FIG. 19C), and IL-6 (FIG. 19D) levels in rats at different points in time starting after completion of 20 minutes of splenic nerve stimulation followed by 10 minutes rest and LPS infusion (60 µg/ml I.V.) using either (1) regularly spaced, cathodal-first, biphasic, square wave pulses 300 µs in duration (split evenly between cathodal and anodal phases, with a 60 µs inter-phase interval) with a 1.8 mA pulse amplitude at a rate of 5 per second (5 Hz, n=23); (2) identical pulses organized into a train of 10 pulses at a rate of 20 per second (20 Hz) for 500 ms, followed by a 1.5 second dwell time ("burst stimulation." n=5); or (3) unstimulated (n=68). The train of pulses followed by a dwell time was as effective as the regularly spaced pulses in modulating serum TNF-α level in the subject, but increased levels of pro-inflammatory cytokines IL-10 (FIG. 19B) and IL-6 (FIG. 19C), demonstrating how pulse pattern can differentially influence various cytokines. Asterisks indicate P<0.05 relative to sham.
Figure 19C:
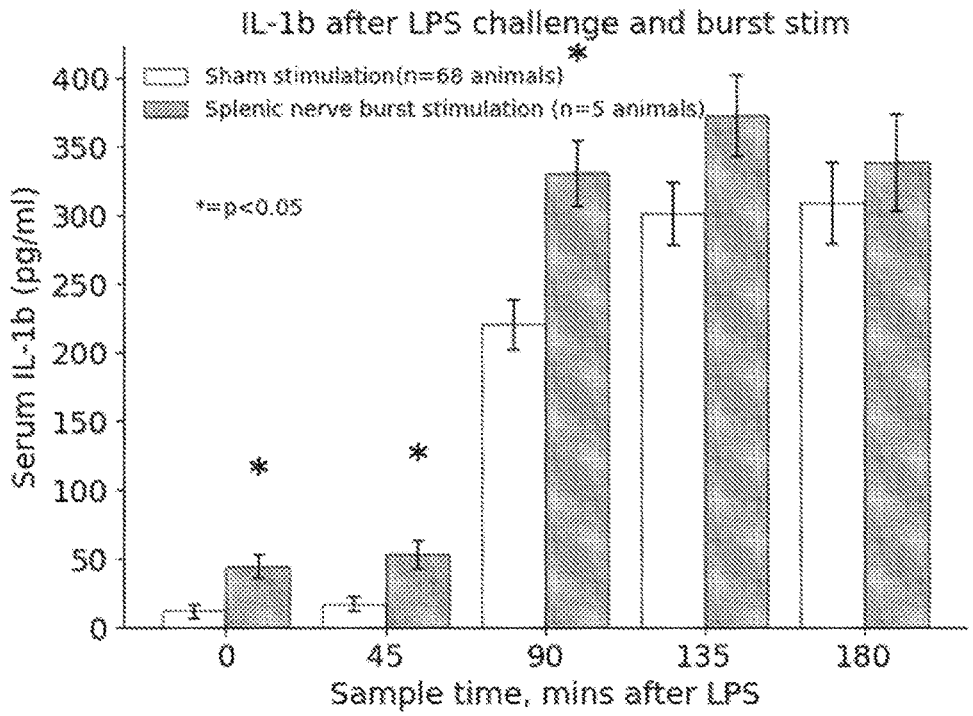
Figure 19D:
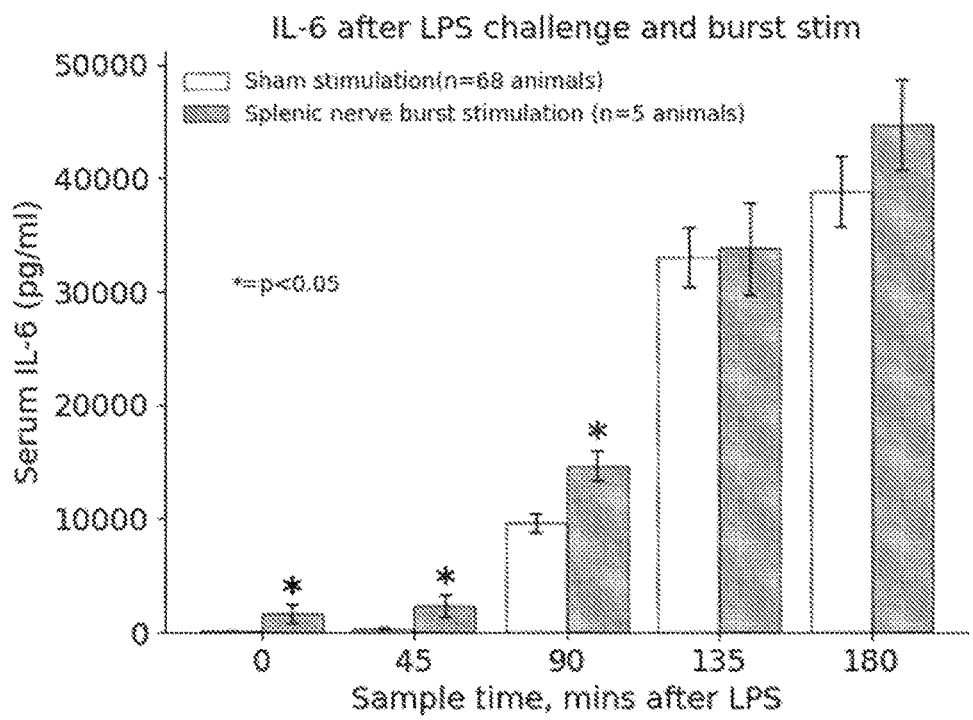

Data for an additional 16 animals was collected by continuously stimulating (tonic stimulation) for 20 minutes using a train of 1.8 mA cathodal-first, biphasic, square wave pulses at a rate of 5 per second (5 Hz), using a 300 μs pulse length (split evenly between cathodal and anodal phases, with a 60 μs inter-phase interval) (total n=23). Data for additional control animals was also collected (total n=68). Serum TNF-α levels were measured at time points of baseline, 45 minutes, 90 minutes, and 180 minutes following LPS infusion. Serum TNF-α levels as a function of time after LPS infusion and completion of stimulation is shown in FIG. 19B. This further confirmed that the burst pattern was equally effective for reducing TNF-α release compared to a tonic pattern. The effects of burst stimulation on pro-inflammatory cytokines IL-1β (FIG. 19C) and IL-6 (FIG. 19D) release were also examined using the same serum samples used to test TNF-α. Unlike TNF-α, levels of IL-1β and IL-6 were significantly increased over sham levels at the early timepoints. This effect differs from what was observed using tonic stimulation pulses (see FIG. 14B). These data demonstrate that stimulation patterns can be used to differentially effect various cytokines simultaneously.

Figure 20:
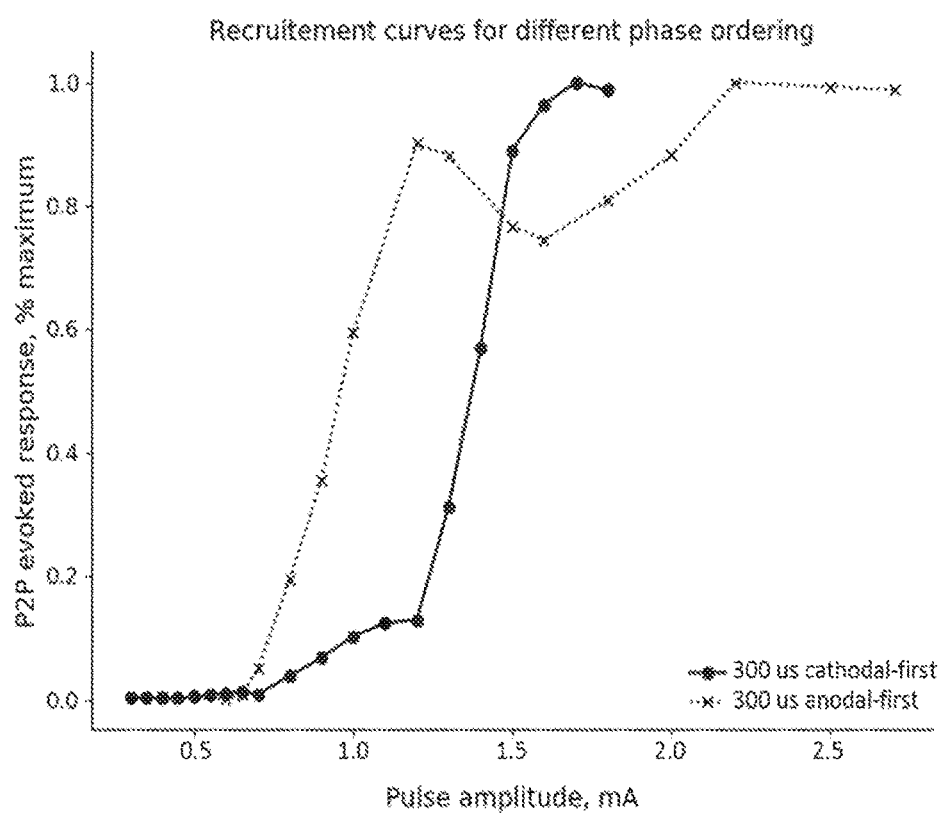
FIG. 20 shows peak-to-peak (P2) evoked response at various pulse amplitudes for biphasic, anodal-first 300 µs pulses or biphasic, cathodal-first 300 µs pulses (split evenly between cathodal and anodal phases, with a 60 µs inter-phase interval).

Example 7: Splenic Nerve Stimulation Pulse Polarity for Modulation of Splenic Nerve Activity In this example, the ordering of the biphasic pulses were varied in order to demonstrate the ability of anodal-first pulses to trigger splenic nerve responses at lower pulse amplitudes, thus improving energy efficiency. In a cohort of rats, the splenic neurovascular bundle was exposed and a pair of cuff electrodes was implanted on the nerve/artery complex as described in Example 2. Recruitment curves were generated for anodal- or cathodal-first, biphasic, square wave pulses of 300 μs in length (split evenly between cathodal and anodal phases, with a 60 μs inter-phase interval) of varying amplitudes ranging from 100 μA to 2.6 mA by delivering the stimulation to the proximal electrode and recording the CAP at the distal electrode. Data from a representative animal is shown in FIG. 20. Each point is the average of 100 evoked responses. The threshold for eliciting a CAP was lower for anodal-first pulses in the threshold and mid-range response zones, demonstrating that anodal-first pulses can trigger CAP responses with less current than cathodal-first pulses.

Example 8: Measurement of Anti-Tumor Cytotoxicity of Immune Cells

In this example, cytotoxic activity of immune cells (including, natural killer (NK) and/or cytotoxic T-cells) is measured using cells isolated from peripheral blood and/or from the spleen. In a cohort of rats, mice or other laboratory animals, the splenic neurovascular bundle is exposed and a pair of cuff electrodes are implanted on the nerve/artery complex as described in Example 2. The splenic nerve is electrically stimulated (or not for control animals) to increase activation of cytotoxic T-cells and NK cells or decrease activation of cytotoxic T-cells and NK cells. A peripheral blood sample is drawn from the animals before stimulation, after stimulation, and before the animals are sacrificed and/or the spleen removed.

In peripheral blood, white blood cells are isolated using density gradient centrifugation. White blood cells from the spleen are isolated by homogenizing the spleen and lysing the RBCs using a lysis buffer such as ammonium-chloride-potassium buffer, before isolating the white blood cells by density gradient centrifugation. The white blood cell fraction is depleted of B-cells using a 1-hour incubation in a nylon wool column. The resulting flow-through suspension contains T-cells and NK cells, and is used for the remaining steps of the assay. Optionally, the NK cells and T-cells can be individually purified from this suspension using a magnetic cell sorting procedure. During this step, a negative selection in which the unwanted cells are labeled with antibodies covalently bound to magnetic beads can be used. The cell suspension is then passed through a magnetic column which binds the unwanted cells, allowing the cells of interest (i.e., T-cells and/or NK cells) to flow freely and be collected.

Cultured YAC-1 lymphoma cells are prepared by passaging them the day prior to the assay to ensure they are in the exponential growth phase on the day of the assay. YAC-1 cells ("target" cells) and the isolated immune cells ("effector" cells) are co-incubated for 4 hours at different effector: target ratios: 10:1, 20:1, 40:1, and 100:1. After the incubation, cytotoxicity is measured using commercially-available cytotoxicity assay kits (for example, $^{51}$Cr release kits or LDH release kits) following manufacturer instructions. The amount of target cell lysis can then be compared between control and stimulation conditions.

Example 9: Measurement of Circulating Peripheral Immune Cell Levels

In a cohort of mice, the splenic neurovascular bundle is exposed and a pair of cuff electrodes are implanted on the nerve/artery complex as described in Example 2. The splenic nerve is electrically stimulated (or not for control animals) to increase circulation of T cells, cytotoxic T-cells, and NK cells or decrease circulation of T-cells, cytotoxic T-cells and NK cells. Fresh whole blood is collected from the animals prior to and up to 20 minutes after nerve stimulation.

Levels of circulating NK, T-cells, and cytotoxic T-cells are compared in the before-stimulation and after-stimulation samples to determine the magnitude of the effect of stimulation. At least 100 µL of whole blood per sample is collected into anti-coagulant tubes. Fluorescent antibodies against NK cells (CD335), T-cells (CD3) and cytotoxic T-cells (CD8a) are added to the whole blood samples and incubated for 20-30 minutes at room temperature. After incubation, red blood cell lysis is accomplished using a RBC lysis buffer such as ammonium-chloride-potassium buffer for 5-10 minutes, 10 mL of PBS is then added to stop the reaction, and the cells are pelleted by centrifugation and resuspended in 2 mL of FCS buffer. A hemocytometer is used to determine the cell density of the suspension. Cells are again pelleted by centrifugation, and then resuspended in FCS buffer at a concentration of $1 \times 10^7$ cells/mi. Finally, 7AAD is added to label apoptotic cells. This suspension is then run through a flow cytometer to determine the percentages of each labeled cell type in the total cell population.

Example 10: Multiplex Cytokine/Chemokine Measurement

In a cohort of mice, the splenic neurovascular bundle is exposed and a pair of cuff electrodes are implanted on the nerve/artery complex as described in Example 2. Serum is collected from animals before and after nerve stimulation and used in a commercially available multiplex assay to determine cytokine/chemokine levels (for example, the Bio-Plex Pro™ Rat Cytokine 23-plex Assay (Bio-Rad), read by the Bio-Plex® 200 Luminex Suspension Array Analyzer, which is used to determine levels of IL-12 (p70), IL-13, IL-17A, IL-18, M-CSF, MCP-1, MIP-1α, MIP-3α, RANTES, TNF-α, VEGF, G-CSF, GM-CSF, GRO/KC, IFN-γ, IL-1α, IL-1β, IL-2, IL-4, IL-5, IL-6, IL-7, and IL-10). The relative levels are compared in the pre- and post-stimulation conditions. Cytokines and chemokines of particular interest for oncological treatments include: IL-2, an activator of natural killer cells with anti-cancer activity; VEGF, a stimulator of vasculature growth in tumors; IFN-γ, which is secreted by activated NK cells; TNF-α, IL-6, and IL-1β which are each known to be pro-inflammatory cytokines that have relevance in cancers that are sensitive to a pro-inflammatory phenotype; G-CSF, which can stimulate the recovery of white blood cells after chemotherapy treatment; and IL-10, an anti-inflammatory cytokine that has relevance for cancers sensitive to a pro-inflammatory phenotype.

Example 11: In Vivo Tumor Monitoring

Two cohorts of mice will be used for the following procedures. The splenic neurovascular bundle is exposed and a pair of cuff electrodes are implanted on the nerve/artery complex as described in Example 2. The electrodes are connected to an implantable pulse generator which is placed in the abdominal cavity of the mouse. Then, the wound is closed with suture and the animals are given time to recover. After a recovery period, cancer cells (such as YAC-1 or MC38 cells) are subcutaneously injected near the animal's flank, and allowed to grow for a fixed period of time. At a predetermined interval following tumor cell implantation, one cohort of mice is subjected to daily splenic nerve stimulation by activating the implantable pulse generator. The pulse generator is pre-programmed to deliver stimulation designed to increase NK cell and cytotoxic T-cell activity. The second cohort (control) is handled in a similar manner to the first cohort, but the pulse generator is remains inactive. This protocol continues for a fixed period of days in both cohorts. Additionally, animals will undergo blood sampling during this period, and serum samples will be tested to measure cytokine concentrations. At the end of this period, animals are sacrificed and the implanted tumors are excised. Tumors are measured and weighed to determine their size and mass. The size of the tumors removed from the stimulation cohort is compared to those removed from the control cohort to assess differences in tumor growth.

Example 12: Measurement of Circulating Peripheral Immune Cell Levels after Splenic Nerve Stimulation The splenic neurovascular bundle was exposed and cuff electrodes were implanted for a cohort of rats as described in Example 1. The splenic nerve was stimulated with a 3 mA "burst" pulse train consisting of cathodal-first biphasic, square wave pulses, 300 µs in duration (split evenly between cathodal and anodal phases, with a 60 µs inter-phase interval) at 30 Hz for 30 seconds, followed by a 30 second dwell time, continuing for 20 minutes (n=14); or a 3 mA "tonic" pulse train consisting of identical pulses, but repeated at a continuous rate of 5 per second (Tonic 5 Hz; n=35) for 20 minutes. No LPS or other substances were infused. A control cohort (n=38) was implanted with the electrodes and infused with LPS, but did not receive any stimulatory pulses. Fresh whole blood was collected from the animals in several time bins prior to and up to 120 minutes after nerve stimulation.

Levels of circulating natural killer (NK) cells and cytotoxic T-cells were compared in the samples taken before stimulation and after samples to determine the magnitude of the effect of stimulation. At least 100 µL of whole blood per sample was collected into anti-coagulant tubes. Fluorescent antibodies against NK cells (CD335), T-cells (CD3) and cytotoxic T-cells (CD8a) were added to the whole blood samples and incubated for 20-30 minutes at room temperature. After incubation, red blood cell lysis was accomplished using an RBC lysis buffer such as ammonium-chloride-potassium buffer for 10-20 minutes, 10 mL of PBS was then added to stop the reaction, and the cells were pelleted by centrifugation and resuspended in 2 mL of FCS buffer. A hemocytometer was used to determine the cell density of the suspension. Cells were again pelleted by centrifugation, and then resuspended in FCS buffer at a concentration of $1 \times 10^7$ cells/ml. Finally, a dye was added to label apoptotic cells. This suspension was then run through a flow cytometer to determine the percentages of each labeled cell type in the total cell population.

Figure 21A:
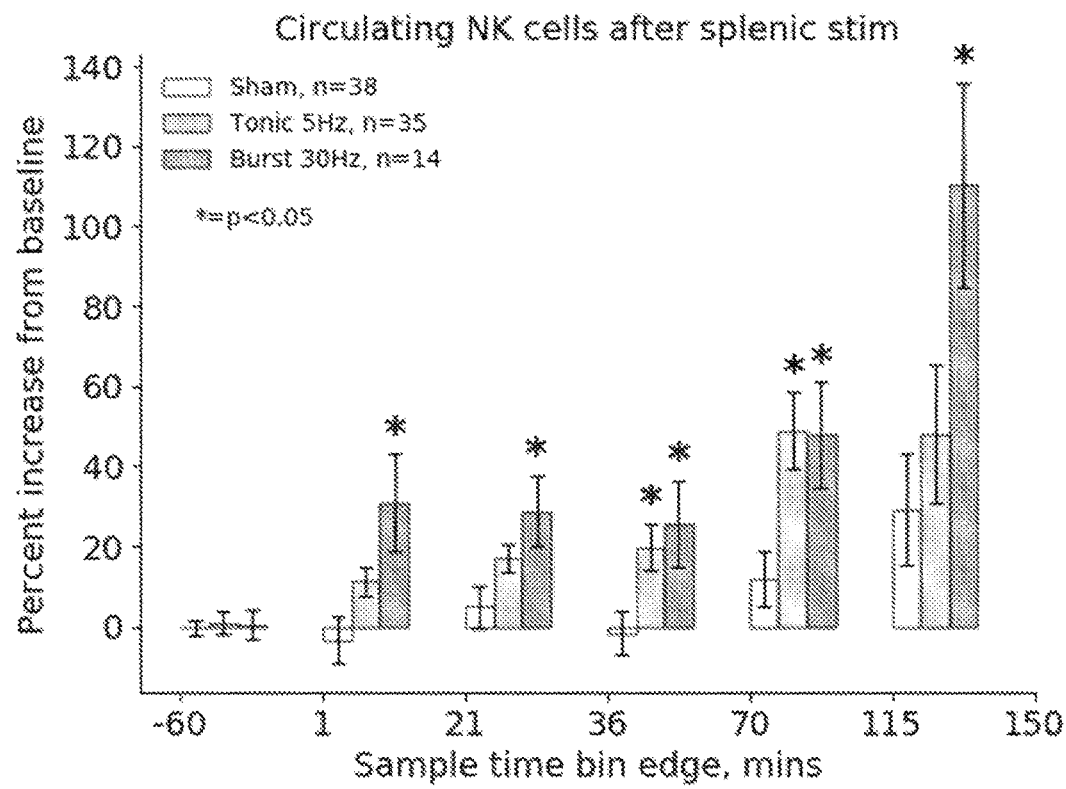
FIG. 21A shows relative change of rat peripheral blood natural killer (NK) cells in as a percent of total lymphocytes, sampled across several time bins.
Figure 21B:
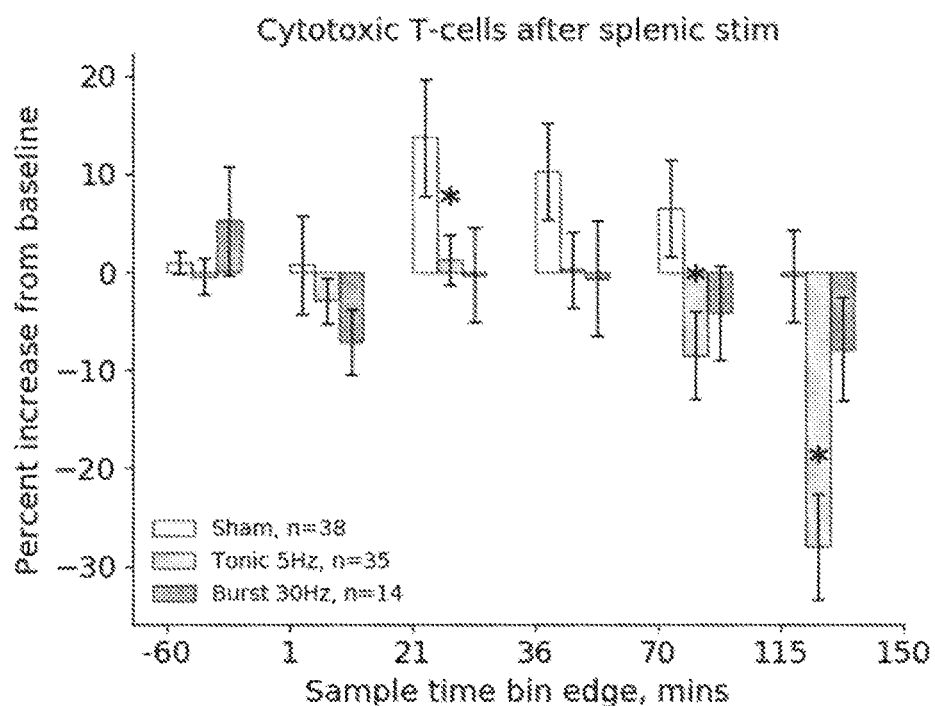
FIG. 21B shows relative change rat peripheral blood cytotoxic T cells in as a percent of total lymphocytes, sampled across several time bins. Times are relative to stimulation onset. Rats were grouped into three different conditions: (1) No stimulation (Sham, n=38); (2) 20 minutes of splenic nerve stimulation with regularly spaced pulses (Tonic 5 Hz, n=35); and (3) a train of 10 pulses at a rate of 30 per second (30 Hz) for 30 s, followed by a 30 second dwell time, continuing for 20 minutes (Burst 30 Hz, n=14). Pulses used in both stimulation conditions were cathodal-first, biphasic, square wave pulses 300 µs in duration (split evenly between cathodal and anodal phases, with a 60 µs inter-phase interval) and a 3 mA pulse amplitude. Asterisks show values for each condition that are significantly different than sham. The burst pattern was more effective in stimulating cytosis of natural killer cells.

Tonic 5 Hz stimulation increased the levels of peripheral NK cells (measured as a percent of lymphocytes) relative to pre-stimulation timepoints. These effects were significant over sham animals at the 50-minute and 80-minute timepoints, as shown in FIG. 21A. Animals treated with burst stimulation demonstrated a stronger release of NK cells, which was significant over sham levels at the 15, 35, 50, 80, and 120-minute time points. Additionally, tonic stimulation decreased the levels of cytotoxic T cells at the 35, 80, and 120 minute timepoints relative to sham stimulation (FIG. 21B). This effect was not observed for animals who were treated with burst stimulation. These data demonstrate the splenic nerve stimulation can induce cytosis of natural killer cells and inhibit the cytosis of cytotoxic T cells, and that patterned stimulation can modulate these effects compared to tonic stimulation.

Example 13: Effect of Splenic Nerve Stimulation on Tumor Growth in Mice

Three cohorts of mice were used for this example. For two cohorts (Stim and Sham), the splenic neurovascular bundle was exposed using aseptic technique and a pair of wire electrodes were implanted into the abdominal cavity—one on the nerve/artery complex as described in Example 1, and the second was placed nearby but not anchored to a particular structure. The electrodes were connected to an implanted dorsal pedestal which externalized a connector for the electrodes. Then, the wound was closed with suture and the animals was given time to recover. After a recovery period of 2-4 days, CT26 colon cancer cells were subcutaneously injected near the animal's flank. At this time, a third naïve cohort (Control) was also injected with tumor cells. Beginning 1 day following tumor cell implantation, the first cohort of mice (Stim, n=11) was subjected to daily splenic nerve stimulation by connecting the electrodes to a pulse generator. The pulse generator was programmed to deliver a 1.8 mA "tonic" pulse train (continuous cathodal-first, biphasic 300 µs pulses (split evenly between cathodal and anodal phases, with a 60 µs inter-phase interval)) at 5 Hz for 20 minutes. The second cohort with implants (Sham, n=14) was handled in a similar manner to the first cohort, but the pulse generator was never active. The final cohort (Control, n=34) was not handled. This protocol continued for 16 days in all cohorts, during which time tumor size was measured in two axes using digital calipers to determine the tumor volume. While there was no significant difference in tumor growth between Sham and Control groups, tumors in the Stim group grew more slowly. In aggregate, this effect was significant on individual days 13, 14, and 15 (FIG. 22A, * indicates p-value<0.05) Exponential growth curves were computed using data across all days for the three cohorts (FIG. 22B). Using 95% confidence intervals from these exponential fits (FIG. 22C), no significant difference between the Sham and Control groups was observed, but there was a significant effect for the Stim group that indicated slower tumor growth. These data demonstrate that daily splenic nerve stimulation can reduce the growth rate of solid tumors in mice.

Example 14: Effect of Splenic Nerve Stimulation on Cytokine Production and Circulating NK Cell Levels in Humans One cohort of 10 human patients was studied in the following example. All patients were undergoing laparotomy as part of a tumor resection procedure. Splenic nerve stimulation was performed after laparotomy, but prior to tumor resection. To assay cytokine levels, blood samples were drawn at the following time points: after laparotomy, but prior to stimulation; immediately after stimulation (t=0), as well as 60 and 120 minutes after stimulation (t=60 and t=120). To place stimulating electrodes after accessing the abdominal cavity, a surgical team isolated a ~2 cm segment of the proximal splenic neurovascular bundle (splenic artery and associated nerves) nearby to the branch point from the celiac artery. Individual nerves were not further isolated due to their small size and to avoid the risk of nerve damage. Two custom-designed, 4-pole nerve cuffs with a floating counter electrode (Cortec Neuro GMBH) were placed serially along the isolated splenic artery.

Once the cuffs were in place, a fixed stimulation protocol designed to detect the presence of evoked splenic nerve responses at various amplitudes was initiated. At the proximal cuff, biphasic pulses with a duration of 150 µs per phase, and a 100 µs interphase interval at a 5 Hz frequency were delivered. During the first phase of stimulation, pulses were delivered in 8 sets (pulse trains) of 30 pulses with a 24 second period from the start of one set to the start of the next. Within each set of 30 pulses, pulse amplitude was fixed and increased monotonically between sets, beginning with 30 pulses at 1 mA for the first set, then 30 pulses at 2 mA for the next set and so forth, before ending with 30 pulses at 8 mA in the last set. During this time, the distal cuff was connected to an amplifier that recorded an amplified voltage signal. After a 5 minute quiescent period, the splenic nerves were again stimulated continuously for 15 minutes at 5 Hz (cathodal-first, biphasic pulses with a duration of 150 µs per phase, and a 100 µs interphase interval) using a single pulse amplitude of 6 (n=4) or 8 mA (n=6).

Figure 23A:
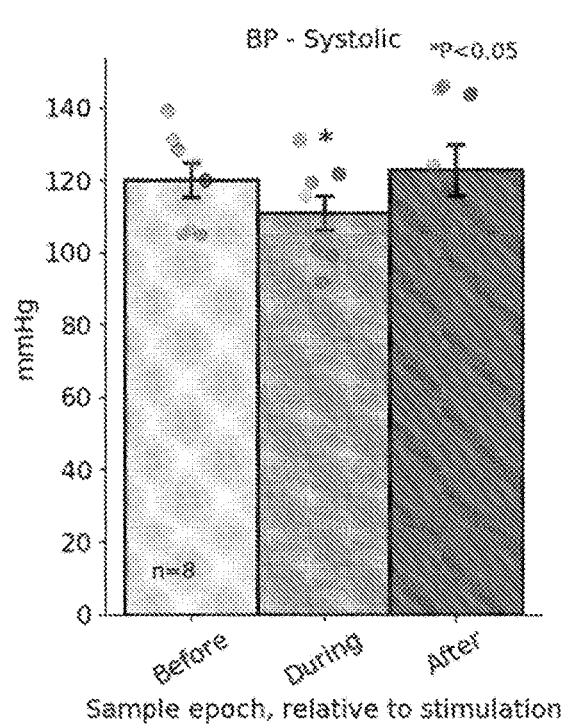
FIGS. 23A-23E show the effects of splenic nerve stimulation on vital signs, including systolic blood pressure (FIG. 23A), diastolic blood pressure (FIG. 23B), mean blood pressure (FIG. 23C), heart rate (FIG. 23D), and pulse oxygenation (FIG. 23E). The splenic nerve was stimulated with a 15 minute continuous train of cathodal-first, biphasic, square wave pulses with a duration of 300 µs (split evenly between cathodal and anodal phases, with a 100 µs inter-phase interval) at a frequency of 5 pulses per second (5 Hz) and at an amplitude of 6 mA (n=4) or 8 mA (n=6). The average values for each parameter were computed across a 15-minute window before, during, and after splenic nerve stimulation. Asterisks show significant differences (P<0.05) relative to the before-stimulation epoch. Splenic nerve stimulation induced mild changes in systolic and mean blood pressure as well as heart rate.
Figure 23B:
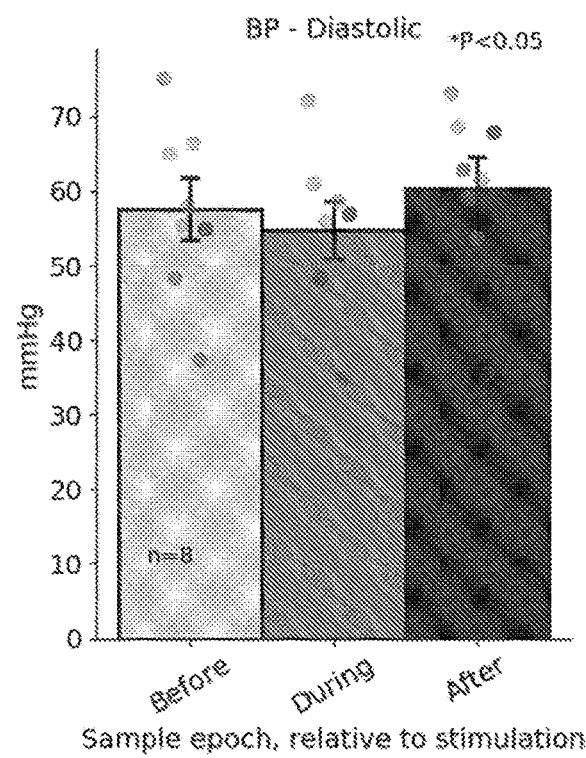
Figure 23C:
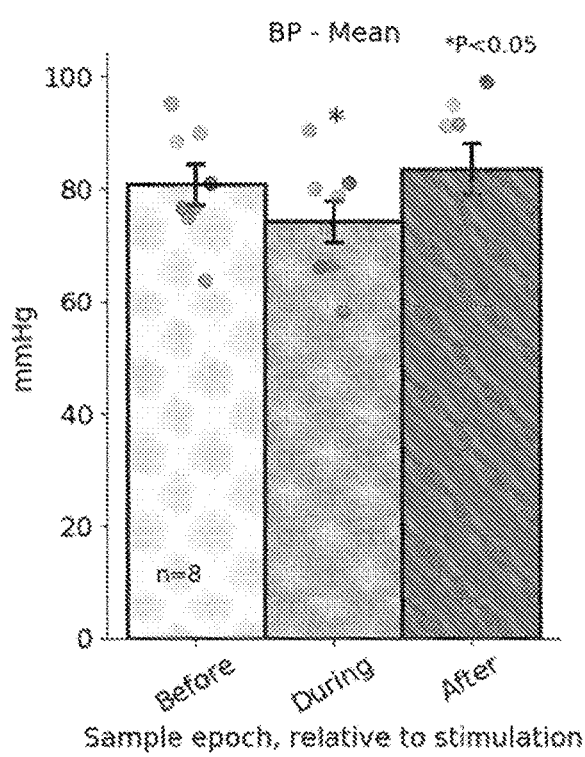
Figure 23D:
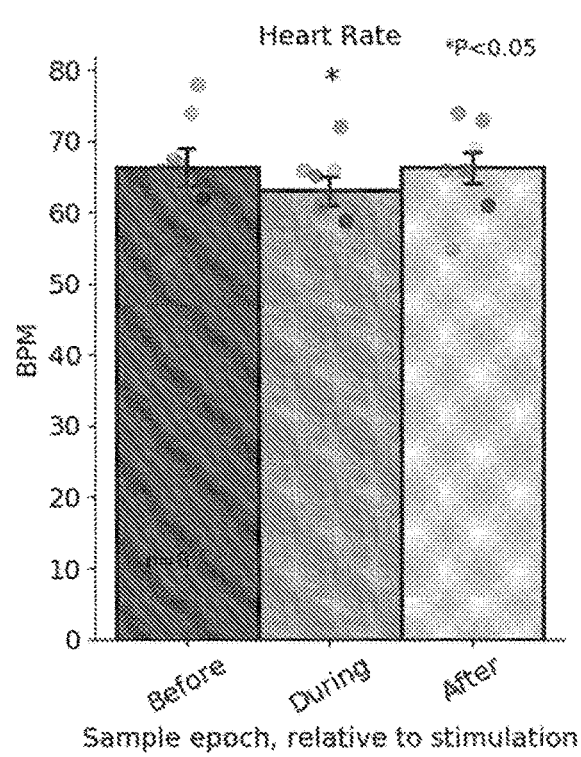
Figure 23E:
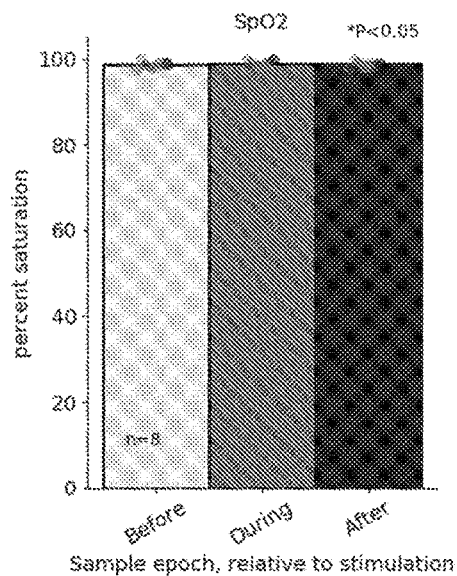

Vital signs, including systolic blood pressure, diastolic blood pressure, mean blood pressure, heart rate, and pulse oxygenation were continuously monitored in 8 of the 10 subjects before, during and after splenic nerve stimulation. To determine the effects of stimulation on these parameters, the mean value of each parameter was computed over a 15-minute period prior to stimulation, a 15 minute period during continuous tonic stimulation at 5 Hz, and a 15 minute period after stimulation. Systolic blood pressure (FIG. 23A), mean blood pressure (FIG. 23B), and heart rate (FIG. 23C) underwent small but statistically significant decreases during splenic nerve stimulation, while diastolic blood pressure (FIG. 23D) and pulse oxygenation (FIG. 23E) did not change significantly. These effects were mild, suggesting that splenic nerve stimulation does not cause dangerous cardiovascular effects in humans.

Whole blood samples were drawn before and 0 minutes, 60 minutes, and 120 minutes following the conclusion of splenic nerve stimulation, and the blood samples were split into multiple fractions for different analyses.

Figure 24A:
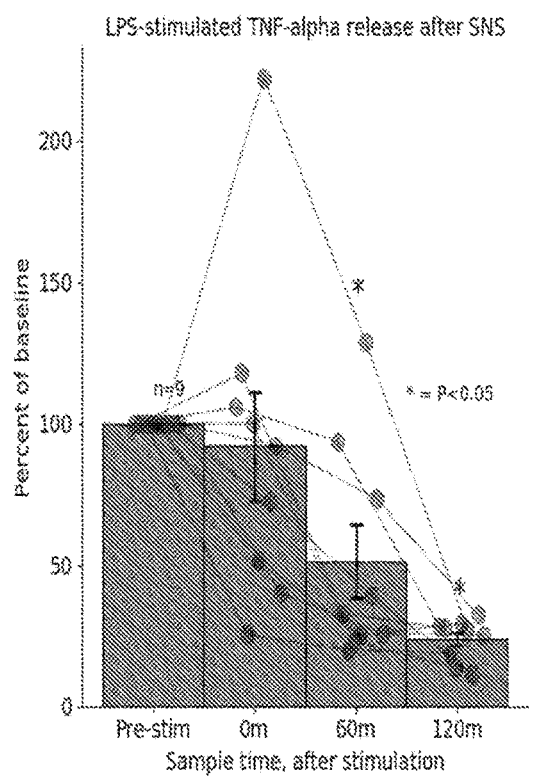
FIGS. 24A-24D Results of human (n=9) splenic nerve stimulation on whole blood pro-inflammatory cytokine production (TNF-α, FIG. 24A; IL-1β, FIG. 24B; and IL-6 FIG. 24C) and anti-inflammatory cytokine production (IL-10, FIG. 24D) after samples were incubated with 1 µg/mL lipopolysaccharide (LPS) to trigger an immune reaction. Cytokine levels for each patient were normalized to the concentration measured at the pre-stimulation time point, allowing for a within-subject comparison. The splenic nerve was stimulated with a continuous train of cathodal-first, biphasic, square wave pulses with a duration of 300 µs (split evenly between cathodal and anodal phases, with a 100 µs inter-phase interval) at a frequency of 5 pulses per second (5 Hz) and at an amplitude of 6 mA (n=4) or 8 mA (n=6) for 15 minutes Asterisks signify statistically significant (P<0.05) group differences relative to the pre-stimulation time point. Splenic nerve stimulation was effective at inducing an anti-inflammatory profile in human blood.
Figure 24B:
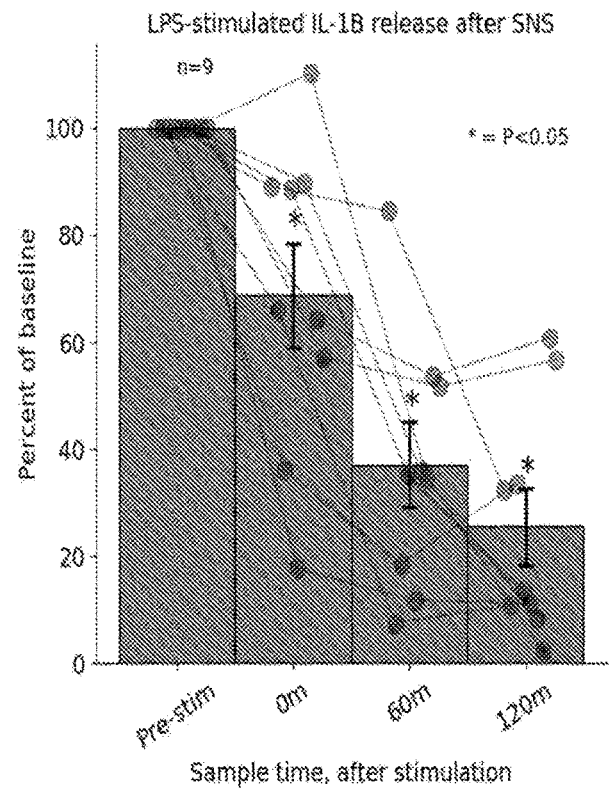
Figure 24C:
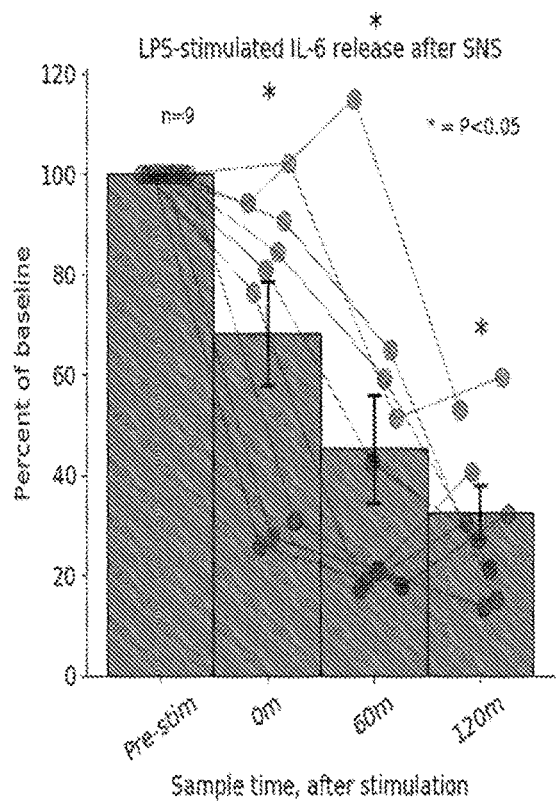
Figure 24D:
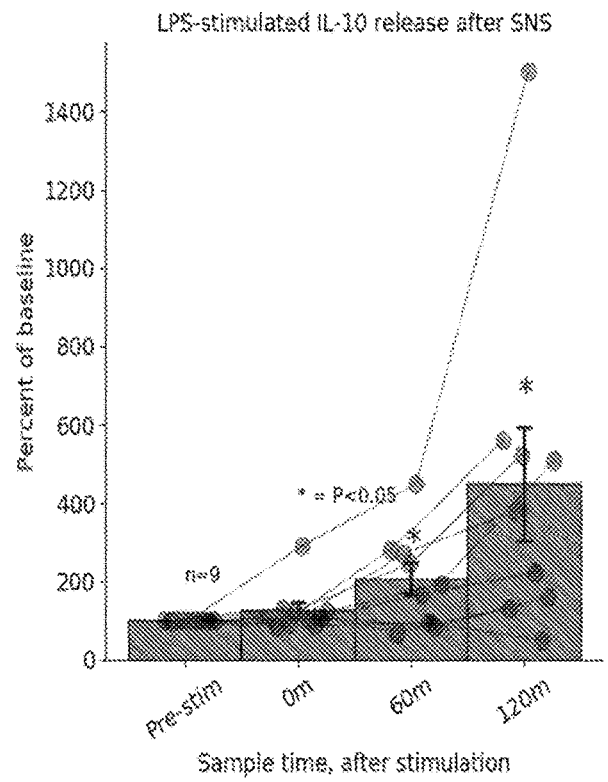

Cytokine analysis. For 9/10 patients, one fraction was incubated with 1.0 µg/mL LPS for 4 hours, while another fraction was incubated with 5.0 µg/mL LPS for 4 hours. For one patient, the blood was incubated with only 0.01 µg/ml LPS for 4 hours. Plasma was isolated from each blood sample and cytokine levels were measured using a sandwich ELISA assay. Levels of pro-inflammatory cytokines (TNF-α, IL-6, IL-1β) were determined, along with levels of one anti-inflammatory cytokine (IL-10). This study design allowed for a within-subject analysis by comparing cytokines produced by blood samples prior to stimulation to blood samples drawn after stimulation. For blood samples incubated with 1 µg/mL LPS, all pro-inflammatory cytokine (TNF-α, IL-6, IL-1β) levels decreased after stimulation (FIG. 24A, FIG. 24B, and FIG. 24C), while IL-10 levels increased (FIG. 24D). These effects were strongest at the 120 min post-stimulation time point, and significant for each of the measured cytokines. These data suggest that splenic nerve stimulation induces an anti-inflammatory state in human circulating immune cells. The cytokine response of whole blood to 5 µg/ml LPS was larger in magnitude than the response to 1 µg/mL, but the relative effects between samples were not meaningfully different. Only minimal change in cytokine levels were detected for the sample incubated with 0.01 µg/ml LPS.

Natural Killer Cell Analysis. First, peripheral blood mononuclear cells (PBMCs) were isolated using density gradient centrifugation in Ficoll-Paque Plus. PBMCs were then washed in PBS, and then frozen at −80° C. in fetal bovine serum, with the addition of 10% DMSO. On the day of analysis, cells were thawed in a 37° C. water bath, and PBMCs were again washed in PBS and resuspended in cRPMI (RPMI 1640+10% FBS+1% Pen/Strep+1% NEAA+ 1% NaPyruvate) and 2 IU/mL DNase. After a 1 hour incubation, cells were again washed and resuspended in cRPMI. To prime the cells, PBMCs were plated at $10^6$ cells/well in 48-well plates at a volume of 1 mL/well, along with 5 ng/mL IL-15, and incubated overnight at 37° C.

The characteristics of NK cells sampled at different pre- and post-stimulation timepoints were tested by combining the primed PBMCs with a target cell line (721.221—an EBV-transfected B-cell line) at a ratio of 1:1. Antibodies against the cell-surface marker CD107a were added and incubated for 1 hour with the cells, prior to adding protein transport inhibitors monensin and brefeldin A for an additional 6-hour incubation. Cells were then stained with a viability dye and antibodies against extracellular markers CD3, CD14, CD19 and CD56. Finally, a permeabilization step was completed, followed by staining for intracellular markers TNF-alpha, MIP-1β, and IFN-γ.

Figure 25A:
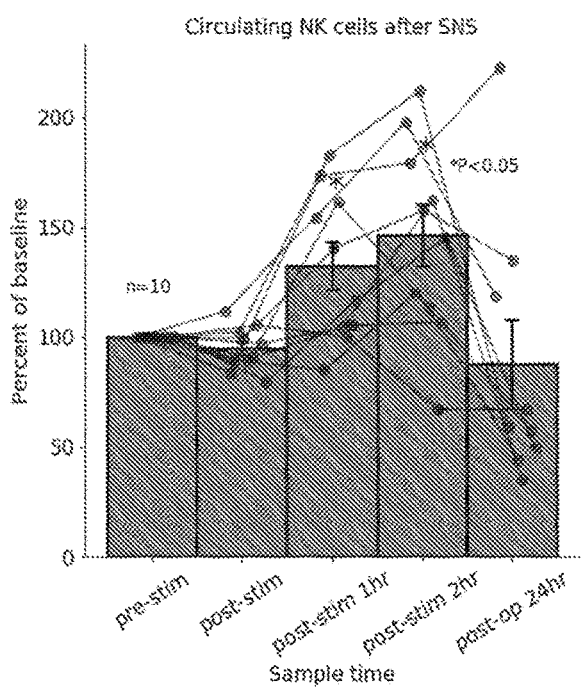
FIGS. 25A-25E show the effect of human (n=10) splenic nerve stimulation (SNS) on peripheral blood natural killer (NK) cells. The splenic nerve was stimulated with a continuous trains of 30 cathodal-first, biphasic, square wave pulses with a duration of 300 µs (split evenly between cathodal and anodal phases, with a 100 pts inter-phase interval) at a frequency of 5 pulses per second (5 Hz) and at an amplitude of 6 mA (n=4) or 8 mA (n=6) for 15 minutes.
Figure 25B:
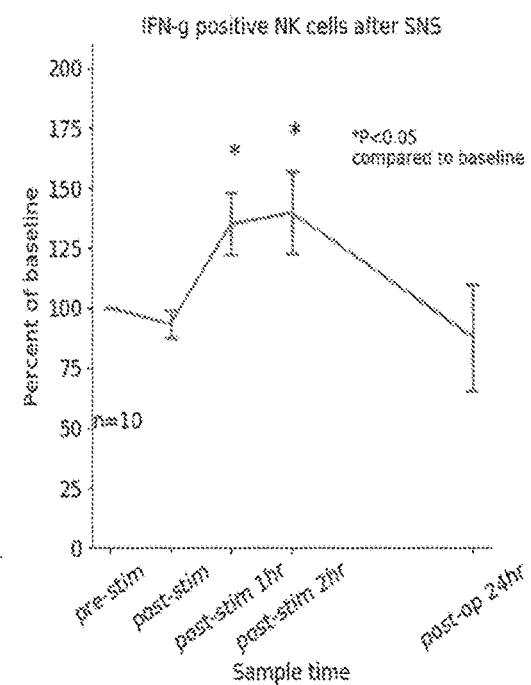
Figure 25C:
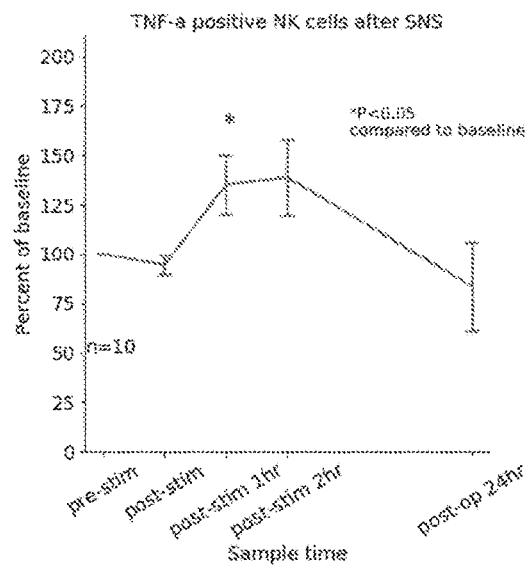
Figure 25D:
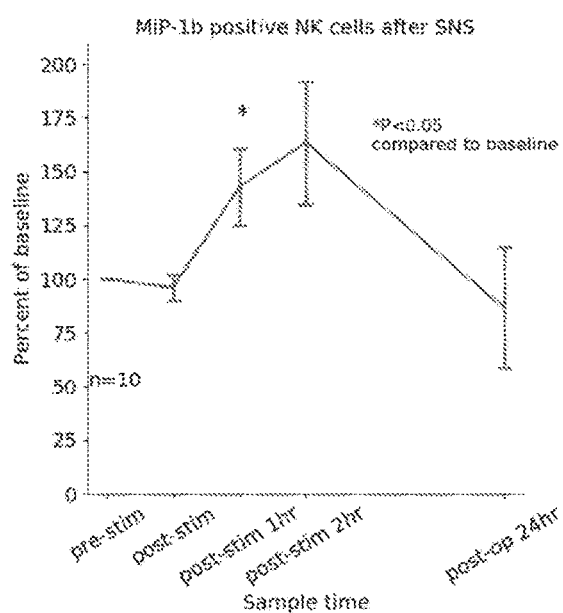
Figure 25E:
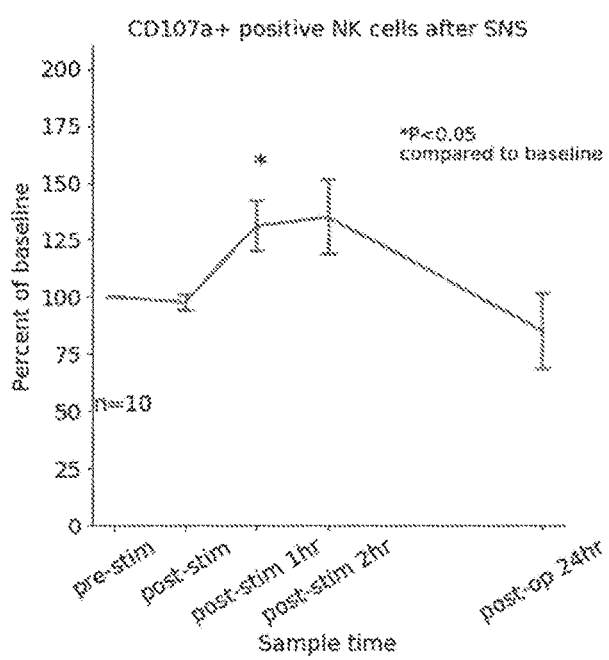

The number of NK cells measured in peripheral blood (as a percentage of total lymphocytes using flow cytometry) increased for all patients relative to the pre-stimulation time point (FIG. 25A). This effect was significant at the 1-hour and 2-hour post-stimulation time points, demonstrating that splenic nerve stimulation induces an increase in circulating natural killer cells in human patients with cancer. In addition, the number of NK cells expressing activation markers IFN-γ (FIG. 25B), TNF-α (FIG. 25C), MIP-1β (FIG. 25D), and CD107a (FIG. 25E) was determined by multiplying the proportion of peripheral NK cells by the proportion of those cells expressing the marker of interest. For all activation markers tested, there was increase in the number of activated NK cells in the peripheral samples following splenic nerve stimulation, with at least one post-stimulation timepoint displaying a significant effect relative to pre-stimulation samples. These data demonstrate that splenic nerve stimulation can increase the number of active NK cells in peripheral blood in human patients with cancer.

Example 15: Splenic Nerve Stimulation Pulse and Amplitude Pattern for Modulation of Cytokine Release In order to test how the splenic nerve stimulatory pulse pattern, including amplitude modulations, affects modulation of serum TNF-α level in subjects after stimulation of the splenic nerve, the splenic nerve was stimulated using a series of electrical pulses in a cohort of rats with a dwell time (i.e., a quiescent period) between pulse trains. Additionally, the amplitude of stimulatory pulses was monotonically increased at the start of each new pulse train, so that each pulse train consisted of a number of pulses at a fixed amplitude, but the subsequent pulse train consisted of pulses at a higher amplitude than the previous train, termed "RC Stimulation". This was compared to a "tonic" stimulation paradigm, which delivered pulses at a steady frequency throughout the stimulation period. The total number of pulses delivered during RC stimulation was less than the total number of pulses delivered during tonic stimulation.

Figure 26:
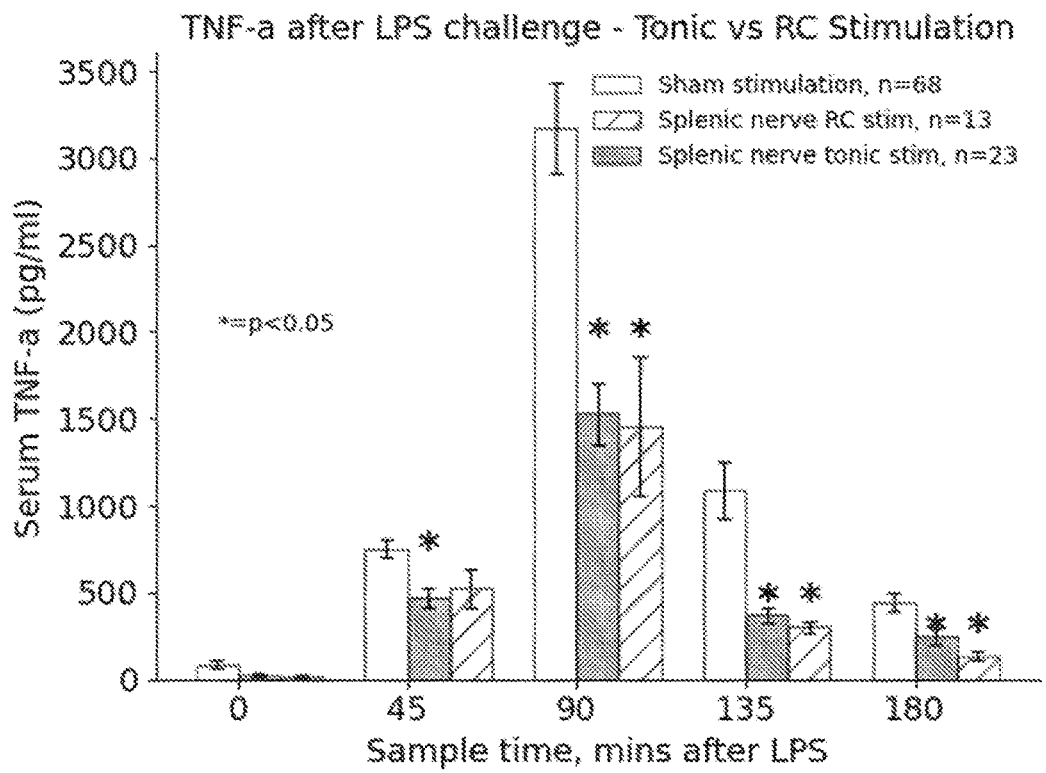
FIG. 26 shows the effect of two types of splenic nerve stimulation, or no stimulation on serum TNF-α levels. In one cohort of rats (Splenic nerve RC stim, n=13), the nerve was stimulated with an "RC" pulse train, which consisted of a total of 8 trains of 30 pulses, with each pulse train separated by a 24 second dwell time. The first pulse train consisted of 30 continuous cathodal-first, biphasic 300 µs pulses (split evenly between cathodal and anodal phases, with a 60 µs inter-phase interval) delivered at 3 Hz. The first pulse train consisted of 30 pulses at 0.52 mA, and the amplitude of all pulses in each successive pulse train increased by 0.129 mA. As such, the final pulse train consisted of 30 pulses at 1.42 mA. In the second cohort (n=23), the nerve was stimulated with a "tonic" pulse train, consisting of continuous cathodal-first, biphasic 300 µs pulses, split evenly between cathodal and anodal phases, with a 60 µs inter-phase interval at 5 Hz for 20 minutes. In the final cohort of rats (Sham stimulation, n=68), the nerve was unstimulated. Asterisks show statistically significant (P<0.05) differences with respect to sham values.

The splenic neurovascular bundle was exposed and cuff electrodes were implanted for a cohort of rats as described in Example 1. The splenic nerve of the first group (n=13) was stimulated with an "RC" pulse train, which consisted of a total of 8 trains of 30 pulses, with each pulse train separated by a 24 second dwell time. The first pulse train consisted of 30 continuous cathodal-first, biphasic 300 μs pulses (split evenly between cathodal and anodal phases, with a 60 μs inter-phase interval) delivered at 3 Hz. The first pulse train consisted of 30 pulses at 0.52 mA, and the amplitude of all pulses in each successive pulse train increased by 0.129 mA. As such, the final pulse train consisted of 30 pulses at 1.42 mA. Alternately, the nerve was stimulated with a 1.8 mA "tonic" pulse train (continuous 300 μs pulses, split evenly between cathodal and anodal phases, with a 60 μs inter-phase interval) at 5 Hz (n=23) for 20 minutes. A control cohort (n=68) was implanted with the electrodes and infused with LPS, but did not receive any stimulatory pulses. For all rats, after a 10 minute rest following stimulation, rats were infused with 60 μg/kg LPS in a 500 μl bolus of saline through the venous catheter. Serum TNF-α levels were measured as described in Example 1 at time points of baseline, 45 minutes, 90 minutes, and 180 minutes following LPS infusion. Serum TNF-α levels as a function of time after LPS infusion and completion of stimulation is shown in FIG. 26. It was found that the RC pattern was equally effective for reducing TNF-α release compared to a tonic pattern despite fewer pulses being delivered, and thus may be an optimal method when delivering stimulation using a wirelessly-charged implanted device in order to minimize use time, power consumption, and so that the device can charge during the dwell time.

Example 16: Splenic Nerve Stimulation Pulse Polarity for Modulation of Cytokine Release In order to test how the order of cathodal and anodal phases of a biphasic stimulatory pulse delivered to the splenic affects modulation of serum cytokine levels in subjects after stimulation of the splenic nerve, the splenic nerve was stimulated using 2 different types of stimulatory pulses—the first contained pulses with a leading cathodal phase followed by a anodal phase after a dwell time ("Cathodal Stimulation"), while the second contained pulses with a leading anodal phase followed by a cathodal phase after a dwell time ("Anodal stimulation"). This was compared to sham stimulation, in which animals underwent placement of the stimulation electrodes but were not stimulated.

Figure 27A:
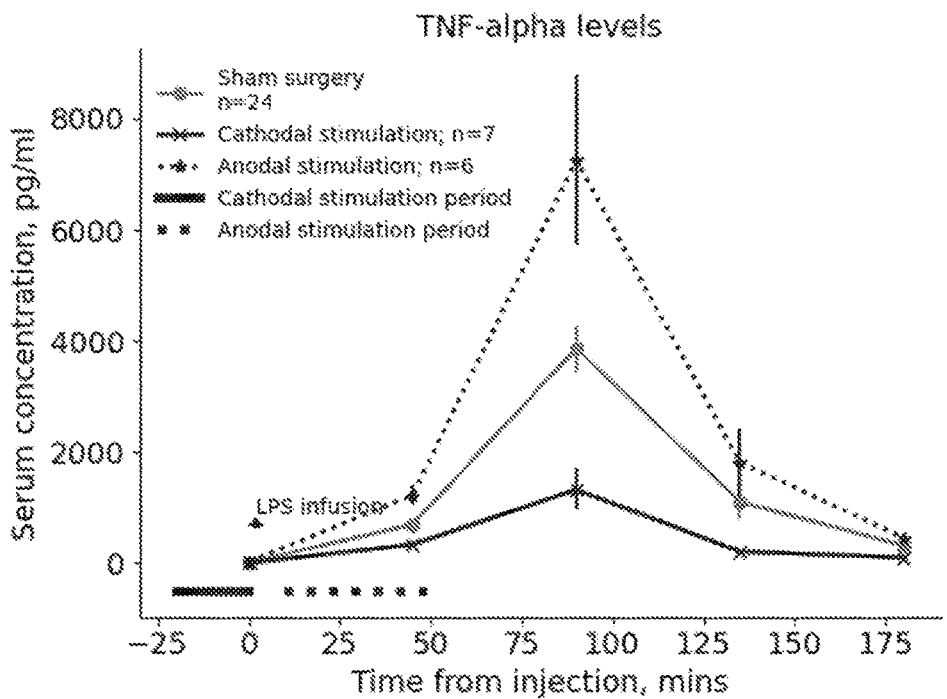
FIGS. 27A-27C show the effect of phase order on TNF-α levels (FIG. 27A). IL-6 levels (FIG. 27B), and IL-1β (FIG. 27C) levels in 3 cohorts of rats. In the first cohort ("Cathodal stimulation"), the splenic nerve was stimulated with a series of pulses (continuous 300 µs pulses, split evenly between cathodal and anodal phases, with a 60 µs inter-phase interval, and with the cathodal phase occurring first) at a constant rate of 5 Hz and an amplitude of 1.8 mA for 20 minutes. For this group, stimulation began 20 minutes prior to the infusion of 60 µg/kg LPS in a 500 µl bolus of saline through the venous catheter in order to induce an immune reaction. For the second group ("Anodal stimulation," n=6), the splenic nerve was stimulated with a series of pulses (continuous 300 µs pulses, split evenly between anodal and cathodal phases, with a 60 µs inter-phase interval, and with the anodal phase occurring first) at a rate of 30 Hz and an amplitude of 1.8 mA for 40 minutes. For this group, stimulation began 10 minutes after to the infusion of 60 µg/kg LPS in a 500 µl bolus of saline through the venous catheter. A control cohort (n=24) was implanted with the electrodes and infused with LPS, but did not receive any stimulatory pulses. Horizontal bars show the onset and offset of each stimulation type.
Figure 27B:
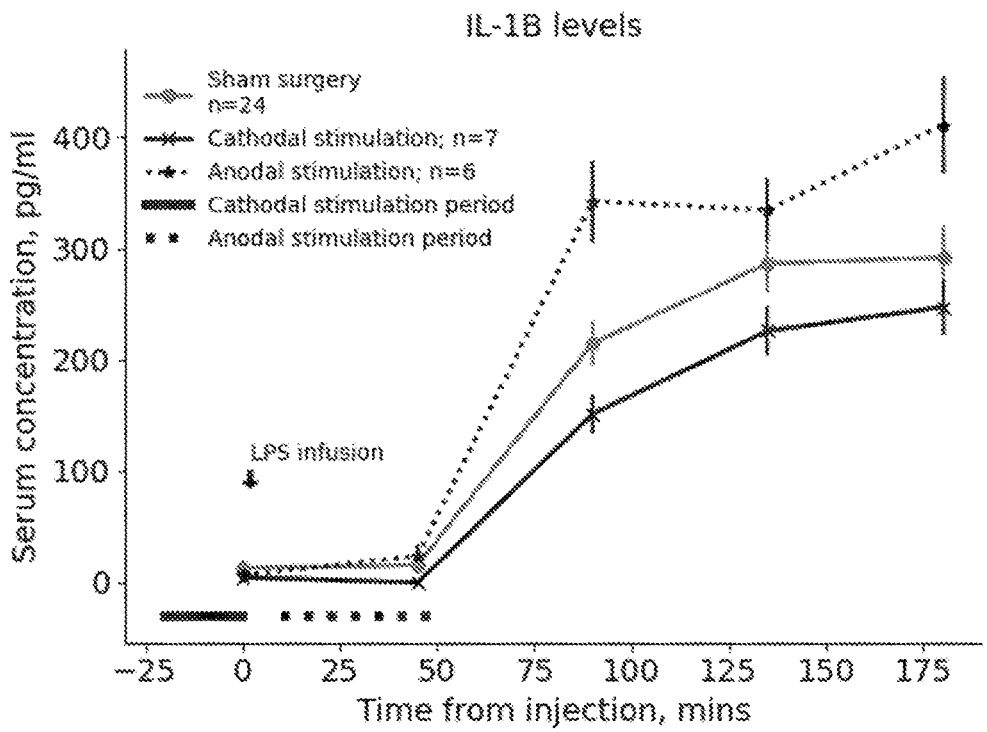
Figure 27C:
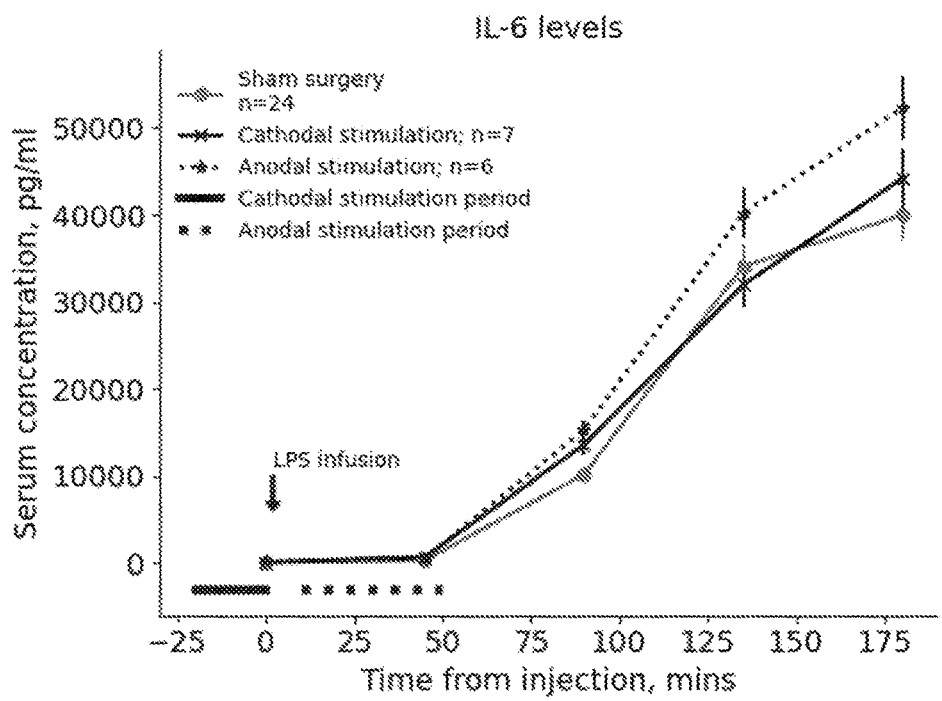

The splenic neurovascular bundle was exposed and cuff electrodes were implanted for a cohort of rats as described in Example 1. The splenic nerve of the first group ("Cathodal stimulation," n=7) was stimulated with a series of pulses (continuous 300 μs pulses, split evenly between cathodal and anodal phases, with a 60 μs inter-phase interval, and with the cathodal phase occurring first) at a constant rate of 5 Hz and an amplitude of 1.8 mA for 20 minutes. For this group, stimulation began 20 minutes prior to the infusion of 60 μg/kg LPS in a 500 μl bolus of saline through the venous catheter in order to induce an immune reaction. For the second group ("Anodal stimulation," n=6), the splenic nerve was stimulated with a series of pulses (continuous 300 μs pulses, split evenly between anodal and cathodal phases, with a 60 μs inter-phase interval, and with the anodal phase occurring first) at a rate of 30 Hz and an amplitude of 1.8 mA for 40 minutes. For this group, stimulation began 10 minutes after to the infusion of 60 μg/kg LPS in a 500 μl bolus of saline through the venous catheter. A control cohort (n=24) was implanted with the electrodes and infused with LPS, but did not receive any stimulatory pulses. Serum TNF-α, IL-6, and IL-1β were measured as described in Example 1 at time points of baseline, 45 minutes, 90 minutes, and 180 minutes following LPS infusion. It was found that stimulatory pulses that included a cathodal-first pulse pattern decreased TNF-α levels (FIG. 27A) as well as IL-1β levels (FIG. 27B), while IL-6 levels were unchanged (FIG. 27C). Conversely, stimulation that included anodal-first pulses resulted in increases in all three of the measured cytokines. This demonstrates that the nature of pulses emitted during stimulation, especially the order of pulse polarity, can be modulated in order to have differential effects on cytokine release.

Example 17: Measurement of Circulating Peripheral Immune Cell Levels after Splenic Nerve Stimulation with Two Pulse Patterns In order to test how the splenic nerve stimulatory pulse pattern, including amplitude modulations, affects circulating natural killer cell levels in subjects after stimulation of the splenic nerve, the splenic nerve was stimulated using 2 different patterns of stimulation. In one cohort of rats, the splenic nerve was stimulated using a series of electrical pulses in a cohort of rats with a dwell time (i.e., a quiescent period) between pulse trains ("Burst stimulation"). In the other cohort, the splenic nerve was again stimulated with a series of electrical pulses with dwell time (i.e., a quiescent period) between pulse trains. However, in this cohort of rats, the amplitude of stimulatory pulses was monotonically increased at the start of each new pulse train, so that each pulse train consisted of a number of pulses at a fixed amplitude, but the subsequent pulse train consisted of pulses at a higher amplitude than the previous train, termed "RC Stimulation".

Figure 28:
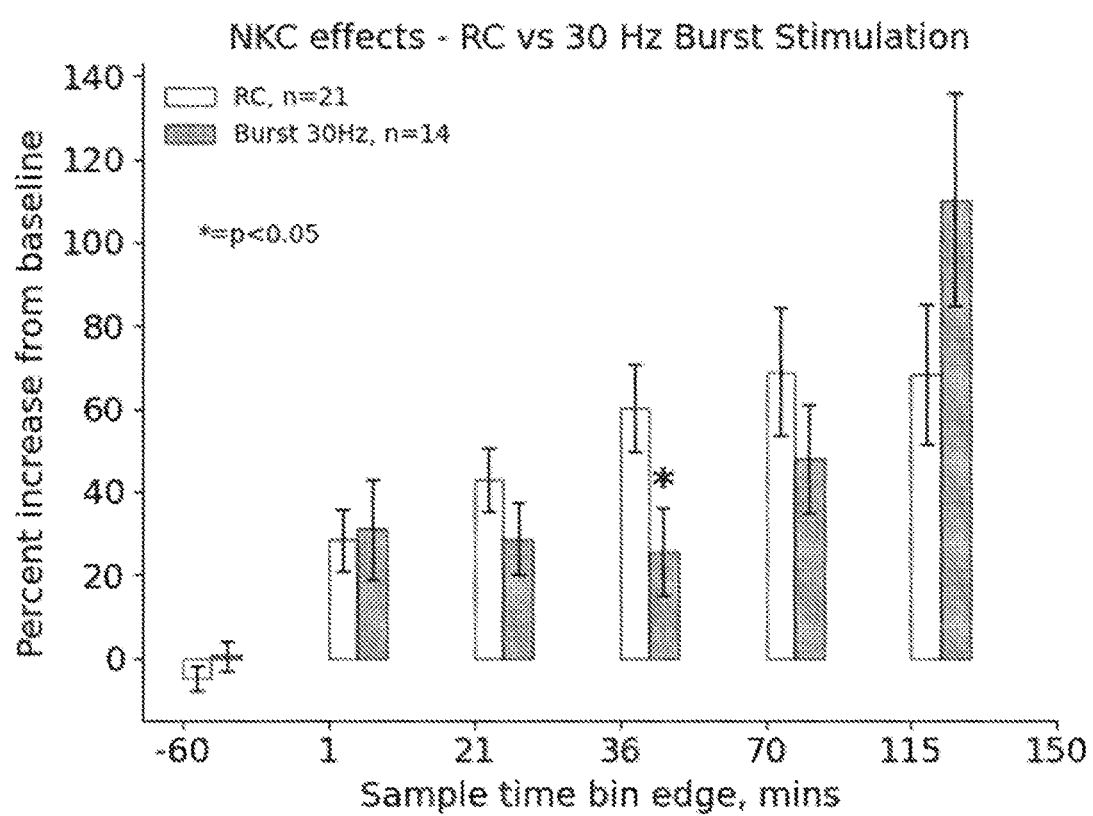
FIG. 28 shows the levels of circulating natural killer (NK) in two cohorts of rats stimulated with different patterns of pulses. The splenic nerve of the first group (n=21) was stimulated with an "RC" pulse train, which consisted of an average of 10 trains with an average of 60 pulses, with each pulse train separated by a 20-40 second dwell time. All pulse trains consisted of 300 µs pulses (split evenly between cathodal and anodal phases, with a 60 µs inter-phase interval) delivered at 3 Hz. The first pulse train consisted of a set pulses beginning at 0.5 mA, and the amplitude of all pulses in each successive pulse train was increased monotonically up to 6 mA. In the second group of rats, the nerve was stimulated with a 1.8 mA "burst" pulse train, consisting of a series of pulses (continuous 300 µs pulses, split evenly between cathodal and anodal phases, with a 60 µs inter-phase interval) at 30 Hz for 30 seconds, followed by a dwell time of 30 seconds (n=14). This pattern was repeated for a total of 20 minutes. Blood samples were collected immediately prior to stimulation and within 5 time bins after stimulation. The number of natural killer cells in each sample was measured using flow cytometry. Asterisks denote statistically significant (P<0.05) differences between the groups at a given time bin.

Levels of circulating natural killer (NK) cells were compared in the samples taken before stimulation and after stimulation at several time points. The splenic neurovascular bundle was exposed and cuff electrodes were implanted for a cohort of rats as described in Example 1. The splenic nerve of the first group (n=21) was stimulated with an "RC" pulse train, which consisted of an average of 10 trains with an average of 60 pulses, with each pulse train separated by a 20-40 second dwell time. All pulse trains consisted of 300 μs pulses (split evenly between cathodal and anodal phases, with a 60 μs inter-phase interval) delivered at 3 Hz. The first pulse train consisted of a set pulses beginning at 0.5 mA, and the amplitude of all pulses in each successive pulse train was increased monotonically up to 6 mA. Alternately, the nerve was stimulated with a 1.8 mA "burst" pulse train, consisting of a series of pulses (continuous 300 μs pulses, split evenly between cathodal and anodal phases, with a 60 μs inter-phase interval) at 30 Hz for 30 seconds, followed by a dwell time of 30 seconds (n=14). This pattern was repeated for a total of 20 minutes. Blood samples were collected immediately prior to stimulation and at 5 time points after stimulation. The number of natural killer cells in each sample was measured using flow cytometry. The levels of NK cells in each cohort increased after the onset of stimulation. However, the magnitude of these increases was different. For RC stimulation, the effect was stronger between 21 minutes and 115 minutes after stimulation onset, with a statistically significant (P<0.05) difference observed between 36 and 70 minutes. However, the effect was stronger for burst stimulation between 115 and 150 minutes (FIG. 28). This example demonstrates that the pattern of pulses, including the timing of pulse trains and modulation of pulse amplitudes, can differentially effect the levels of circulating immune cells in a subject.

What is claimed is:

1. A method of treating a cancer in a subject, comprising: electrically stimulating the splenic nerve of the subject using a fully implanted device comprising one or more electrodes in electrical communication with the splenic nerve sufficient to increase activation or circulation of natural killer (NK) cells of the subject and treat the cancer in the subject.

2. The method of claim 1, wherein the immune system is modulated to increase activation of one or more other immune cells in the subject.

3. The method of claim 2, wherein the immune system is modulated to increase activation of cytotoxic T-cells in the subject.

4. The method of claim 1, wherein the splenic nerve is electrically stimulated with a plurality of electrical pulses emitted at a frequency of less than 25 Hz.

5. The method of claim 1, wherein the splenic nerve is electrically stimulated with a plurality of electrical pulses emitted at a frequency of about 3 Hz to about 20 Hz.

6. The method of claim 1, comprising:
receiving, at the device, ultrasonic waves from an external ultrasonic transducer; and
converting energy from the ultrasonic waves into electrical energy that powers the device.

7. The method of claim 6, comprising transmitting the ultrasonic waves that power the implanted device using an external device.

8. The method of claim 1, wherein the splenic nerve is electrically stimulated using one or more electrical pulses about 5 ms in length or less.

9. The method of claim 1, wherein the splenic nerve is electrically stimulated using one or more electrical pulses having an amplitude of about 250 μA to about 50 mA.

10. The method claim 3, wherein the splenic nerve is electrically stimulated using one or more electrical pulses at a frequency of about 100 Hz or less.

11. The method of claim 1, wherein the splenic nerve is electrically stimulated using a pulse train comprising a plurality of biphasic electrical pulses.

12. The method of claim 11, wherein the biphasic electrical pulses comprises an anodal phase followed by a cathodal phase.

13. The method of claim 11, wherein the biphasic electrical pulses comprises a cathodal phase followed by an anodal phase.

14. The method of claim 1, wherein the splenic nerve is electrically stimulated using a plurality of pulse trains comprising two or more electrical pulses, the pulse trains separated by a dwell time of about 50 ms or more.

15. The method of claim 14, wherein the plurality of pulse trains comprises at least a first pulse train followed by a second pulse train, wherein electrical pulses in the first pulse train have an amplitude lower than an amplitude of electrical pulses in the second pulse train.

16. The method of claim 1, wherein the splenic nerve is electrically stimulated using tonic electrical pulses.

17. The method of claim 1, wherein the implanted device is fully implanted with in within the perivascular fascia surrounding the splenic nerve and splenic artery.

* * * * *